United States Patent [19]
Panetta et al.

[11] Patent Number: 5,942,530
[45] Date of Patent: *Aug. 24, 1999

[54] METHOD FOR TREATING PAIN

[75] Inventors: Jill Ann Panetta, Zionsville; Harlan Edgar Shannon, Carmel, both of Ind.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/138,495

[22] Filed: Aug. 24, 1998

Related U.S. Application Data

[60] Provisional application No. 60/057,389, Aug. 28, 1997.

[51] Int. Cl.$^6$ .......................... A61K 31/42; A61K 31/44; A61K 31/425
[52] U.S. Cl. .......................... 514/374; 514/340; 514/342; 514/365
[58] Field of Search ...................................... 514/374, 340, 514/342, 365

[56] References Cited

U.S. PATENT DOCUMENTS

| | | | |
|---|---|---|---|
| 4,895,953 | 1/1990 | Musser et al. | 548/204 |
| 5,036,079 | 7/1991 | Clark et al. | 514/333 |
| 5,403,852 | 4/1995 | Barreau et al. | 514/374 |
| 5,428,048 | 6/1995 | Malamas et al. | |
| 5,491,159 | 2/1996 | Malamas | 514/374 |
| 5,498,621 | 3/1996 | Dow et al. | 514/369 |

FOREIGN PATENT DOCUMENTS

| | | |
|---|---|---|
| 0 310 370 | 4/1989 | European Pat. Off. |
| 1 564 081 | 4/1969 | France . |
| 2 066 250 | 12/1979 | United Kingdom . |
| WO 98 15274 | 4/1998 | WIPO . |

OTHER PUBLICATIONS

M.S. Malamas, et al.: Azole Phenoxy Hydroxyureas as Selective and Orally Active Inhibitors of 5–Lipoxygenase *Journal of Medicinal Chemistry,* vol. 39, No. 1, 1996, pp. 237–245.

*Primary Examiner*—William R. A. Jarvis
*Attorney, Agent, or Firm*—Nelsen L. Lentz; Arleen Palmberg

[57] ABSTRACT

The present invention provides a method for treating pain using a composition comprising certain phenyl oxazoles or phenyl thiazoles in combination with a Drug Useful in the Treatment of Pain.

38 Claims, No Drawings

METHOD FOR TREATING PAIN

This application claims the benefit of U.S. Provisional Application No. 60/057,389, filed Aug. 28, 1997.

FIELD OF THE INVENTION

This invention provides a method for treating pain comprising administering certain phenyl oxazoles or phenyl thiazoles in combination with another Drug Useful in the Treatment of Pain to an animal in need of such treatment.

BACKGROUND OF THE INVENTION

This invention relates to a therapeutic combination of compounds to provide analgesic activity.

For clinical purposes, pain can be categorized into three groups: (1) acute pain; (2) continuous pain in terminally ill patients; and (3) other forms of chronic pain. In acute pain, a specific noxious stimulant of limited duration can be identified.

An additional distinction that is relevant to chronic pain is the difference between pain caused by a tissue-damaging process that excites nociceptive afferents and pain caused by pathologic changes in nociceptive neurons (neuropathic pain). Nociception refers to the neural mechanisms by which noxious stimuli are detected.

Nociception involves two steps: transductions of noxious stimuli by peripheral nerve endings and transmission of these signals to the central nervous system. Neuropathic pain typically persists and may even have its onset long after the original causative stimulus has been removed.

There are many Drugs Useful for the Treatment of Pain which are known in the literature and to the skilled artisan. Oral combinations of aspirin with codeine or other narcotic analgesics are known to provide additive analgesic effects in man. The Pharmacological Basis of Therapeutics, 5th edition, Macmillan Publishing Co., 1975, pp. 325–358.

More active analgesic combinations are in constant demand because they offer the attractive possibility of relieving pain with reduced dosages, thereby diminishing the expected side effects and toxicity that would otherwise result from higher dosages. It would be particularly desirable to acquire a synergistic combination effect. Such a composition is the subject of the present invention.

The phenyl oxazole and phenyl thiazole compounds of the instant invention are useful for the treatment of neurodegeneration. Surprisingly, and in accordance with this invention, Applicants have discovered that these phenyl oxazoles and phenyl thiazoles can be useful for the treatment of pain and can provide a synergistic effect when administered with one or more other Drugs Useful in the Treatment of Pain. The combination could address a long felt need for a safe and effective treatment for pain.

SUMMARY OF THE INVENTION

The present invention provides a method for treating pain comprising administering to a patient in need thereof, an analgesic composition comprising a compound of formula I;

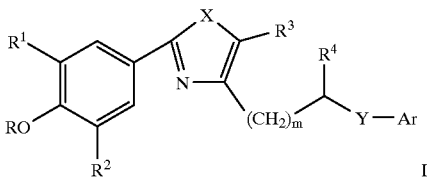

(I)

wherein:
Ar is phenyl or pyridyl substituted with zero to two substituents selected from the group consisting of $C_1$–$C_6$ alkyl, hydroxy and halo; and
substituted with either:
(i) one or two substituents selected from the group consisting of

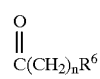

and ($C_1$–$C_6$ alkyl)$R^6$; or
(ii) two substituents which when taken together with the carbon atoms to which they are attached form a pyridyl or tetrahydropyridyl ring;
provided that when substituent pattern (i) is present, the phenyl or pyridyl group of Ar may additionally be substituted with two substituents which when taken together with the carbon atoms to which they are attached form a phenyl ring;
where $R^6$ is $NR^7R^8$, morpholin-1-yl, imidazol-1-yl, 4,5-dihydro-1H-imidazol-2-yl, thiomorpholin-1-yl, piperazin-1-yl or piperazin-1-yl substituted with $C_1$–$C_4$ alkyl or

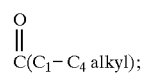

and $R^7$ and $R^8$ are each individually hydrogen, $C_1$–$C_6$ alkyl, $(CH_2)_p OH$ or $(CH_2)_p$-piperidyl;
X is O or S;
Y is $CHR^5$, O or S;
R is H or $C_1$–$C_6$ alkyl;
$R^1$ and $R^2$ are each individually $C_1$–$C_6$ alkyl;
$R^3$ is H or $C_1$–$C_6$ alkyl;
$R^4$ is hydrogen, or when Y is $CHR^5$, $R^4$ and $R^5$ are each individually H or when taken together form a bond;
m is 0 or 1;
n is an integer from 0 to 4 both inclusive; and
p is an integer from 1 to 6 both inclusive;
or a pharmaceutically acceptable salt, hydrate or optical isomer thereof; and one or more Drugs Useful in the Treatment of Pain in a weight ratio of a compound of formula I to Drug Useful in the Treatment of Pain of from about one (1) part of a compound of formula I to from about one (1) to about one thousand (1000) parts Drug Useful in the Treatment of Pain.

More specifically, the invention provides a method of synergistically treating pain in an animal using certain phenyl oxazoles or phenyl thiazoles in combination with a Drug Useful in the Treatment of Pain to provide a synergistic effect.

The present invention, further, provides a method for treating acute pain, including for example, but not limited to headache, arthritis, simple muscle strain, and dysmenorrhea.

Additionally, this invention provides a method for treating nociceptive pain, particularly post-operative pain, cluster headaches, dental pain, surgical pain, pain resulting from severe burns, for example third degree burns, post partum pain, angina pain, genitourinary tract related pain, and including cystitis.

The present invention provides in addition a method for treating neuropathic pain including lower back pain, pain associated with arthritis, cancer-associated pain, herpes neuralgia, phantom limb pain, central pain, opiod resistant neuropathic pain, bone injury pain, and pain during labor and delivery.

The invention further provides a composition for treating pain comprising a compound of formula I or a pharmaceutically acceptable salt or solvate thereof and one or more Drug Useful in the Treatment of Pain in a weight ratio of a compound of formula I to Drug Useful in the Treatment of Pain of from about one part of a compound of formula I to from about one (1) to about one thousand (1000) parts Drug Useful in the Treatment of Pain.

DETAILED DESCRIPTION OF THE INVENTION

As used herein, the term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, sec-butyl, isobutyl, t-butyl, n-pentyl, isopentyl, neopentyl, hexyl and the like.

The term "halo" means chloro, fluoro, bromo or iodo.

The term "pharmaceutically acceptable salts" refers to salts of the compounds of the above formulae which are substantially non-toxic to living organisms. Typical pharmaceutically acceptable salts include those salts prepared by reaction of the compounds of the above formulae with a pharmaceutically acceptable mineral or organic acid, or a pharmaceutically acceptable alkali metal or organic base, depending on the types of substituents present on the compounds of the formulae.

Examples of pharmaceutically acceptable mineral acids which may be used to prepare pharmaceutically acceptable salts include hydrochloric acid, phosphoric acid, sulfuric acid, hydrobromic acid, hydroiodic acid, phosphorous acid and the like. Examples of pharmaceutically acceptable organic acids which may be used to prepare pharmaceutically acceptable salts include aliphatic mono and dicarboxylic acids, such as oxalic acid, carbonic acid, citric acid, succinic acid, phenyl-substituted alkanoic acids, aliphatic and aromatic sulfuric acids and the like. Such pharmaceutically acceptable salts prepared from mineral or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

It should be recognized that the particular anion or cation forming a part of any salt of this invention is not critical, so long as the salt, as a whole, is pharmacologically acceptable and as long as the anion or cationic moiety does not contribute undesired qualities.

The term "amino-protecting group" is used herein as it is frequently used in synthetic organic chemistry, to refer to a group which will prevent an amino group from participating in a reaction carried out on some other functional group of the molecule, but which can be removed from the amine when it is desired to do so. In a similar fashion, the term "hydroxy protecting group" refers to a removable group which will prevent a hydroxy group from participating in a reaction performed on the molecule. Such groups are discussed by T. W. Greene in chapters 2 and 7 of *Protective Groups in Organic Synthesis*, John Wiley and Sons, New York, 1981, and by J. W. Barton in chapter 2 of *Protective Groups in Organic Chemistry*, J. F. W. McOmie, ed., Plenum Press, New York, 1973, which are incorporated herein by reference in their entirety. Examples of amino protecting groups include benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. A preferred amino-blocking group is t-butoxycarbonyl.

Examples of hydroxy protecting groups include ether and substituted ether forming groups such as methyl, methoxymethyl, t-butoxymethyl, 1-ethoxyethyl and benzyl; silyl ether forming groups such as trimethylsilyl, triethylsilyl and methyl-diisopropylsilyl; ester forming groups such as formate, acetate and trichloroacetate and carbonate groups, such as methyl, 2,2,2-trichloroethylcarbonate and p-nitrophenyl carbonates.

When Ar is a phenyl or pyridyl substituted with one or two —($C_1$–$C_6$ alkyl)$R^6$ groups, the compounds of formula I may exist in various isomeric forms. This invention is not related to any particular isomer but includes all possible individual isomers and racemates.

Many of the compounds of formula I can combine with water to form hydrates. This invention encompasses the hydrates of formula I.

As used herein the term "pain" shall refer to all types of pain. Preferably, the term shall refer to chronic pains, such as neuropathic pain, and post-operative pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term shall also preferably refer to nociceptive pain or nociception.

As used herein the term "treating" includes prophylaxis of a physical and/or mental condition or amelioration or elimination of the developed condition once it has been established or alleviation of the characteristic symptoms of such condition.

As used herein, the term "Drug Useful in the Treatment of Pain" shall mean a compound; or a pharmaceutically acceptable salt thereof, that is known to the artisan to have clinical analgesic activity. As used herein, Drug Useful in the Treatment of Pain shall include, but is in no way limited to, NSAIDS, opioid compounds, and alpha adrenergic compounds.

As used herein the term "parts", with reference to the composition, shall refer to parts by weight in the composition in proportion to the Drug Useful in the Treatment of Pain or a compound of formula I, as the case may be.

Drugs Useful in the Treatment of Pain shall also encompass classical analgesic agents known to the artisan. See for example, Goodman and Gillman, The Pharmacological Basis of Therapeutics, 5th edition, Macmillan Publishing Co., 1975, pp. 325–358, and similar references commonly consulted by the skilled artisan. Thus, the term shall include, for example, Tylenol® #3, tricyclic antidepressants (for example desipramine, imipramine, amytriptiline, nortriptiline), anticonvulsants (for example, carbamazepine, gatapentine, valproate), and serotonin reuptake inhibitors (for example, fluoxetine, paroxetine, citalopram, sertraline), mixed serotonin-norepinephrine reuptake inhibitors (for example venlafaxine, duloxetine), serotonin receptor agonists and antagonists, cholinergic (muscarinic and nicotinic) analgesics, and neurokinin antagonists.

Especially preferred Drugs Useful in the Treatment of Pain can be selected from the group consisting of tricyclic antidepressants, anticonvulsants, and serotonin-norepinephrine reuptake inhibitors.

The term "alpha-adrenergic compounds", as used herein, represents a compound having central alpha-adrenergic receptor activity. The most preferred central alpha-adrenergic active compound is clonidine or a pharmaceutically acceptable salt thereof having the chemical name: 2-(2,6-dichlorophenylamino)-2-imidazoline. New alpha adrenergic active agents are undergoing pharmacological development. The present invention encompasses all such agents which function as a central alpha-adrenergic active compound.

Clonidine is known to be useful for treating hypertension. see Physicians' Desk Reference, 45th Ed. (1991) p. 673.

The term "opioids" or "opioid compounds", as used herein, has the meaning commonly associated with the term by the skilled artisan. Preferred opioid compounds are selected from the group consisting of morphine, codeine, meperidine, methadone, propoxyphene, levorphanol, hydromorphone, oxymorphone, oxycodone, brompton's cocktail, pentazocine, butorphanol, nabuphine, and buprenorphine.

The term "NSAIDS", as used herein, represents a non-steroidal anti-inflammatory drug which can be identified as such by the skilled artisan. For example, the Merck Manual, 16th Edition, Merck Research Laboratories (1990) pp. 1308–1309 provide well known examples of NSAIDS. The term is intended to include, but is not limited to salicylates such as aspirin. Further, the term includes, but is not limited to, indomethacin, ibuprofen, naproxen, fenoprofen, tolmetin, sulindac, meclofenamate, ketoprofen, piroxicam, flurbiprofen, and diclofenac. Especially preferred NSAIDS include ibuprofen, and naproxen. Another especially preferred NSAID is aspirin. Particularly preferred NSAIDS include aspirin and ibuprofen. The salicylates may include acetylsalicylic acid, sodium acetylsalicylic acid, calcium acetylsalicylic acid, salicylic acid, and sodium salicylate. The term NSAIDS shall refer to any compound acting as a non-steroidal anti-inflammatory agent. Applicants appreciate that new NSAIDS may be in development, and the present invention contemplates a synergistic composition comprising such new agents with olanzapine as well.

As used herein, the term "animal" shall refer to a vertebrate animal. Most preferably, the vertebrate animal is a mammal. As used herein, the term "mammal" shall refer to the Mammalia class of higher vertebrates.

The term "mammal" includes, but is not limited to, a human. The term "treating" as used herein includes prophylaxis of the named condition or amelioration or elimination of the condition once it has been established.

PREFERRED COMPOUNDS OF THE INVENTION

Preferred groups of compounds of formula I include the following:

(a) Ar is phenyl substituted with one or two substituents selected from

and $(C_1-C_6 \text{ alkyl})R^6$ or with two substituents which when taken together with the carbon atoms to which they are attached form a pyridyl or tetrahydropyridyl ring;

(b) Ar is phenyl substituted with $C_1-C_6$ alkyl, hydroxy, halo or with two substituents which when taken together with the carbon atoms to which they are attached form a phenyl ring;

(c) Ar is pyridyl substituted with $C_1-C_6$ alkyl, hydroxy, halo or with two substituents which when taken together with the carbon atoms to which they are attached form a phenyl ring;

(d) Ar is phenyl substituted with $(C_1-C_6 \text{ alkyl})R^6$;

(e) Ar is phenyl substituted with

(f) $R^6$ is $NR^7R^8$;

(g) $R^6$ is morpholin-1-yl or thiomorpholin-1-yl;

(h) $R^6$ is imidazol-1-yl or 4,5-dihydro-1-1H-imidazol-2-yl;

(i) $R^6$ is piperazin-1-yl or piperazin-1-yl substituted with $C_1-C_4$ alkyl or

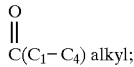

(j) $R^7$ and $R^8$ are each individually hydrogen or $C_1-C_6$ alkyl;

(k) $R^1$ and $R^2$ are each individually $C_1-C_6$ alkyl;

(l) $R^3$ is $C_1-C_6$ alkyl;

(m) Y is O or S;

(n) Y is $CHR^5$;

(o) m is 1;

(p) p is an integer from 1–3 both inclusive.

It will be understood that the above classes may be combined to form additional preferred classes.

A preferred genus of compounds include those compounds where:

Ar is phenyl substituted with one or two substituents selected from

and $(C_1-C_6 \text{ alkyl})R^6$ where $R^6$ is $NR^7R^8$ and $R^7$ and $R^8$ are H or $C_1-C_6$ alkyl;

and one or two substituents selected from hydrogen, $C_1-C_6$ alkyl and hydroxy; or two substituents which when taken together with the carbon atoms to which they are attached form a phenyl group.

$R^1$ and $R^2$ are $C_1$–$C_6$ alkyl;

R, $R^3$ and $R^4$ are hydrogen;

X is O;

Y is O or S;

Of this preferred genus, compounds in which $R^1$ and $R^2$ are 1,1-dimethylethyl are more preferred.

Of this more preferred genus, those compounds in which Ar is phenyl substituted with one or two ($C_1$–$C_6$ alkyl)$R^6$ groups and one or two substituents selected from hydrogen and $C_1$–$C_6$ alkyl are especially preferred.

Of this especially preferred genus, those compounds in which Ar is phenyl substituted with ($C_1$–$C_6$ alkyl)$R^6$ are particularly preferred.

A preferred composition is a weight ratio of a compound of formula I to Drug Useful in the Treatment of Pain of from about one (1) part of a compound of formula I to from about one (1) to about hundred (100) parts Drug Useful in the Treatment of Pain. An especially preferred ratio is from about one part of a compound of formula I (1) to from about one (1) to about thirty (30) parts Drug Useful in the Treatment of Pain. A further preferred ratio may be from about one part of a compound of formula I to from about one (1) to about ten (10) parts Drug Useful in the Treatment of Pain. A final preferred ratio may be from about one (1) part of a compound of formula I to from about one (1) to about three (3) parts Drug Useful in the Treatment of Pain.

One preferred group of Drugs Useful in the Treatment of Pain are Non-Steroidal Anti-inflammatory Agents (hereinafter "NSAIDS") and include, but are in no way limited to salicylates such as aspirin. Another preferred group of NSAIDS include, but are not limited to, indomethacin, ibuprofen, naproxen, fenoprofen, tolmetin, sulindac, meclofenamate, ketoprofen, piroxicam, flurbiprofen, and diclofenac.

Particularly preferred NSAIDS are selected from the group consisting of ibuprofen, and naproxen. Another particularly preferred NSAIDS is aspirin.

SYNTHESIS METHODS

The compounds of formula I where Ar is phenyl substituted with one or two ($C_1$–$C_6$ alkyl)$R^6$ groups where the alkyl group is $CH_2$, X and Y are oxygen and m is 1 are prepared according to the following general reaction scheme I.

Scheme I(a)

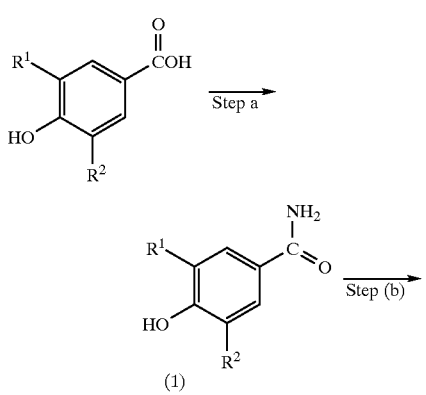

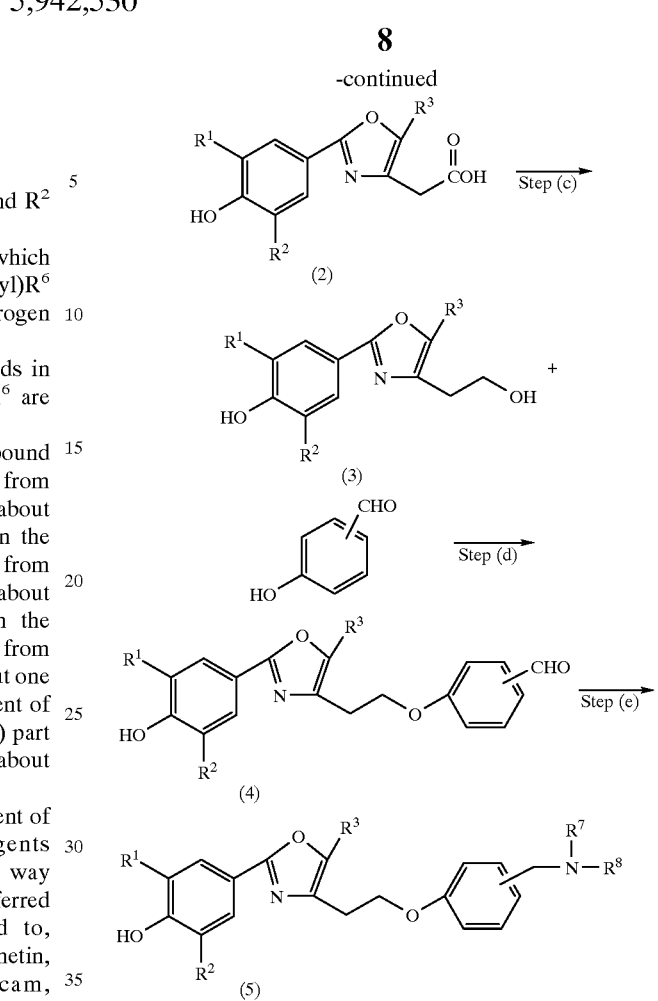

In step (a) of the above reaction scheme, an appropriately substituted benzoic acid is converted to the benzamide (1) by refluxing with an activating agent such as 1,1'-carbonyldiimidazole then cooling to ambient temperature and treating with concentrated aqueous ammonia. The reaction can be conducted in an aprotic polar solvent such as tetrahydrofuran for a period of from 1 to 24 hours.

The oxazoleacetic acid compound (2) is prepared in step (b) by cyclizing the benzamide (1) with a reagent such as ethyl-4-chloroacetoacetate under an inert gas such as nitrogen at a temperature of about 50° C. to 130° C. for about one to two hours and then hydrolyzing to form the acid.

Preparation of the phenyloxazole (3) is achieved in step (c) by reducing the acid (2) with a reducing agent such as borane tetrahydrofuran. The reaction can be conducted in an aprotic polar solvent such as tetrahydrofuran at ambient temperature for about 1 to 24 hours.

In step (d), the phenyloxazole (3) can be coupled with a hydroxy substituted benzaldehyde to form aldehyde (4) by first mesylating (3) with a mesylating agent such as methanesulfonyl chloride and then coupling the mesylated compound with the benzaldehyde. The coupling reaction can be conducted in an aprotic polar solvent such as dimethyl sulfoxide in the presence of potassium t-butoxide while heating to a temperature of about 70° C. for up to 24 hours.

When $R^1$ and $R^2$ are small lower alkyl substituents such as methyl or ethyl, the hydroxy of the phenyl ring is preferably protected with a hydroxy protecting group to prevent mesylation of the phenol. The protecting group may then be removed after the coupling step.

When $R^1$ and $R^2$ are bulky alkyl substituents such as t-butyl, mesylation preferentially occurs on the alcohol attached to the oxazole or thiazole ring, thus the hydroxy does not need to be protected.

Alternately, preparation of (4) can be accomplished by a Mitsunobu coupling which can be conducted in an aprotic polar solvent, such as tetrahydrofuran, at ambient temperature.

Reductive amination of the aldehyde to form desired product (5) is accomplished in step (e) by reacting compound (4) with an appropriately substituted amine and titanium IV isopropoxide (Ti(OiPr)$_4$) using a reducing agent such as sodium borohydride. The reaction is preferably conducted at ambient temperature in a low molecular weight alcohol such as ethanol. The reaction is substantially complete in 16 hours to 3 days.

Alternately, the reduction step (e) can be accomplished by dissolving the aldehyde (4) in a low molecular weight alcohol, such as methanol, acidifying the solution with an excess of an organic acid, such as acetic acid, then reacting the aldehyde (4) with an appropriately substituted amine using a reducing agent, such as sodium cyanoborohydride (NaCNBH$_3$). The reaction is conducted at ambient temperatures under an inert gas, such as nitrogen, and the reaction is substantially complete in about six hours.

Compounds of Formula I where R is $C_1$–$C_6$ alkyl can be prepared by alkylating the phenol of compound (4) of Scheme I(a), after the coupling step (d), using an appropriate $C_1$–$C_6$ alkyl halide, such as methyl iodide, and sodium hydride in an aprotic polar solvent or solvent mixture such as tetrahydrofuran and dimethylformamide. The reaction may be conducted at ambient temperature and is substantially complete within 31 hours. Reductive amination can then be accomplished as described in Scheme I(a), step (e).

Compounds of Formula I where $R^7$ or $R^8$ are —(CH$_2$)$_p$piperidyl can be prepared as shown in Scheme I(b) below, by reacting the aldehyde (4) with an amine or an amine hydrochloride salt of the formula H$_2$NR$^{10}$ where R$^{10}$ is H or $C_1$–$C_6$ alkyl, to form the free amine (6), which can then be alkylated with an appropriately amino-protected piperidine such as N-tert-butoxycarbonyl-3-(3-bromopropyl)piperidine using sodium hydride in an aprotic polar solvent such as dimethylformamide to form (7). Temperatures of from about 20° C. to 80° C. are preferred and the reaction is substantially complete within 4 hours. Deprotection of the piperidyl group may be accomplished by techniques familiar to the skilled artisan such as by treatment of (7) with an acid such as hydrochloric acid.

Scheme I(b)

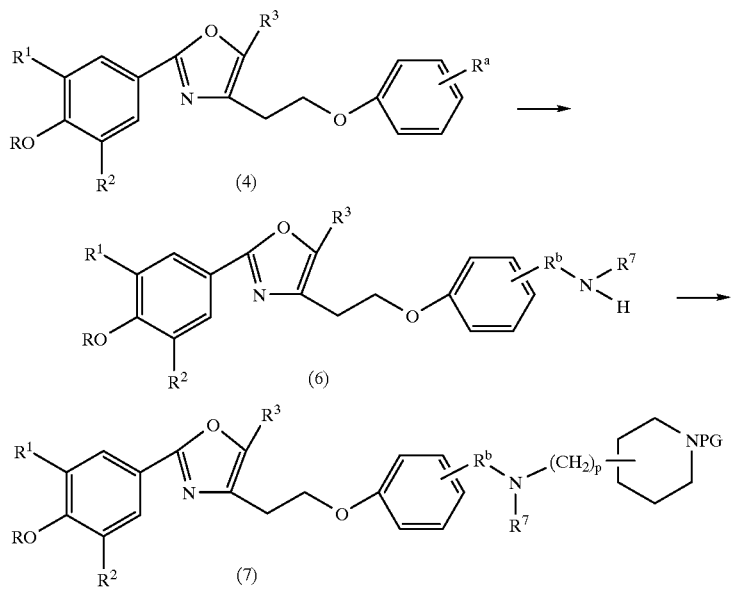

$R^a$ is oxo-substituted $C_1$-$C_6$ alkyl
$R^b$ is $C_1$-$C_6$ alkyl
PG is an amino protecting group Compounds of formula I where Ar is phenyl substituted with one or two straight chain ($C_2$–$C_6$ alkyl)R$^6$ groups and X, Y and R$^4$ are as defined in Scheme I(a) above can be prepared as described in Schemes I (c–e) below.

Scheme I(c)

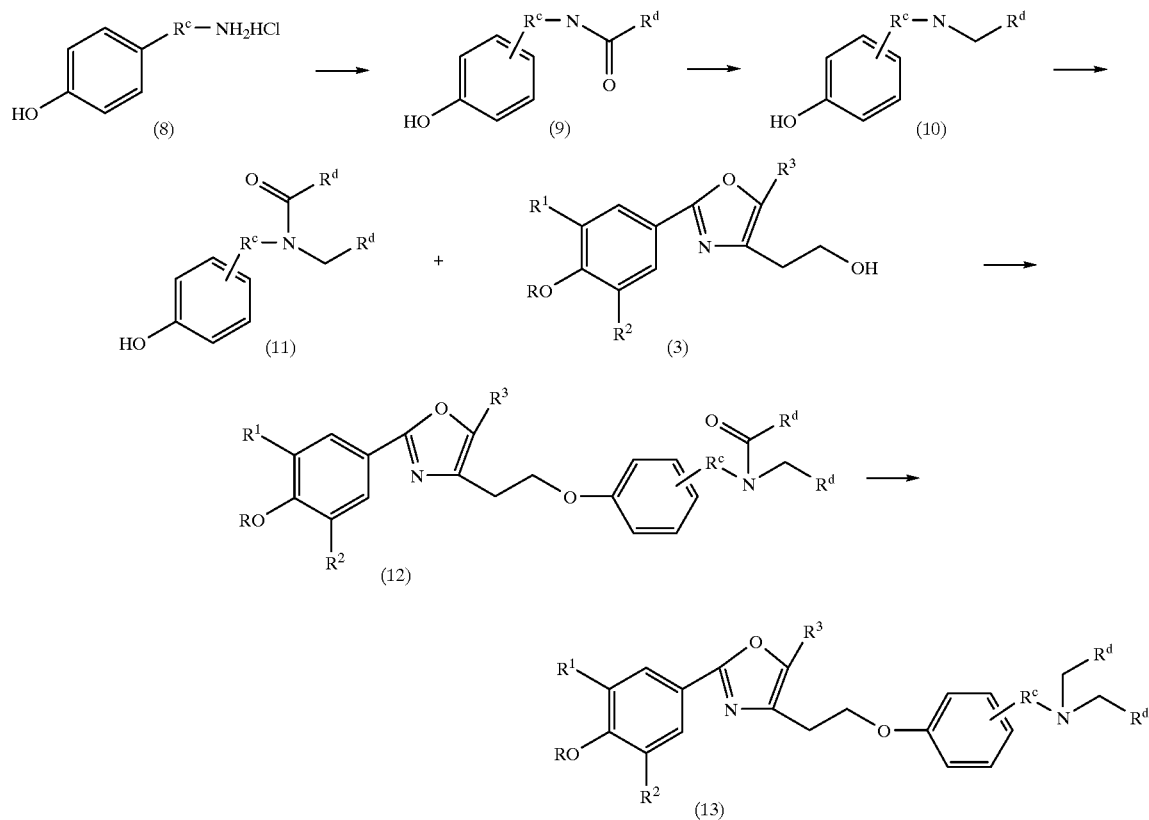

$R^c$ is $(CH_2)_q$ where q is an integer from 2-6
$R^d$ is H or $C_1-C_5$ alkyl In Scheme I(c), an amino-substituted phenol starting material (8) is reacted with an acylating agent such as acetic anhydride and sodium methoxide in a low molecular weight alcohol, such as methanol, to form compound (9). Reduction of the carbonyl can be achieved with a reducing agent, such as lithium aluminum hydride in an aprotic solvent, such as tetrahydrofuran to produce compound (10). Acylation of (10) can be accomplished by reacting 1,1-carbonyldiimidazole with a carboxylic acid in an aprotic polar solvent such as tetrahydrofuran at temperatures of from about 0° C. to about 20° C., then treating with N-ethyl-p-hydroxyphenethyl amine (10). The reaction is substantially complete in 2 to 24 hours.

Compound (11) can then be coupled with an appropriately substituted phenyloxazole in a Mitsunobu reaction to prepare (12). The reaction can be conducted in a polar aprotic solvent such as tetrahydrofuran at ambient temperature. After approximately 24 hours, the reaction is substantially complete. Compound (12) can then be reduced using a reducing agent, such as aluminum hydride in an aprotic solvent, such as tetrahydrofuran, to prepare (13). The reaction is appropriately conducted at ambient temperatures and is complete in about three hours.

In an alternate procedure, as shown in Scheme I(d) below, an appropriately substituted phenylalkanol starting material (14), dissolved in an organic solvent such as methylene chloride, is reacted with a halogenating agent such as dibromotriphenylphosphorane to prepare compound (15). The reaction may be conducted at ambient temperature and allowed to proceed for about four hours.

The halogenated compound (15) is then coupled with an appropriately substituted phenyl oxazole in a Mitsunobu reaction to prepare (16) followed by displacement of the halogen with an amine of the formula $NR^7R^8$ in a polar aprotic solvent such as dimethylformamide at about 80° C. for about five hours to prepare the desired final product.

Scheme I(d)

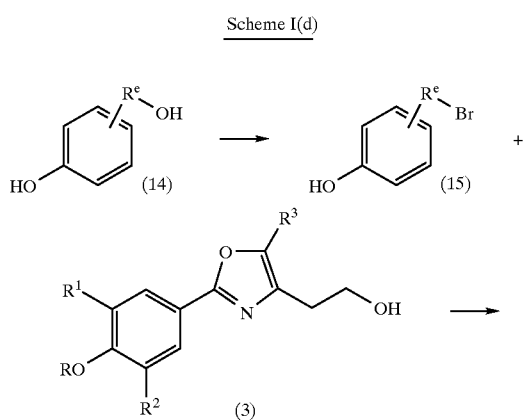

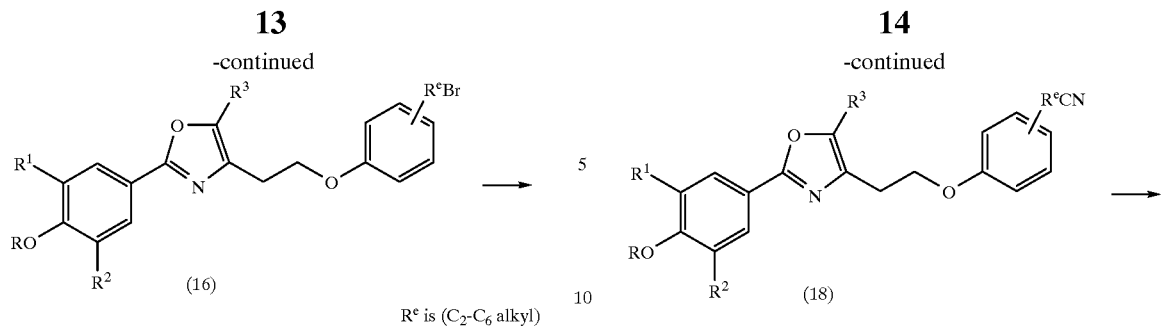

Scheme I(e) below describes a third procedure for preparing compounds of formula I where Ar is phenyl substituted with one or two straight chain $(C_2-C_6 \text{ alkyl})R^6$ groups.

In a Mitsunobu reaction, compound (17) is first coupled with an appropriately substituted phenyl oxazole to form the intermediate oxazole (18). Reduction of the cyano group followed by hydrolysis prepares compound (19). Amination of compound (19) is achieved by either method described in Scheme I(a), step (e).

Compounds of formula I where Ar is phenyl substituted with one or two $$\overset{O}{\underset{\|}{C}}(CH_2)_n R^6$$

groups, and X and Y are as defined in Scheme I(a–e) above can be prepared as outlined in Scheme II below.

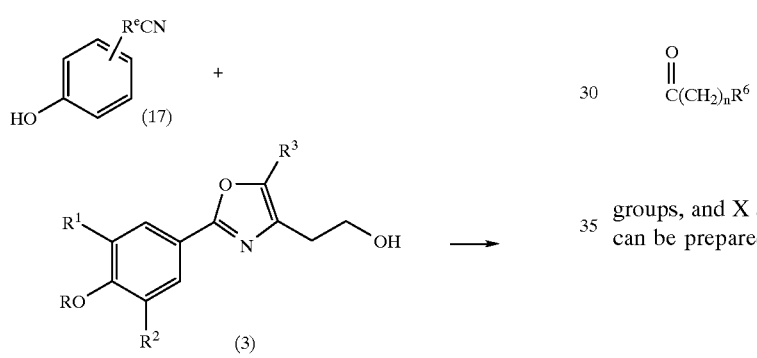

Scheme I(e)

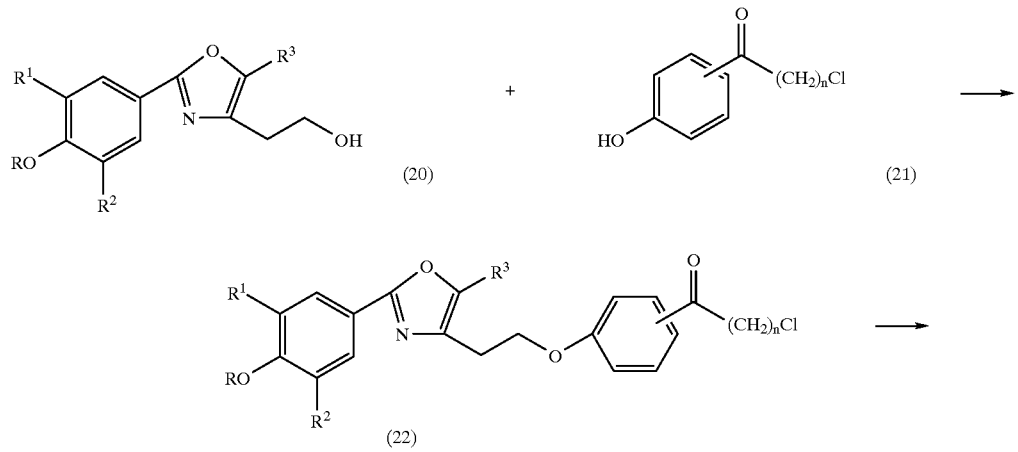

Scheme II

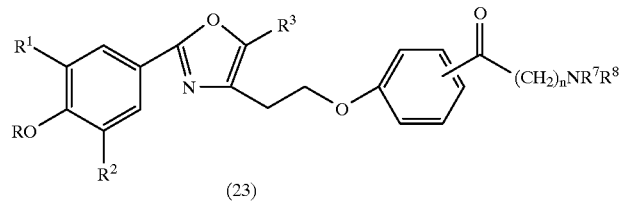

(23)

In the above reaction Scheme II, an appropriately substituted phenyl oxazole (20), dissolved in an aprotic polar solvent such as tetrahydrofuran, is coupled with an appropriately substituted phenol (21) in a Mitsunobu reaction to form (22). At ambient temperatures, the reaction is substantially complete in 5 hours. Compound (22) is then treated with sodium iodide to form the iodoketone which is then displaced using an appropriately substituted amine while heating to about 50° C.–80° C. The amination can be conducted in a non-polar organic solvent such as toluene and is substantially complete in about three hours.

Compounds of formula I where Ar is phenyl substituted with one or two branched ($C_1$–$C_6$ alkyl)$R^6$ groups, and X and Y are as described in Scheme I(a–e) above can be prepared according to Scheme III below.

Scheme III

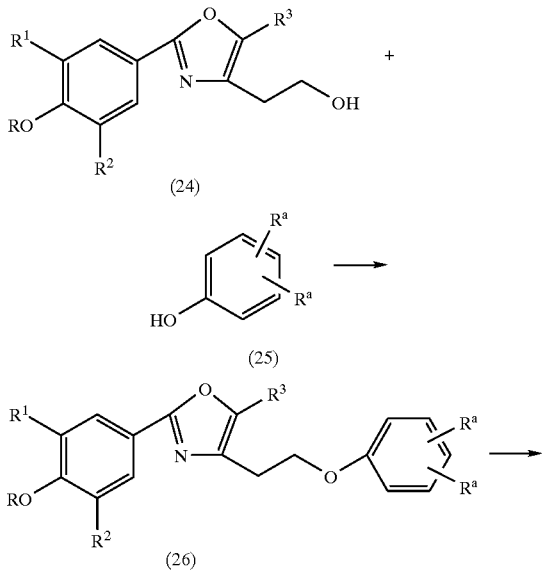

$R^a$ is oxo substituted ($C_1$-$C_6$) alkyl

An appropriately substituted phenyloxazole (24), dissolved in an aprotic polar solvent such as tetrahydrofuran, is coupled with an appropriately substituted ketone (25) in a Mitsunobu reaction to form compound (26). Reductive amination of (26) can be achieved by either of the methods described in Scheme I(a), step (e).

Compounds of Schemes I, II or III wherein Ar is phenyl additionally substituted with one or two substituents selected from $C_1$–$C_6$ alkyl, halo and hydroxy can be prepared as shown in Scheme IV below.

Scheme IV

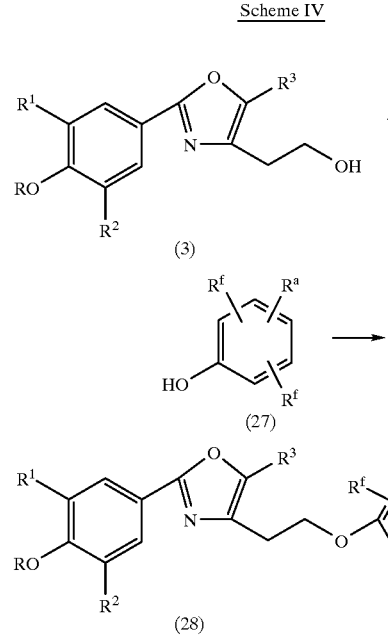

$R^a$ is oxo-substituted $C_1$-$C_6$ alkyl
$R^f$ is hydrogen, $C_1$-$C_6$ alkyl, halo or protected hydrox An appropriately substituted phenyl oxazole and appropriately substituted phenol (27) are coupled in a Mitsunobu reaction as described in Scheme I(a), step (d), to form the intermediate compound (28) which can then be aminated using either of the two methods described in Scheme I(a), step (e). The hydroxy may then be deprotected where appropriate.

Compounds of Schemes I, II or III where Ar is phenyl substituted with two substituents which, when taken together, form a phenyl ring can be prepared as shown in Scheme V below.

Scheme V

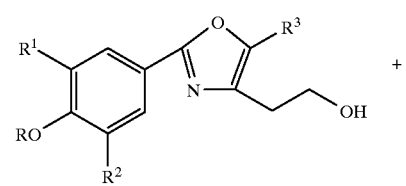

-continued

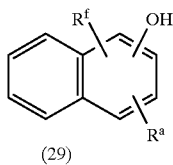
(29)

R$^a$ is oxo-substituted C$_1$-C$_6$ alkyl
R$^f$ is hydrogen, C$_1$-C$_6$ alkyl, halo or protected hydrox Using a Mitsunobu coupling, a phenyloxazole starting material is reacted with an appropriately substituted hydroxynaphthaldehyde (29). The resulting product can then be subjected to reductive amination using either method of Scheme I, step (e) and the hydroxy deprotected where appropriate.

Compounds of Schemes I, II or III where Ar is phenyl substituted with

and/or (C$_1$–C$_6$ alkyl)R$^6$; where R$^6$ is morpholin-1-yl, piperazin-1-yl, thiomorpholin-1-yl or substituted piperazin-1-yl are prepared according to reaction Scheme VI.

Scheme VI

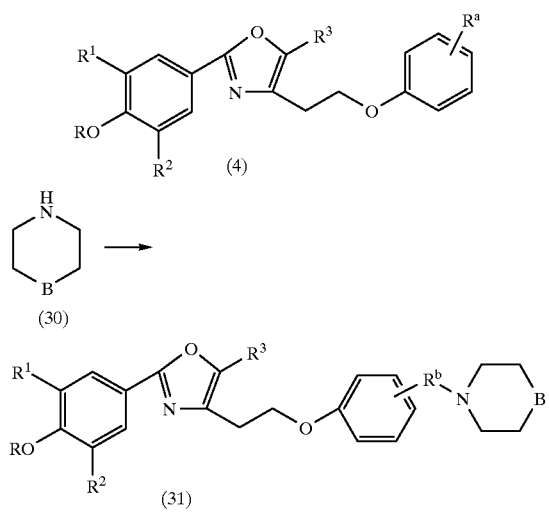

An appropriately substituted starting material (30) is coupled by reductive amination with an appropriately substituted phenyloxazole according to the reactions of Scheme I(a), Step (e), i.e., using either a reducing agent such as sodium cyanoborohydride in an aprotic polar solvent such as tetrahydrofuran, or titanium IV isopropoxide (Ti(OiPr)$_4$) and sodium borohydride in a low molecular weight alcohol such as ethanol to form (31).

Compounds of Formula I where R$^6$ is piperazin-1-yl can be prepared by treating compound (31) of Scheme VI, where B is

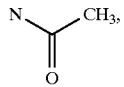

with an excess of an inorganic acid such as hydrochloric acid.

Compounds of formula I where R$^6$ is imidazol-1-yl are prepared according to the following Scheme VII.

Scheme VII

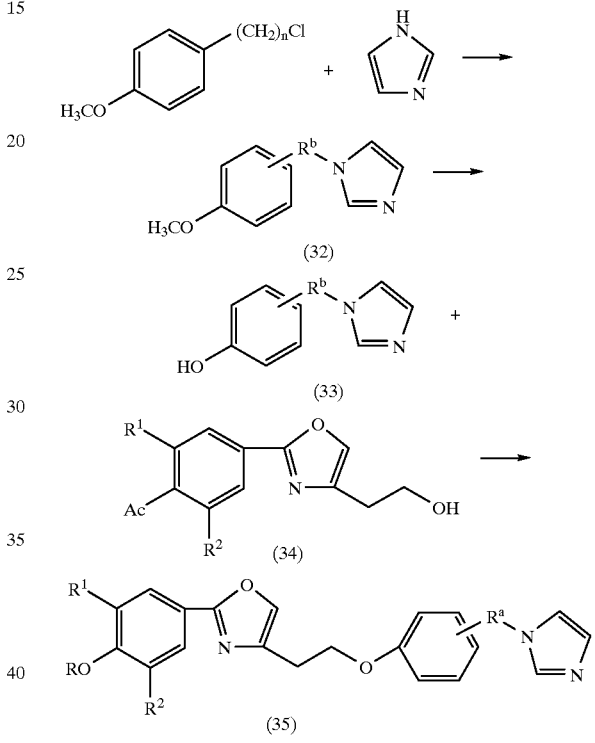

R$^b$ is C$_1$-C$_6$ alkyl.

A methoxyphenylalkylchloride such as p-Methoxybenzyl chloride is refluxed with imidazole to form (32). The reaction, conducted in a polar organic solvent such as acetonitrile, is substantially complete in about 16 hours. Demethylation of (32) is achieved by treatment with an agent, such as boron tribromide, to form compound (33). In a Mitsunobu coupling, compound (33) can be coupled with the phenyloxazole (34) to form the desired product (35).

Compounds of formula I where R$^6$ is 4,5-dihydro-1-H-imidazol-2-yl are prepared according to Scheme VIII.

Scheme VIII

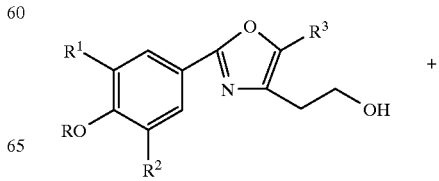

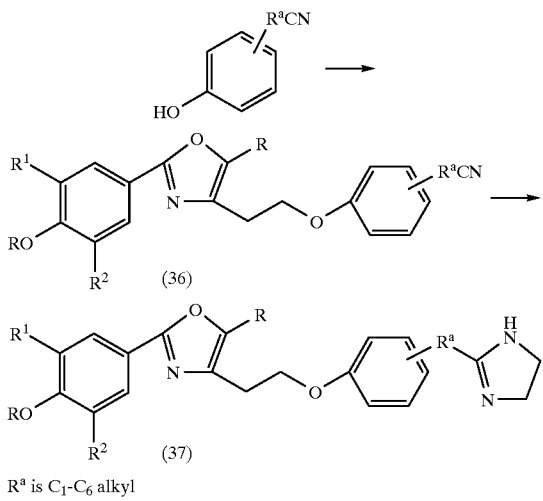

$R^a$ is $C_1$-$C_6$ alkyl

A phenyloxazole starting material is coupled with a hydroxyphenylalkyl cyanide compound in a Mitsunobu reaction. Cyclization of the cyano group to form the dihydroimidazole (37) can be achieved by first, treating (36) with hydrogen chloride gas in ethanol at low temperatures for about four hours then refluxing with ethylenediamine for an additional period of up to 32 hours.

Compounds of formula I where Ar is phenyl substituted with two substituents which when taken together with the carbons to which they are attached form a pyridyl or tetrahydropyridyl can be prepared according to Schemes IX(a) and IX(b) below.

Scheme IX(a)

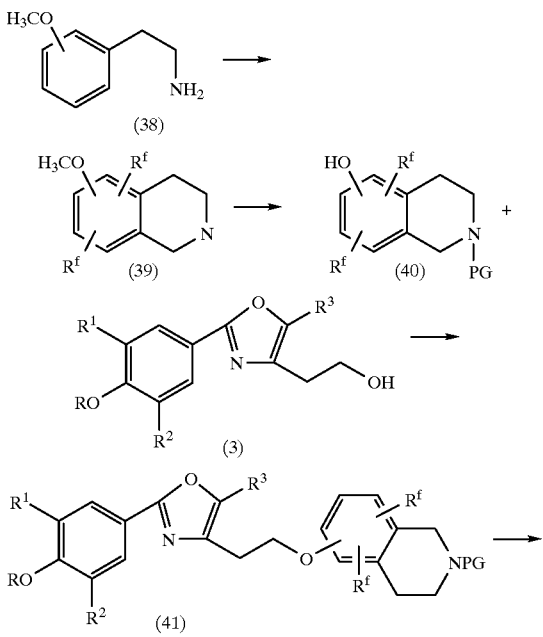

PG is a protecting group.
$R^f$ is hydrogen, $C_1$-$C_6$ alkyl halo or protected hydroxy.

Scheme IX(b)

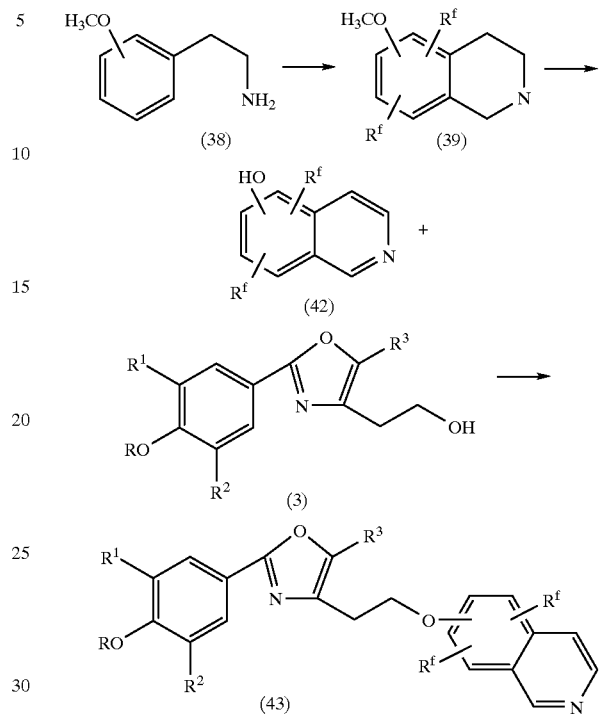

$R^f$ is hydrogen, $C_1$-$C_6$ alkyl, halo or protected hydroxy.

In the above reaction Schemes IX(a) and IX(b), starting material (38) is cyclized with the appropriate aldehyde in an acid solution to form intermediate (39) as an oxalate salt.

In Scheme IX(a), intermediate (39) can first be demethylated by refluxing the oxalate salt (38) with hydrogen bromide then protecting the nitrogen with an amino-protecting agent such as di-tert-butyl dicarbonate to prepare (40).

In Scheme IX(b), the free amine (39) can be aromatized in the presence of dehydrogenating reagent by heating with palladium black followed by demethylation, as discussed above, to form (42).

Compounds (40) or (42) can then be coupled with an appropriately substituted phenyloxazole in a Mitsunobu reaction, to form the desired products (41) or (43). Removal of the nitrogen protecting group can be achieved by standard methodology such as by treatment with trifluoroacetic acid and an appropriate t-butyl cation scavenger such as thiophenol. If a hydroxy protecting group is employed, the hydroxy group may be deprotected by, for example, hydrolysis or treatment with an acid depending on the protecting group selected.

Compounds where Ar is substituted pyridyl can be achieved by the following general reaction Scheme X Scheme X

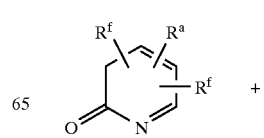

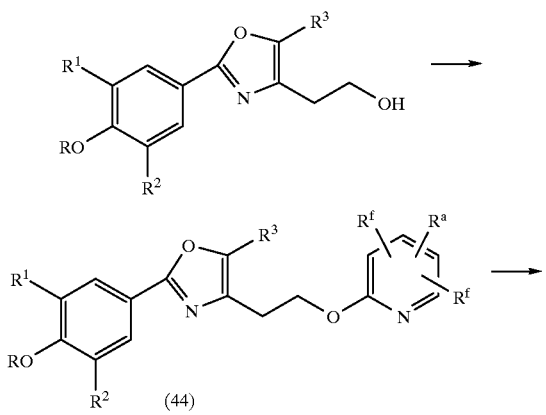

R<sup>a</sup> is oxo-substituted $C_1$–$C_6$ alkyl
R<sup>f</sup> is hydrogen, $C_1$–$C_6$ alkyl, halo or protected hydroxy Using an appropriately substituted pyridone carboxaldehyde and an appropriately substituted phenyloxazole in a Mitsunobu coupling reaction, compound (44) is prepared. When R<sup>f</sup> is a protected hydroxy group, it may be deprotected after the coupling step. Compound (44) can then undergo reductive amination using either process described in Scheme I(a), step (e) above.

Compounds of formula I where Y is sulfur can be prepared as illustrated in Scheme XI below.

Scheme XI

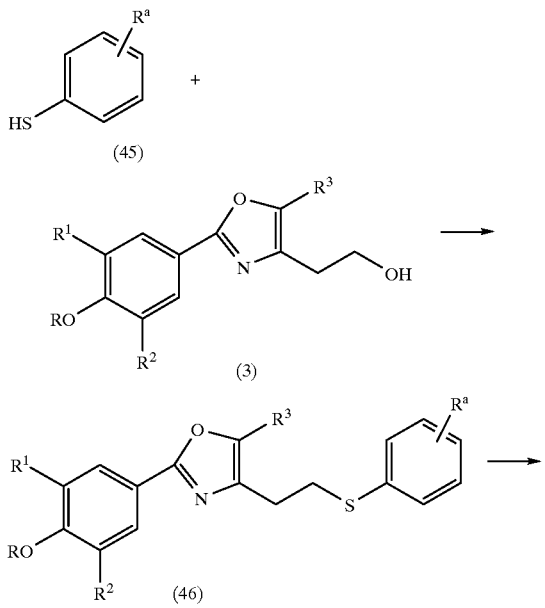

R<sup>a</sup> is oxo-substituted $C_1$–$C_6$ alkyl

An appropriately substituted phenyloxazole is coupled with an appropriately substituted mercaptobenzaldehyde (45) in a Mitsunobu reaction. The resultant intermediate (46) can then be reduced to the desired amine using either of the reductive amination reactions described in Scheme I(a), step (e).

Compounds of formula I where $R^3$ is $C_1$–$C_6$ alkyl and R, $R^1$, $R^2$, $R^4$, X and Y are as described above can be prepared as follows:

Scheme XII

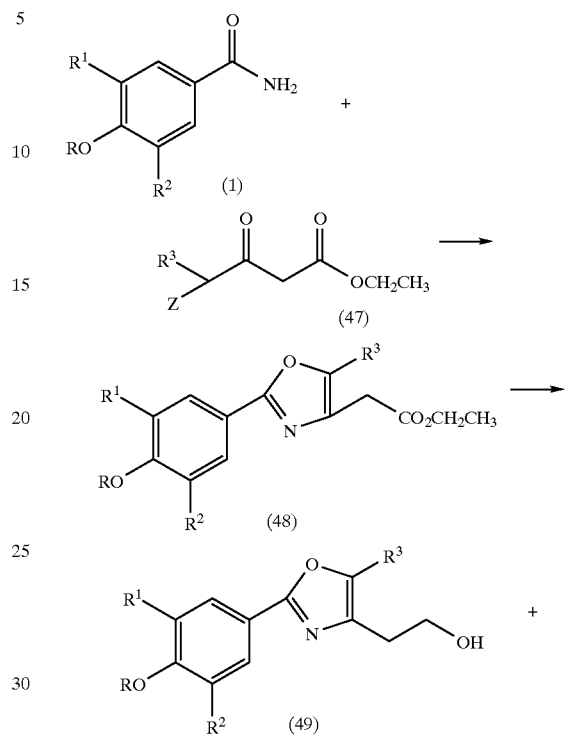

Z is a halogen
R<sup>a</sup> is oxo-substituted $C_1$–$C_6$ alkyl

Potassium ethyl malonate is stirred with a metal halide, such as magnesium chloride and a base, such as triethylamine, in an aprotic polar solvent such as acetonitrile under an inert gas such as nitrogen at ambient temperatures then reacted with an acid halide such as μ-chloro-propionyl chloride to form starting halide (47).

Intermediate (48) is formed by reacting the halide (47) with an appropriately substituted benzamide (1), prepared as described in Scheme I(a) above. The reaction is allowed to proceed at temperatures of about 100° to 150° C. under an inert gas such as nitrogen for about 1 to 8 hours.

Reduction of intermediate (48) with a reducing agent such as lithium aluminum hydride affords compound (49). The reduction is conducted under an inert gas such as nitrogen in an aprotic polar solvent or ether such as tetrahydrofuran for a period of from 1–24 hours.

Using a Mitsunobu coupling, an appropriately substituted benzaldehyde is combined with intermediate (49) to form compound (50) which can then be reduced by reductive amination as described in Scheme I(a), step e, above to form the desired product.

Compounds of formula I where X is S can be prepared as follows:

Scheme XIII

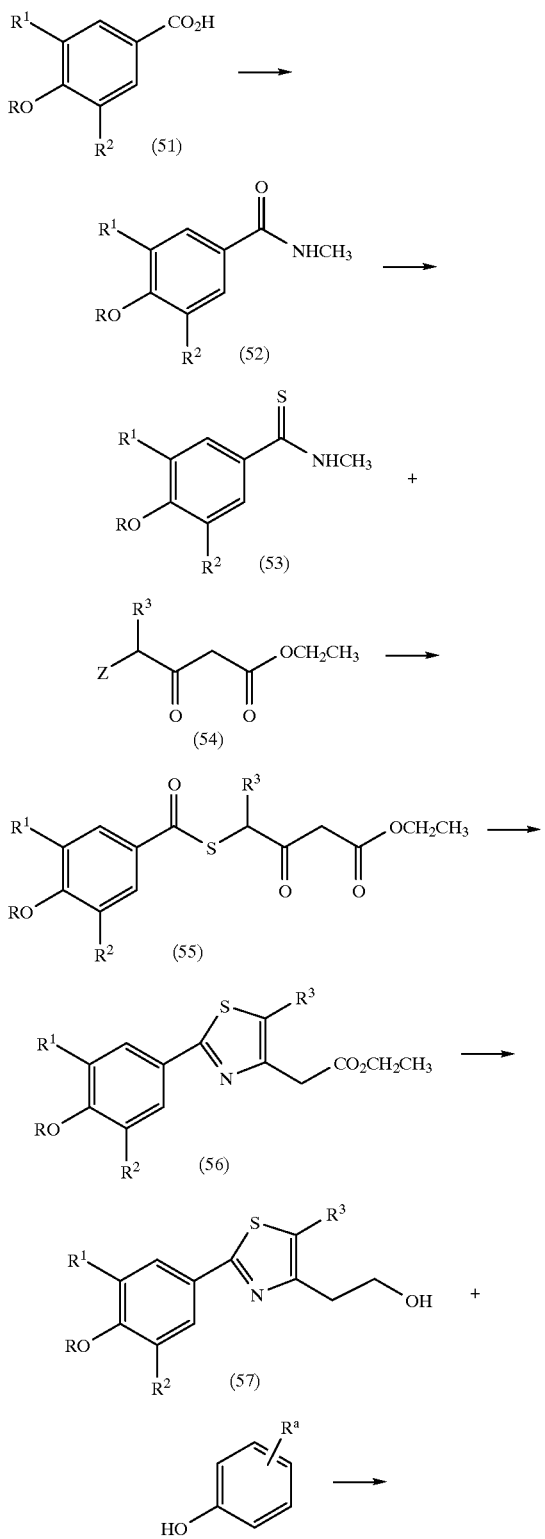

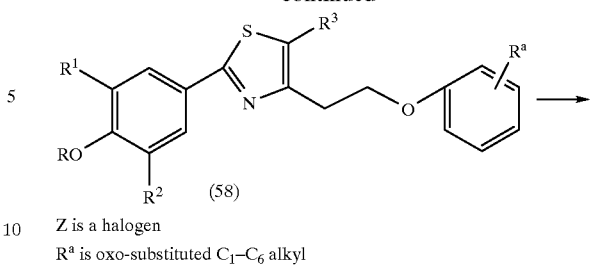

Z is a halogen
$R^a$ is oxo-substituted $C_1$–$C_6$ alkyl

Benzamide (52) is prepared by refluxing an appropriately substituted benzoic acid with an activating agent such as carbonyldiimidazole under an inert gas such as nitrogen, then reacting with methylamine as described in Scheme I, Step (a) above. Using an aprotic polar solvent such as tetrahydrofuran, the reaction is substantially complete in about 2–24 hours.

Conversion to the thiobenzamide (53) is achieved by reacting (52) with Lawessens reagent at temperatures of from 80° C. to 120° C. in an organic solvent such as hexamethylphosphoramide under an inert gas such as nitrogen for about 1 to 2 hours.

The synthesis of intermediate (55) is accomplished by refluxing the thioamide (53) under an inert gas such as nitrogen with an $\mu$-haloketone such as ethyl 4-chloroacetoacetate in the presence of potassium iodide. An aprotic polar solvent or ether such as tetrahydrofuran is preferred and the reaction is complete within 1 to 6 hours.

Cyclization to prepare the thiazole (56) is achieved by reacting thioester (55) with an excess of ammonium acetate in acid such as acetic acid under an inert gas such as nitrogen for from 1 to 5 hours.

Reduction of the thiazole ester (56) is accomplished with a reducing agent such as lithium aluminum hydride. The reduction is preferably conducted under an inert gas such as nitrogen in an aprotic polar solvent such as tetrahydrofuran. The reaction is substantially complete in 1 to 2 hours.

Using a Mitsunobu reaction, the thiazole intermediate (57) can be coupled with an appropriately substituted benzaldehyde to form (58) which can be isolated and purified and reduced to the desired amine by reductive amination as described in Scheme I(a), step (e) above.

Compounds of formula I where Y is $CHR^5$, where $R^4$ and $R^5$ are individually hydrogen or $R^4$ and $R^5$ taken together form a bond can be prepared according to Scheme XIV as follows.

Scheme XIV

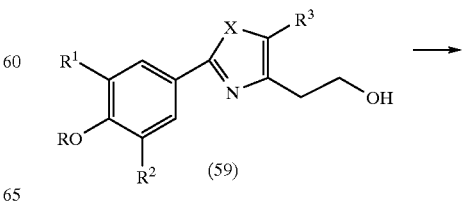

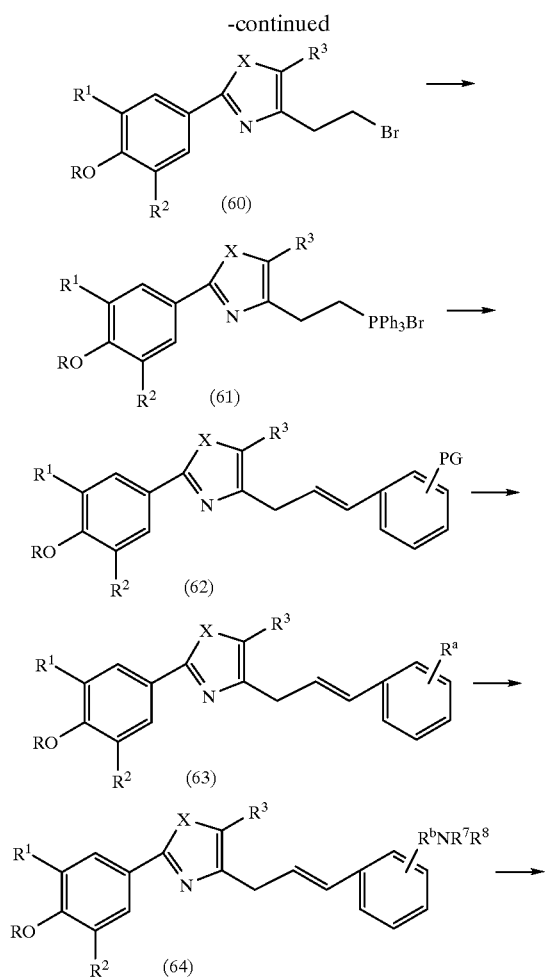

$R^a$ is oxo-substituted $C_1$–$C_6$ alkyl
$R^b$ is $C_1$–$C_6$ alkyl
PG is a protected aldehyde At ambient temperature, in a polar solvent such as methylene chloride, an appropriately substituted starting alcohol (59) is halogenated by treatment with a halogenating agent such as triphenylphosphine and bromine in the presence of a base or acid scavenger such as imidazole. The reaction is substantially complete in 1–24 hours.

In a displacement reaction, the halogenated compound (60) is refluxed with triphenylphosphine in a nonpolar solvent such as xylene for about 24 hours to form the activated intermediate (61).

Intermediate (62) is prepared in a Wittig reaction using a strong base such as sodium hexamethyldisilazane and an appropriately protected aldehyde such as terephthalaldehyde mono-(diethylacetal). The reaction is preferably conducted in an aprotic polar solvent such as tetrahydrofuran at temperatures of from about −20° C. to about 0° C. and is substantially complete in about 3 to 10 hours.

It will be readily appreciated by the skilled artisan that intermediate (62) forms the E and Z isomers which may be readily separated by conventional chromatographic techniques.

The desired aldehyde (63) may then be deprotected by treatment with an aqueous acid such as hydrochloric acid for about 24 hours. Deprotection is preferably conducted in a polar solvent or ether such as diethylether at ambient temperature.

Reductive amination can be accomplished using either of the procedures described in Scheme I(a), Step (e).

Compounds of formula I where Y is $CHR^5$ and $R^5$ is hydrogen can be prepared by hydrogenation of compound (64) with hydrogen gas and 5% palladium on carbon. The reduction is preferably conducted in a non-polar solvent such as toluene at ambient temperatures and is substantially complete in about four hours.

Compounds of formula I where Ar, X and Y and $R^4$ are as defined as in Scheme I(a) above, and m=0 can be prepared as demonstrated in Scheme XV below.

Scheme XV

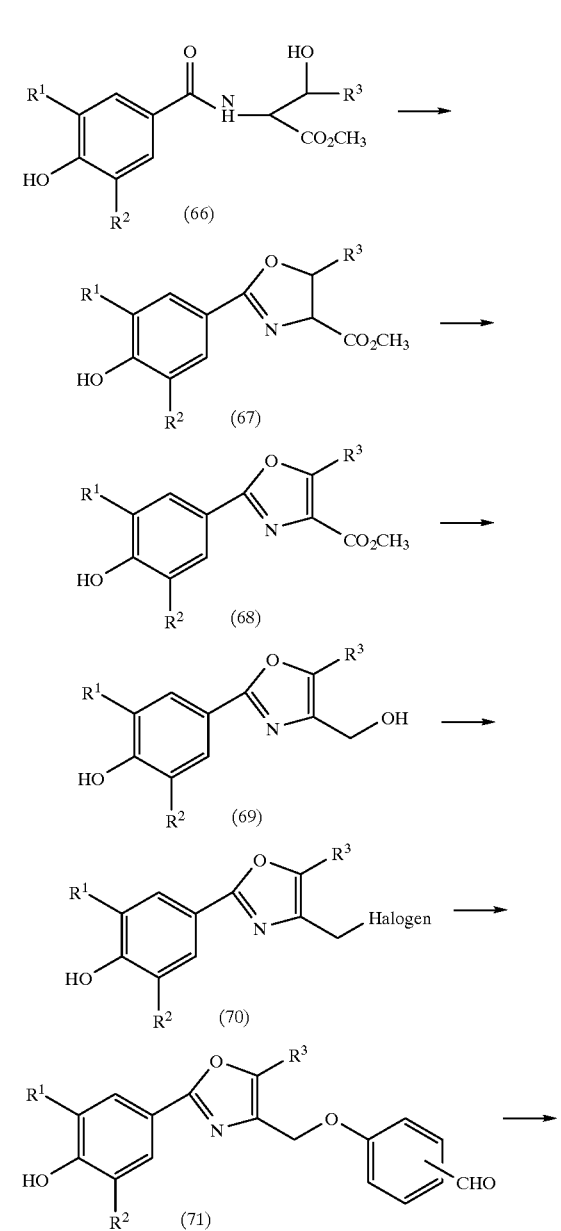

Starting material (66) is achieved by treating an appropriately substituted benzoic acid with a peptide coupling reagent, such as 1,1'-carbonyldiimidazole, to form an activated acylating agent then reacting with an appropriately substituted serine compound.

The methyl ester (66) is cyclized to the oxazoline (67) by reacting with a brominating agent, such as triphenylphosphine, and carbon tetrabromide in the presence of a base.

The reaction can be conducted in an aprotic polar solvent, such as acetonitrile, at ambient temperature for from about 1 to 24 hours.

The oxazoline (67) is oxidized to compound (68) by treatment with an oxidizing agent, such as activated manganese oxide, at a temperature of about 20° to 50° C. for about 1 to 24 hours in an organic solvent such as acetone.

The oxazole (68) can then be reduced with a reducing agent, such as lithium borohydride-methanol reducing system in an aprotic polar solvent, such as tetrahydrofuran. Preferably, the reaction is initiated at ambient temperatures and then refluxed for from 30 minutes to 12 hours.

Halogenation of (69) is accomplished by treatment with a halogenating agent such as triphenylphosphine and carbon tetrabromide in an aprotic polar solvent such as acetonitrile. The reaction can be conducted at ambient temperatures for from 1–24 hours.

In a displacement reaction under Finkelstein conditions, the halogen is replaced with an appropriately substituted benzaldehyde.

Reductive amination of (70) as described in Scheme I(a), Step (e), above yields the desired product (71).

The intermediates and final products may be isolated and purified by conventional techniques, for example by concentration of the solvents, followed by washing of the residue with water, then purification by conventional techniques such as chromatography or recrystallization.

When Ar is phenyl substituted with one or two ($C_1$–$C_6$ alkyl)$R^6$ groups, the present invention may have one or two stereo centers. The methods, formulations and compounds of the present invention encompass the diastereomers and the racemates and their individual stereo isomers. Diastereomeric pairs may be obtained according to procedures well known in the art. For example, formation of a diastereomeric salt from a racemic amine can be accomplished by treatment with a chiral acid, such as tartaric acid or diisopropylidene-keto-gulonic acid.

It will be readily appreciated by the skilled artisan that the substituted benzoic acid, amide, amine, alcohol, aldehyde, heterocyclic, imidazole and thiophenol starting materials are either commercially available or can be readily prepared by known techniques from commercially available starting materials. All other reactants used to prepare the compounds in the instant invention are commercially available.

The following examples further illustrate the preparation of the compounds of this invention. The examples are illustrative only and are not intended to limit the scope of the invention in any way.

EXAMPLE 1

2-(3,5-di-t-butyl-4-hydroxyphenyl)-4-(2-(4-ethylaminomethylphenoxy)ethyl)oxazole hydrochloride dihydrate A. Preparation of 3,5-bis(1,1-dimethylethyl)-4-hydroxybenzamide In a 22 L Morton flask, 749 g (3.0 mol) of 3,5-bis(1,1-dimethylethyl)-4-hydroxybenzoic acid, 533 g (3.3 mol) carbonyldiimidazole and tetrahydrofuran (THF) were combined and heated slowly to reflux and allowed to reflux for 2.5 hours. The reaction mixture was cooled to 26° C. and concentrated aqueous ammonia was added. Stirring was continued for 2 hours and the reaction mixture was allowed to stand overnight. The contents were transferred to a flask and rinsed with tetrahydrofuran (250 mL). The mixture was stirred, layers were separated, and the aqueous layer was saved. The organic layer was washed with brine (2.5 L) followed by brine/deionized (DI) water (1 L/1.5 L). The organic layer was washed with 9.7 M hydrochloric acid (HCl)/deionized water (0.25 L / 2.25 L), followed by 9.7 M hydrochloric acid/deionized water (0.5 L/2.8 L), and 9.7 M hydrochloric acid/deionized water/brine (0.5 L/1.5 L/1.5 L). The organic layer was set aside while the combined aqueous layers were washed with tetrahydrofuran. The combined organic layers were washed with brine, dried with sodium sulfate (855 g) and filtered. The filtrate was evaporated to 1011 g of a wet (water), white solid. Methylene chloride was added and removed in vacuo. This procedure was repeated with ethyl acetate (6 L, then 2 L) to produce a solid residue (779 g). The residue was slurried in ethyl acetate and heptane, filtered, and dried in a vacuum oven to yield the desired amide (736 g, 98.7%) as a white solid mp 257–260° C.

$^1$H NMR (DMSO-$d_6$, 300 MHz) δ 7.75 (1H, s), 7.60 (2H, s), 7.30 (1H, s), 7.00 (1H, s), 1.35 (18H, s).

B. Preparation of 2-(3,5-di-t-butyl-4-hydroxyphenyl)-4-(carboxymethyl)oxazole

To 24.90 g (100 mmol) of the compound of step A, 55 mL (407 mmol) of ethyl 4-chloroacetoacetate was added. The mixture was heated to 130° C. under nitrogen for 2 hours. The reaction mixture was cooled to 90° C. and the volatiles were distilled from the reaction mixture under vacuum until the pot temperature reached 130° C. The thick residue was allowed to cool to 60° C. under vacuum. The vacuum was released and 100 mL of methanol was added to the mixture. The solution was cooled to 25° C. and then 50% sodium hydroxide solution (50 mL) was added dropwise. The reaction mixture temperature increased to 55° C. The mixture was stirred 25 minutes, then concentrated aqueous hydrochloric acid (25 mL, 300 mmol) was added dropwise to the reaction mixture to bring the pH to 7–8. The mixture was filtered and the cake was washed with methanol (2×50 mL). The methanol was removed under vacuum, and then 1N hydrochloric acid (100 mL) and water (100 mL) were added. A gummy precipitate formed. The precipitate was dissolved by adding 500 mL of a 1:1 mixture of tert-butyl methyl ether (MTBE) and ethyl acetate. The resulting emulsion separated into three layers overnight. The upper layer, containing desired product by HPLC, was dried with sodium sulfate and concentrated in vacuo to give 30.8 g of a tan solid. This solid was dissolved in 2:1 methanol:water (225 mL) at 75° C. The stirred mixture was allowed to cool to 25° C. over 1 hour, and stirred for another 2.5 hours. The mixture was filtered and the cake was washed with a total of 120 mL of 2:1 methanol:water. Vacuum drying at 40° C. gave 21.94 g of the subtitled product. A 19.9 g portion of the acid was recrystallized from 300 mL of 1:1 heptane:toluene to give 17.77 g (62% overall yield) of the subtitled product as a white solid.

mp 166–68° C.

$^1$H NMR (DMSO d-6, 300 MHz) δ 12.49 (s, 1H, exchanges with $D_2O$), 7.93 (s, 1H,), 7.72 (s, 2H), 7.54 (s, 1H, exchanges with $D_2O$), 3.56 (s, 2H), 1.41 (s, 18H).

Elemental analysis for $C_{19}H_{25}NO_4$: Calculated: C, 68.86; H, 7.60; N, 4.23. Found: C, 68.86; H, 7.59; N, 4.32.

FDMS 331 ($M^+$).

C. Preparation of 2-(3,5-di-t-butyl-4-hydroxyphenyl)-4-(2-hydroxyethyl)oxazole

In a 22 L flask, 757 g (2.28 mol) of the compound of step B was dissolved in tetrahydrofuran. To the solution was added, very slowly at first and with water-bath cooling, 1 M borane tetrahydrofuran (4.8 L). After 1 hour the reaction mixture was quenched with methanol (650 mL) very slowly due to hydrogen evolution. The mixture was allowed to stir overnight. The solution was placed on a rotary evaporator and evaporated to a foam (995 g). The residue was dissolved in tert-butyl methyl ether (11 L) and deionized water (4.9 L) and 50% sodium hydroxide (130 mL) were added and stirred then brine was added (3.6 L). Layers were allowed to separate yielding three layers. The lower two layers showed no product so they were discarded. The tert-butyl methyl ether layer was washed with a mixture of 1 N sodium hydroxide (100 mL), deionized water (2 L), and brine (2 L). The organic layer was dried with sodium sulfate, filtered and evaporated to give 802 g of viscous residue. Toluene (1.4 L) was added to the residue and the mixture was heated to 80° C. to obtain a solution. Heptane (6 L) was added, the solution was heated to 93° C., and then cooled over 1.5 h to 0–10° C. with an ice bath. The mixture was filtered and the cake was rinsed with 60:40 heptane/toluene (2 L). The solid was dried in a vacuum oven to yield 670 g of subtitled product. The solids were recrystallized from toluene (2 L) and heptane (5.5 L) to yield 627 g (87% yield) of product as a white solid.

mp 119.5–21° C.

$^1$H NMR (CDC$_3$, 300 MHz) δ 1.48 (s, 18H), 2.8 (t, J=6.0 Hz, 2H), 3.97 (t, J=6.0 Hz, 2H), 5.52 (s, 1H), 7.42 (s, 1H), 7.82 (s, 2H).

D. Preparation of 2-(3,5-di-t-butyl-4-hydroxyphenyl)-4-(2-(4-formylphenyloxy)ethyl)oxazole The compound of step C (204.3 g, 644 mmol), triethylamine (100 mL, 716 mmol) and methylene chloride (1.7 L) were stirred to give a solution. Methanesulfonyl chloride (81.3 g, 710 mmol) was added over 15 minutes and a water bath was used to keep the pot temperature below 31° C. The reaction mixture was stirred and allowed to cool to 23° C. over 1.5 hours. The reaction mixture was poured into a 4 L separatory funnel and the flask was rinsed with methylene chloride (0.5 L). The organic layer was washed with 1 N hydrochloric acid (3×1 L) and the combined aqueous layers were back-extracted with methylene chloride (0.3 L). The combined organic layers and washed with a solution of brine (0.5 L) and deionized water (0.5 L). The organic layers were dried with sodium sulfate, filtered and evaporated to give 254 g of the mesylate as an oily foam. To the intermediate mesylate compound was added dimethyl sulfoxide (DMSO, 0.7 L) and a solution was obtained. In a separate flask, 4-hydroxybenzaldehyde (89.6 g, 734 mmol), potassium t-butoxide (79.98 g, 0.713 mmol) and dimethyl sulfoxide (1.2 L) were combined and heated to 45° C. to yield a brown solution. The mesylate compound in dimethyl sulfoxide was added all at once. The reaction mixture was heated at 60–65° C. for 15 hours An additional 0.5 L of dimethyl sulfoxide was added. The reaction temperature was increased to 70° C. and held there for 2 hours. Then, 4-hydroxybenzaldehyde (3.92 g) and potassium t-butoxide (3.59 g) were added to the reaction mixture. After 7 hours at 70° C. the reaction mixture was allowed to cool to ambient temperature. Tert-butyl methyl ether (3.3 L) was added to the reaction mixture. The solution was extracted with 1 N sodium hydroxide (4×2 L). The aqueous layers were combined, back extracted with tert-butyl methyl ether (2×1 L) and then discarded. The combined organic layers were washed with deionized water (2 L), deionized water/brine (2 L), and brine (2 L). The organic layer was dried with sodium sulfate, filtered and evaporated to give a dark residue (267.3 g). The residue was dissolved in a mixture of methylene chloride (150 mL) and heptane (100 mL) and passed through a chromatography unit with a silica gel (2.5 kg) column. The column was eluted with 1:1 heptane/methylene chloride (16 L), methylene chloride (12 L), and 6% ethyl acetate/methylene chloride. Fractions containing the product as the major component were combined and evaporated to give 196 g of an amber oil. The oil was dissolved in chloroform (200 mL), and transferred to a flask with a mechanical stirrer. The flask was rinsed with hexanes/chloroform (100 mL/25 mL) and hexanes (100 mL) and the washes were added to the solution. After adding hexanes (1.8 L), the solution was heated to reflux and 100 mL of distillate was collected. The mixture was cooled to 35° C. over 1.5 hours and then crystallization occurred. Using an ice/water bath, the solution was cooled to 6° C. over 1.5 hours. The product was filtered, rinsed with 10% chloroform/hexanes (300 mL), and dried in a vacuum oven to obtain 153 g (56% yield) of subtitled product as a white solid.

mp 110–112° C.

HPLC assay showed 99.4% (by area) desired compound.

$^1$H NMR (CDCl$_3$, 300 MHz) δ 1.45 (s, 18H), 3.10 (t, 2H, J=6 Hz), 4.38 (t, 2H, J=6 Hz), 5.50 (s, 1H), 7.02 (d, J=7 Hz, 2H), 7.50 (s, 1H), 7.79 (d, J=7 Hz, 2H), 7.82 (s, 2H), 9.85 (s, 1H).

E. Preparation of 2-(3,5-di-t-butyl-4-hydroxyphenyl)-4-(2-(4-ethylaminomethylphenoxy)ethyl)oxazole hydrochloride hemihydrate To 5.05 g (12 mmole) of the compound of step D dissolved in 50 ml. of dry methanol under nitrogen was added 7.85 ml (120 mmole) of monoethylamine. The solution was stirred for 5 minutes then 6.8 ml (120 mmole) of acetic acid was added and the mixture was stirred under nitrogen for 30 minutes. Sodium cyanoborohydride, 795 mg (12.6 mmole) was added and the reaction was stirred for 3 hours. An additional 500 mg of sodium cyanoborohydride was added and again stirred for an additional hour. Ethyl acetate was then added and the mixture was washed with water, saturated sodium bicarbonate and again with water. The organic layer was dried, filtered then evaporated to give 5.44 g of crude product which was chromatographed on 300 ml. silica, eluting with methylene chloride/methanol/concentrated ammonia (90:10:1). Fractions containing the desired product were concentrated under vacuum then dissolved in diethyl ether. Hydrogen chloride gas was bubbled through the solution to provide an oil which was dissolved in acetone and stripped to dryness to give 3.4 g (54%) of title product as a white foam.

FDMS-M$^+$ 450;

Elemental analysis for (C$_{28}$H$_{38}$N$_2$O$_3$.HCl.0.5H$_2$O) Calculated: C, 67.79; H, 8.13; N, 5.65 Found: C, 67.97; H, 7.99; N, 5.74

NMR (CDC$_3$), δ 1.40 (t, 3H, J=7 Hz), 1.49 (S, 18H), 2.92 (q, 2H, J=4 Hz), 3.30 (t, 2H, J=7 Hz), 3.95 (t, 2H, J=7 Hz), 4.31 (t, 2H, J=7 Hz), 6.10 (bs, 1H), 6.85 (d, 2H, J=9 Hz), 7.49 (d, 2H, J=9 Hz), 7.87 (s, 1H), 8.21 (s, 2H), 9.59 (bs, 2H)

EXAMPLE 2

2-(3,5-di-t-butyl-4-hydroxyphenyl)-4-(2-(4-dimethylaminomethyl-phenoxy)ethyl)oxazole hydrochloride Title compound was prepared from 1.26 g (3 mmole) of the compound of Example 1D substantially in accordance with the procedure in Example 1E above using 200 mg (3.15 mmole) of sodium cyanoborohydride and 3.37 ml (30 mmole) of 40% aqueous dimethylamine. Such reaction provided 1.31 g (90%) of the title product as a white foam.

FDMS-M$^+$ 450;

Elemental analysis for (C$_{28}$H$_{38}$N$_2$O$_3$.HCl) Calculated: C, 69.05; H, 8.07; N, 5.75 Found: C, 68.75; H, 7.94; H, 5.56

NMR (CDC$_3$), δ 1.49 (s, 18H), 2.71 (d, 2H, J=3 Hz), 3.38 (t, 2H, J=7 Hz), 4.10 (d, 2H, J=7 Hz), 4.44 (t, 2H, J=7 Hz), 6.08 (s, 1H), 6.95 (d, 2H, J=9 Hz), 7.50 (d, 2H, J=9 Hz), 7.74 (s, 1H), 8.23 (s, 2H)

EXAMPLE 3

2-(3,5-di-t-butyl-4-hydroxyphenyl)-4-(2-(4-methylethylaminomethylphenoxy)ethyl)oxazole hydrochloride hydrate Title compound was prepared from 3.36 g (7.98 mmole) of the compound of Example 1D substantially in accordance with the procedure in Example 1E above using 0.5 g (7.98 mmole) of sodium cyanoborohydride and 6.9 ml (79.8 mmole) of methylethylamine. The organic layer was chromatographed on silica gel using a methylene chloride/methanol gradient to give the free base (2.79 g, 75%). The free base was dissolved in methylene chloride, treated with hydrogen chloride gas and evaporated to give 2.8 g (93%) of the title product.

$^1$H NMR (CDC$_3$) δ 8.0 (s, 2H), 7.6 (s, 1H), 7.5 (d, J=9 Hz, 2H), 6.95 (d, J=9 Hz, 2H), 5.7 (s, 1H), 4.35 (t, J=7 Hz, 2H), 4.1 (m, 2H), 3.2 (m, 3H), 2.9 (m, 1H), 2.6 (d, J=4 Hz, 3H), 1.5 (s, 18H), 1.45 (t, J=7 Hz, 3H);

FDMS 464 (M$^+$-HCl);

Elemental analysis for C$_{29}$H$_{41}$ClN$_2$O$_3$.H$_2$O Calculated: C, 67.10; H, 8.35; N, 5.40. Found: C, 66.99; H, 7.96; N, 5.29.

EXAMPLE 4

2-(3,5-di-t-butyl-4-hydroxyphenyl)-4-(2-(3-dimethylaminomethyl-phenoxy)ethyl)oxazole hydrochloride A. Preparation of 2-(3,5-di-t-butyl-4-hydroxyphenyl)-4-(2-(3-formylphenoxy)ethyl)oxazole To 4.44 g (14 mmole) of the compound of Example 1C dissolved in tetrahydrofuran (THF) were added 1.94 g (16 mmole) of 3-hydroxybenzaldehyde and 4.18 g (16 mmole) of triphenylphosphine (PPh$_3$) under nitrogen. The solution was chilled to −50° and a solution of 2.51 ml (16 mmole) of diethyldiazodicarboxylate (DEAD) in 15 ml of tetrahydrofuran was added over 10 minutes with stirring. The bath was removed and the reaction stirred under nitrogen for 4 hours. Hydrogen peroxide (0.89 ml 30%) was added and the reaction was stirred for 15 minutes, stripped, dissolved in 40 ml of methylene chloride and placed in the freezer. The diethoxycarbonylhydrazine was then filtered off and the filtrate was chromatographed, eluting with a 5 to 20% acetone/hexane gradient over 30 minutes. The appropriate fractions were bulked and stripped to give 3.2 g (54%) of subtitled product.

NMR (CDCl$_3$), δ 1.49 (s, 18H), 3.10 (t, 2H, J=7 Hz), 4.35 (t, 2H, J=7 Hz), 5.50 (s, 1H), 7.20 (m, 1H), 7.44 (m, 3H), 7.51 (s, 1H), 7.84 (s, 2H), 9.97 (s, 1H)

B. Preparation of 2-(3,5-di-t-butyl-4-hydroxyphenyl)-4-(2-(3-dimethylaminomethylphenoxy)ethyl)oxazole hydrochloride Title compound was prepared from 3.2 g (7.6 mmole) of the compound of step A substantially in accordance with the procedure in Example 1E using 503 mg (8.0 mmole) of sodium cyanoborohydride and 9.5 ml (76 mmole) of 40% dimethylamine. Such reaction provided 1.82 g white foam (49%) which was triturated with methylene chloride/isopropyl ether to give 1.25 g of title product.

FDMS-M$^+$ 450;

Elemental Analysis for (C$_{28}$H$_{38}$N$_2$O$_3$.HCl) Calculated: C, 69.05; H, 8.07; N, 5.75 Found: C, 69.31; H, 8.13; N, 5.84

NMR (CDCl$_3$), δ 1.50 (s, 18H), 2.77 (d, 2H, J=5 Hz), 3.33 (t, 2H, J=7 Hz), 4.15 (d, 2H, J=4 Hz), 4.48 (t, 2H, J=7 Hz), 5.95 (s, 1H), 6.98 (dd, 1H, J=2 Hz, 9 Hz), 7.12 (d, 1H, J=9 Hz), 7.32 (t, 1H, J=9 Hz), 7.53 (d, 1H, J=2 Hz), 7.88 (s, 1H), 8.16 (s, 2H)

EXAMPLE 5

2-(3,5-di-t-butyl-4-hydroxyphenyl)-4-(2-(4-n-propylaminomethyl-phenoxy)ethyl)oxazole hydrochloride Title compound was prepared from 3.0 g (7.13 mmole) of the compound of Example 1D substantially in accordance with the procedure in Example 1E using 471 mg of sodium cyanoborohydride and 5.82 ml (71.3 mmole) of monopropylamine. Such reaction provided 1.67 g of the title product as a white foam (47%).

FDMS-M$^+$ 464;

Elemental analysis for (C$_{28}$H$_{38}$N$_2$O$_3$.HCl) Calculated: C, 69.51; H, 8.25; N, 5.59 Found: C, 69.80; H, 8.24; N, 5.46

NMR (CDCl$_3$), δ 0.92 (t, 3H, J=7 Hz), 1.49 (s, 18H), 1.86 (m, 2H, J=7 Hz), 2.71 (m, 2H, J=7 Hz), 3.28 (t, 2H, J=7 Hz), 3.94 (t, 2H, J=7 Hz), 4.30 (t, 2H, J=7 Hz), 6.00 (s, 1H), 6.87 (d, 2H, J=9 Hz), 7.50 (d, 2H, J=9 Hz), 7.74 (s, 1H), 8.17 (s, 2H), 9.70 (bs, 2H)

EXAMPLE 6

2-(3,5-di-t-butyl-4-hydroxyphenyl)-4-(2-(4-n-hexylaminomethyl-phenoxy)ethyl)oxazole hydrochloride The title compound was prepared substantially as described in Example 1E, except using N-hexylamine. The reaction was concentrated in vacuo then treated with 1:1 ethyl acetate:water (100 ml). Phases were separated, and the organics were washed with aqueous saturated sodium bicarbonate (50 ml) followed by a brine wash (50 ml). Organics were concentrated in vacuo then treated with diethyl ether and silica gel (10 g) and the resultant material was concentrated in vacuo to a flowable powder. The powder was subjected to silica gel flash chromatography eluting with methylene chloride (3×200 ml), methylene chloride:1% methanol (5×100 ml), 94:5:1 methylene chloride:methanol:ammonium hydroxide (10×100 ml), 89:10:1 methylene chloride:methanol:ammonium hydroxide (4×250 ml). Fractions containing desired product were combined and concentrated in vacuo to afford 2.37 g of an oil. The oil was treated with chloroform (75 ml) then hydrochloric acid gas. The resultant solution was concentrated in vacuo to afford a foam which was treated with hot methylene chloride (10 ml) then diisopropyl ether (10 ml) and concentrated until turbidity was observed. The turbid solution was placed in freezer for approximately 2.5 hours. Insolubles were collected by filtration, washed with diisopropyl ether and dried in a vacuum oven at 40° C. overnight to afford 1.46 g of the title compound.

Mass Spectrum(FDMS): m/z 506 (M).

$^1$H NMR (CdCl$_3$): δ 8.23 (s, 2H), 7.80 (s, 1H), 7.49 (d, J=8.3 Hz, 2H), 6.87 (d, J=8.3 Hz, 2H), 6.07 (s, 1H), 4.32 (m, 2H), 3.93 (m, 2H), 3.32 (m, 2H), 2.75 (m, 2H), 1.85 (m, 2H), 1.50 (m, 18H), 1.24 (m, 6H), 0.82 (t, J=6.6 Hz, 3H).

Elemental analysis for C$_{32}$H$_{47}$ClN$_2$O$_3$: Calculated: C, 70.76; H, 8.72; N, 5.16. Found: C, 70.68; H, 8.61; N, 5.16.

EXAMPLE 7

2-(3,5-di-t-butyl-4-hydroxyphenyl)-4-(2-(4-diethylaminomethyl-phenoxy)ethyl)oxazole hydrochloride dihydrate Title compound was prepared from 4.21 g (10 mmole) of the compound of Example 1D substantially in accordance with the procedure in Example 1E using 0.63 g (10 mmol) of sodium cyanoborohydride and diethylamine (10.3 ml, 100 mmole). The reaction was allowed to continue for 21 hours. The organic layer was chromatographed on silica gel using a methylene chloride/methanol gradient to give the free base which was then dissolved in methylene chloride, treated with hydrogen chloride gas and evaporated to provide 2.68 g (52%) of the title product.

$^1$H NMR (CDCl$_3$) δ 8.05 (s, 2H), 7.6 (s, 1H), 7.55 (d, J=9 Hz, 2H), 6.95 (d, J=9 Hz, 2H), 5.8 (s, 1H), 4.4 (t, J=7 Hz, 2H), 4.1 (d, J=5 Hz, 2H), 3.25 (t, J=7 Hz, 2H), 3.0 (m, 4H), 1.5 (s, 18H), 1.4 (t, J=7 Hz, 6H);

FDMS 478 (M$^+$-HCl);

Elemental analysis for C$_{30}$H$_{43}$ClN$_2$O$_3$·2H$_2$O: Calculated C, 64.32; H, 8.64; N, 5.00. Found: C, 63.94; H, 8.46; N, 4.80.

EXAMPLE 8

2-(3,5-di-t-butyl-4-hydroxyphenyl)-4-(2-(4-N-n-propyl-N-methylaminomethylphenoxy)ethyl)oxazole hydrochloride The title compound was prepared substantially as described in Example 1E, except using N-methyl-N-n-propylamine and chromatographing with 0 to 10% (methanol:1% ammonium hydroxide): chloroform gradient over a thirty-minute period. Fractions containing the desired product were concentrated in vacuo, treated with chloroform (100 ml) and magnesium sulfate, filtered and the filtrate was saturated with hydrogen chloride gas. The solution was concentrated in vacuo to a foam affording 3.40 g (68%) of the title compound.

Mass Spectrum(FDMS): m/z 478 (M).

$^1$H NMR (DMSOd$_6$): δ 8.31 (s, 1H), 7.91 (s, 1H), 7.72 (s, 2H), 7.51 (s, 1H), 7.16 (d J=8.4 Hz, 2H), 6.89 (d, J=8.4 Hz, 2H), 4.22 (t, J=6.4 Hz, 2H), 3.35 (s, 2H), 2.96 (t, J=6.4 Hz, 2H), 2.23 (t, J=7.3 Hz, 2H), 2.05 (s, 3H), 1.41 (m, 20H), 0.83 (t, J=7.3 Hz, 3H).

Elemental analysis for C$_{30}$H$_{43}$ClN$_2$O$_3$0H$_2$O: Calculated: C, 67.58; H, 8.51; N, 5.25. Found: C, 67.65; H, 8.34; N, 5.33.

EXAMPLE 9

2-(3,5-di-t-butyl-4-hydroxyphenyl)-4-(2-(4-N-n-propyl-N-ethylaminomethylphenoxy)ethyl)oxazole hydrochloride A solution of N-ethyl-N-propylamine (29.5 mmole, 2.58 g) in chloroform (10 ml) was saturated with hydrogen chloride gas. This solution was concentrated in vacuo then treated with ethanol (11 ml), triethylamine (29.5 mmole, 2.99 g), titanium IV isopropoxide (29.5 mmole, 8.40 g) and 2-(3,5-di-t-butyl-4-hydroxyphenyl)-4-(2-(4-formylphenoxy)ethyl)oxazole (14.8 mmole, 6.22 g), prepared as described in Example 1D above. The suspension was stirred at room temperature for 4 hours then carefully treated with sodium borohydride (22.2 mmole, 0.84 g) to avoid frothing. Reaction was stirred approximately 3 days before being treated with 2N ammonium hydroxide (23 ml). To this mixture was added methylene chloride (150 ml) and diatomaceous earth (20 g) and the mixture was filtered through a pad of diatomaceous earth and washed with methylene chloride (100 ml). The filtrate was washed with brine (1×50 ml) and the organic layer was concentrated in vacuo to an oil, treated with chloroform and subjected to preparatory chromatography. The material was eluted with 0 to 10% (1% ammonium hydroxide:methanol):chloroform gradient over a thirty-minute period. Fractions containing the desired product were concentrated in vacuo to an oil. The oil was treated with chloroform and saturated with hydrogen chloride gas. This solution was concentrated in vacuo to afford 4.78 g (61%) of the title compound.

Mass Spectrum(FDMS): m/z 492 (M-HCl).

$^1$H NMR (DMSOd$_6$): δ 10.45 (s, 1H), 7.94 (s, 1H), 7.73 (s, 2H), 7.53 (d, J=8.7 Hz, 2H), 7.03 (d, J=8.7 Hz, 2H), 4.28 (t J=6.5 Hz, 2H), 4.20 (t, J=5.2 Hz, 2H), 2.99 (m, 4H), 2.86 (m, 2H), 1.69 (m, 2H), 1.42 (s, 18H), 1.24 (t, J=7.2 Hz, 3H), 0.86 (t, J=7.3 Hz, 3H).

Elemental analysis for C$_{31}$H$_{45}$ClN$_2$O$_3$: Calculated: C, 70.36; H, 8.57; N, 5.29. Found: C, 70.08; H, 8.32; N, 5.30.

EXAMPLE 10

2-(3,5-di-t-butyl-4-hydroxyphenyl)-4-(2-(2,4-bis(methylethylaminomethyl)phenoxy)ethyl)oxazole dihydrochloride A. Preparation of 2-(3,5-di-t-butyl-4-hydroxyphenyl)-4-(2-(2,4-bis-formylphenoxy)ethyl)oxazole In a flask, 4.75 g (15 mmole) of the compound of Example 1C, 2.36 g (15.75 mmole) of 3-formyl-4-hydroxybenzaldehyde, and 3.93 g (15 mmole) of triphenylphosphine were dissolved in 45 ml tetrahydrofuran with stirring, under nitrogen. The solution was chilled to −10° and a solution of 2.36 ml (15 mmole) diethylazodicarboxylate in 15 ml. Tetrahydrofuran was added over 10 minutes, with stirring. The reaction exothermed to +1° C. The bath was removed and the reaction stirred under nitrogen for 18 hours. The reaction was then stripped, dissolved in a minimum amount of methylene chloride and placed in the freezer. The diethoxycarbonylhydrazine was then filtered off and the filtrate was chromatographed, Prep 500, two columns, eluting with 0 to 20% ethyl acetate/toluene gradient over 30 minutes. The appropriate fractions were bulked and stripped to give 3.3 g (49%) product which was used without further purification.

NMR (CDCl$_3$), δ 1.48 (s, 18H), 3.17 (t, 2H, J=7 Hz), 4.53 (t, 2H, J=5 Hz), 5.52 (s, 1H), 7.19 (d, 1H, 9 Hz), 7.53 (s, 1H), 7.84 (s, 2H), 8.11 (dd, 1H, J=2 Hz,9 Hz), 8.32 (d, 1H, J=2 Hz), 9.94 (s, 1H), 10.48 (s, 1H)

B. Preparation of 2-(3,5-di-t-butyl-4-hydroxyphenyl)-4-(2-(2,4-bis(methylethylaminomethyl)phenoxy)ethyl)oxazole dihydrochloride hydrate Title compound hydrochloride was prepared from 1.5 g (3.34 mmole) of the product of Step A substantially in accordance with the procedure in Example 9 using 4.0 ml (13.4 mmol) titanium IV isopropoxide and 1.15 ml (13.4 mmole) of methylethylamine and 0.38 g (10 mmole) sodium borohydride. The organics were chromatographed on 100 ml silica, eluting with methylene chloride/methanol and concentrated ammonia (90:10:1). Appropriate fractions were concentrated and dissolved in methylene chloride/isopropyl ether. Hydrogen chloride gas was bubbled in and the resultant residue was triturated with isopropyl ether to give 1.0 g (54%) of title product as a white foam.

FDMS-M$^+$ 536;

Elemental analysis for ($C_{33}H_{49}N_3O_3 \cdot 2HCl \cdot H_2O$) Calculated: C, 63.45; H, 8.52; N, 6.72 Found: C, 63.80; H, 8.53; N, 6.49

NMR (CDCl$_3$), δ 1.30–1.40 (m, 6H), 1.48 (s, 18H), 2.45–2.70 (m, 6H), 2.79–3.35 (m, 6H), 3.90–4.30 (m, 4H), 4.38 (t, 2H, J=5 Hz), 5.58 (s, 1H), 7.08 (d, 1H, J=9 Hz), 7.57 (s, 1H), 7.84 (s, 2H), 8.03 (d, 1H, J=9 Hz), 8.13 (s, 1H)

EXAMPLE 11

2-(3,5-di-t-butyl-4-hydroxyphenyl)-4-(2-(4-(2-hydroxyethyl)ethylaminomethylphenoxy)ethyl) oxazole hydrochloride To a stirred solution of N-ethylethanolamine (1.95 ml, 20 mmole) in ethanol (25 ml) was added titanium IV isopropoxide (5.9 ml, 20 mmole), then the compound of Example 1D (4.21 g, 10 mmole). The reaction was stirred for 4 hours, then sodium borohydride (0.57 g, 15 mmole) was added. After 20 hours at room temperature, the reaction was poured into 75 ml 2N ammonium hydroxide and diluted with methylene chloride. The mixture was filtered though diatomaceous earth and the filtrate was extracted with brine. The organic layer was dried over sodium sulfate, evaporated to dryness, and chromatographed on silica gel using a methylene chloride/methanol gradient to give the free base (3.56 g, 72%). The free base was dissolved in methylene chloride (86 ml), treated with hydrogen chloride gas, and evaporated to give desired product (3.92 g, 100%):

$^1$H NMR (CDCl$_3$) δ 8.0 (s, 2H), 7.6 (s, 1H), 7.5 (d, J=9 Hz, 2H), 6.95 (d, J=9 Hz, 2H), 5.7 (s, 1H), 4.35 (t, J=7 Hz, 2H), 4.2 (m, 2H), 3.9 (m, 2H), 3.2 (t, J=7 Hz, 2H), 3.15 (m, 4H), 1.5 (m, 21H);

FD MS 494 (M$^+$-HCl);

Elemental Analysis for $C_{30}H_{43}ClN_2O_4 \cdot 0.5\ H_2O$: Calculated: C, 66.71; H, 8.21; N, 5.19. Found: C, 66.47; H, 8.10; N, 5.20.

EXAMPLE 12

2-(3,5-di-t-butyl-4-methoxyphenyl)-4-(2-(4-N-bis[hydroxyethyl]aminomethylphenoxy)ethyl)oxazole hydrochloride The title compound was prepared substantially as described in Example 11 except using diethanolamine. The material was subjected to preparatory chromatography, eluting with a gradient of 0 to 10% (1% ammonium hydroxide/methanol):chloroform over a thirty minute period. Fractions containing the title compound were combined and concentrated in vacuo to afford an oil. The oil was treated with chloroform then hydrogen chloride gas and concentrated in vacuo to afford 817 mg of the title compound as a foam.

Mass Spectrum (FDMS): m/z 510. (M-HCl).

$^1$H NMR (CDCl3): δ 7.96 (s, 2H), 7.58 (s, 1H), 7.48 (d, J=8.6 Hz, 2H), 6.97 (d, J=8.6, 2H), 5.68 (s, 1H), 4.35 (m, 4H), 4.01 (m, 4H), 3.33 (m, 4H), 3.17 (m,2H), 1.48 (s, 18H).

Elemental analysis for C30H43ClN2O5+0.3 mole H2O: Calculated: C, 65.21; H, 7.95; N,5.07. Found: C, 65.18; H, 7.95; N, 4.67.

EXAMPLE 13

2-(3,5-di-t-butyl-4-hydroxyphenyl)-4-(2-(4-[N-methyl-N-(3-piperidin-3-yl)propyl)aminomethyl] phenoxy)ethyl)oxazole dihydrochloride A. Preparation of 2-(3,5-di-t-butyl-4-hydroxyphenyl)-4-(2-(4-N-methyl-N-aminomethylphenoxy)ethyl)oxazole The subtitled compound was prepared substantially as described in Example 11, except using the methylamine hydrochloride salt. The crude material was subjected to preparatory chromatography. The material was eluted with 0 to 10% (1% ammonium hydroxide:methanol):chloroform gradient over a thirty minute period. Fractions containing desired product were reduced in vacuo, dried over sodium sulfate, filtered and concentrated in vacuo, to afford 6.74 g (62%) of the title compound.

Mass Spectrum(FDMS): m/z 436 (M).

$^1$H NMR (CdCl$_3$): δ 7.83 (s, 2H), 7.46 (s, 1H), 7.42 (d, J=8.3 Hz, 2H), 6.92 (d, J=8.3 Hz, 2H), 5.30 (bs, 1H), 4.22 (t J=6.5 Hz, 2H), 3.93 (s, 2H), 3.03 (t, J=6.5 Hz, 2H), 2.46 (s, 3H), 1.48 (s, 18H).

Elemental analysis for $C_{27}H_{36}N_2O_3$: Calculated: C, 74.28; H, 8.31; N, 6.42. Found: C, 74.39; H, 8.51; N, 6.47.

B. Preparation of 2-((3,5-di-t-butyl-4-hydroxyphenyl)-4-[N-methyl-N-(3-(N'-tert-butoxycarbonylpiperid-3-yl)propyl) amino methyl]phenoxy)ethyl)oxazole A red solution of the compound of Step A, (9.2 mmole, 4.01 g), in dimethylformamide (DMF, 18 ml) was treated with 60% (wt/wt) sodium hydride (20.2 mmole, 808 mg). The suspension was stirred for 30 minutes at 24° C. then treated with a solution of N-tert-butoxycarbonyl-3-(3-bromopropyl)piperidine (8.4 mmole, 2.56 g) in dimethylformamide (5 ml). Next, the suspension was heated at 80° C. for 4 hours then cooled to 24° C. The reaction treated with 10% aqueous sodium bisulfate (25 ml), water (10 ml) and 3/2 ethyl acetate:hexane (50 ml). The phases were separated and the aqueous phase was extracted with 3:2 ethyl acetate:hexane (2×50 ml). Combined organics were washed with brine (2×50 ml), dried over sodium sulfate, filtered and concentrated in vacuo to afford 6.67 g of an oil. The crude material was subjected to preparatory chromatography. The material was eluted with 0 to 10% (1% ammonium hydroxide:methanol):chloroform gradient over a thirty-minute period. Fractions containing the desired product were reduced in vacuo, dried over sodium sulfate, filtered and concentrated in vacuo, to afford 4.19 g of the title compound. This material contained some impurities and was taken on to the next step without further purification.

Mass Spectrum(FDMS): m/z 662 (M+1).

$^1$H NMR (CdCl$_3$): δ 7.83 (s, 2H), 7.50 (s, 1H), 7.19 (d, J=8.4 Hz, 2H), 6.88 (d, J=8.4 Hz, 2H), 5.49 (S, 1H), 4.27 (t J=6.6 Hz, 2H), 3.91 (m, 1H), 3.40 (s, 2H), 3.07 (t, J=6.6 Hz, 2H), 2.72 (m, 1H), 2.32 (t, J=7.3 Hz, 2H), 2.15 (s, 3H), 1.80 (m, 1H), 1.37–1.69 (m, 26H), 1.22 (m, 2H).

C. Preparation of 2-(3,5-di-t-butyl-4-hydroxyphenyl)-4-(2-(4-[N-methyl-N-(3-(N'-tert-butoxycarbonyl-piperid-3-yl)propyl)aminomethyl]phenoxy)ethyl)oxazole hydrochloride A solution of the compound of Step B (3.15 mmole, 2.09 g) in diethyl ether (20 ml) was treated with hydrogen chloride gas for approximately 10 minutes. The resulting heavy suspension was stirred an additional 20 minutes, filtered and washed with diethyl ether (20 ml) to afford 2.01 g (91%) of the subtitled compound.

Mass Spectrum(FDMS): m/z 661 (M).

$^1$H NMR (CdCl$_3$): δ 8.13 (s, 2H), 7.66 (s, 1H), 7.50 (d, J=8.5 Hz, 2H), 6.96 (d, J=8.5 Hz, 2H), 5.91 (s, 1H), 4.41 (t J=5.9 Hz, 2H), 4.10 (m, 2H), 3.84 (s, 2H), 3.30 (t, J=5.8 Hz, 2H), 2.96 (m, 1H), 2.78 (m, 2H), 2.63 (m, 3H), 2.49 (dd, J=9.9, 12.9 Hz, 1H), 1.85 (m, 2H), 1.50 (s, 27H).

Elemental analysis for $C_{40}H_{60}ClN_3O_5$: Calculated: C, 68.89; H, 8.53; N, 6.03. Found: C, 68.65; H, 8.45; N, 6.02.

D. Preparation of 2-(3,5-di-t-butyl-4-hydroxyphenyl)-4-(2-(4-[N-methyl-N-(3-(piperidin-3-yl)propyl)aminomethyl] phenoxy)ethyl)oxazole dihydrochloride To a solution of the compound of Step C (3.0 mmole, 2.01 g) in chloroform (20 ml) was added thiophenol (6.07 mmole, 0.67 g). Next, hydrogen chloride gas was passed through this solution for approximately 30 minutes then stirred overnight at 24° C. before being concentrated in vacuo to a foam. The material was taken up into hot methylene chloride (10 ml) then tetrahydrofuran (15 ml) was added while heating the solution. The solution was boiled down to approximately 12 ml total volume, cooled to approximately −22° C. before tetrahydrofuran (10 ml) was added, resulting in the formation of a precipitate. The suspension was filtered, the insolubles were transferred with methylene chloride and the volume was reduced to approximately 5 ml. Tetrahydrofuran (20 ml) was added and the solution was boiled down to approximately 5 ml. Next, diethyl ether (20 ml) was added to the hot solution resulting in the formation of a gum. The suspension was cooled to 24° C., the gum was triturated and insolubles were collected by filtration and washed with diethyl ether (20 ml). Insolubles were resuspended with stirring in hot diethyl ether (150 ml). After heating for approximately 30 minutes (keeping volume between 100–150 ml) the insolubles were collected by filtration and washed with hot diethyl ether (100 ml). Insolubles were dried in a vacuum oven at 60° C. overnight to afford 1.32 g (72%) of the title compound.

Mass Spectrum(FDMS): m/z 562 (M+1).

$^1$H NMR (CdCl$_3$): δ 8.00(s, 2H), 7.62 (s, 1H), 7.50 (d, J=8.1 Hz, 2H), 6.95 (d, J=8.1 Hz, 2H), 5.74 (s, 1H), 4.35 (m, 2H), 4.26 (m, 2H), 3.59 (m, 1H), 3.37 (m, 1H), 3.20 (m, 2H), 3.04 (m, 1H), 2.66–2.89 (m, 4H), 2.55 (m, 1H), 1.80–2.25 (m, 7H), 1.49 (s, 18H), 1.11–1.41 (m, 3H).

Elemental analysis for $C_{35}H_{53}Cl_2N_3O_3$: Calculated C, 66.23; H, 8.42; N, 6.62. Found: C, 66.47; H, 8.67; N, 6.39.

EXAMPLE 14

2-(3,5-di-t-butyl-4-hydroxyphenyl)-4-(2-(4-N-methyl-N-ethylaminoethylphenoxy)ethyl)oxazole hydrochloride heptahydrate A. Preparation of N-formyl-N-ethyl-p-hydroxyphenethylamine To a suspension of 1,1'-carbonyldiimidazole (326 mmole, 52.81 g) in tetrahydrofuran (164 ml) cooled to 0° C., was added dropwise 96% formic acid (326 mmole, 14.99 g) over a 26 minute period. Reaction stirred at 0° C. for 30 minutes then a light suspension of N-ethyl-p-hydroxyphenethylamine (102 mmole, 16.88 g) in tetrahydrofuran (66 ml) was added over a 10 minute period. Reaction then stirred at 22° C. for 170 minutes before being treated with methanol (10 ml). After stirring for 90 minutes, reaction was concentrated in vacuo to an oil containing crystals. The mixture was taken up into methylene chloride and subjected to preparatory chromatography eluting with a gradient of 0 to 5% methanol:methylene chloride over a thirty-minute period. The fractions containing the title compound were combined, concentrated in vacuo to afford 13.46 g of an oil that slowly crystallizes out. Fractions containing title compound and impurities were resubjected to preparatory column chromatography under the same conditions described above to afford an additional 2.61 g of the title compound.

mp (°C.):85

Mass Spectrum (FDMS): m/z 193. (M).

$^1$H NMR (DMSOd$_6$): δ 9.20 (s, 1H), 8.01 (s, 1/2H), 7.72 (s, 1/2H), 7.00 (d, J=8.4 Hz, 1H), 6.99 (d, J=8.4 Hz, 1H), 6.66 (d, J=8.4 Hz, 2H), 3.34 (dt, J=7.2 Hz, 2H), 3.21 (dq, J=7.1 Hz, 2H), 2.64 (dt, J=7.2 Hz, 2H), 1.04 (dt, J=7.1 Hz, 2H).

Elemental analysis for $C_{11}H_{15}NO_2$ Calculated: C, 68.37; H, 7.82; N, 7.25. Found: C, 68.56; H, 7.81; N, 7.49.

B. Preparation of 2-(3,5-di-t-butyl-4-hydroxyphenyl)-4-(2-(4-N-formyl-N-ethylaminoethylphenoxy)ethyl)oxazole The title compound was prepared substantially as described in Example 4 above except using N-formyl-N-ethyl-p-hydroxyphenethylamine and 0.7M (mmole alcohol/ml tetrahydrofuran) reaction solution. After stirring at 24° C. for approximately 22 hours, the reaction was concentrated in vacuo. The filtrate was concentrated in vacuo to an oil, treated with ethyl acetate and subjected to preparatory chromatography. The material was eluted with 45% ethyl acetate. Fractions containing desired product were concentrated in vacuo then resubjected to preparatory chromatography. The material was eluted with 0 to 20% ethyl acetate/(93% chloroform:hexane) gradient over a thirty minute period. Fractions containing the desired product were concentrated in vacuo then resubjected to preparatory chromatography. The material was eluted with 5 to 30% acetone/hexane gradient over a thirty minute period. Fractions containing desired product were concentrated in vacuo to afford 3.01 g (19%) of the subtitled compound as a foam.

Mass Spectrum(FDMS): m/z 493 (M+1).

$^1$H NMR (DMSOd$_6$): δ 8.01 (s, 1/2H), 7.91 (s, 1/2H), 7.74 (s, 1H), 7.72 (s, 2H), 7.52 (bs, 1H), 7.13 (d, J=8.4 Hz, 2H), 6.88 (d, J=8.4 Hz, 2H), 4.20 (t, J=6.5 Hz, 2H), 3.40 (dt, J=7.1 Hz, 2H), 3.22 (dq, J=7.1 Hz, 2H), 2.96 (t, J=6.5 Hz, 2H), 2.71 (dt, J=7.1 Hz, 2H), 1.41 (s, 18H), 1.04 (dt, J=7.1 Hz, 3H).

Elemental analysis for $C_{30}H_{40}N_2O_4$: Calculated: C, 73.14; H, 8.18; N, 5.69. Found: C, 73.30; H, 8.44; N, 5.90.

C. Preparation of 2-(3,5-di-t-butyl-4-hydroxyphenyl)-4-(2-(4-N-methyl-N-ethylaminoethylphenoxy)ethyl)oxazole Sulfuric acid (6.0 mmole, 0.597 g) was carefully added dropwise over an eight minute period to a cooled suspension of lithium aluminum hydride (12.2 mmole, 0.462 g) in tetrahydrofuran (THF, 18 ml). After the addition was complete, the ice bath was removed. Approximately one hour after the addition, the reaction was cooled to 0° C., then a solution of the compound of Step B in tetrahydrofuran (4 ml) was added over a ten minute period. The reaction was stirred at 24° C. for 3 hours then quenched with water (12.2 mmole, 214 μL). Next, chloroform (200 ml) was added followed by 5N hydrochloric acid (50 ml). Phases were separated and the aqueous phase was extracted with chloroform (2×50 ml). Combined organic phases were washed with brine (1×50 ml) then dried over sodium chloride, filtered and concentrated in vacuo to afford 5.8 g of an oil that contained some solids. The material was treated with ethyl acetate (250 ml) then washed with saturated aqueous sodium bicarbonate (2×50 ml). The organics were dried over sodium sulfate, filtered then concentrated in vacuo to afford 2.77 g of an oil. The material was treated with chloroform and subjected to preparatory chromatography. The material was eluted with 0 to 10% (1% ammonium hydroxide:methanol):chloroform gradient over a 30 minute period. Fractions containing the desired product were concentrated in vacuo to an oil. This material was taken up into chloroform then saturated with hydrogen chloride gas. The solution was concentrated in vacuo to afford 1.35 g (43%) of the title compound as a foam.

Mass Spectrum(FDMS): m/z 478 (M+1).

$^1$H NMR (DMSOd$_6$): δ 7.92 (s, 1H), 7.72 (s, 2H), 7.54 (s, 1H), 7.21 (d, j=8.6 Hz, 2H), 6.93 (d, J=8.6 Hz, 2H), 4.22 (t, J=6.6 Hz, 2H), 3.19 (m, 4H), 2.98 (m, 4H), 2.76 (d, J=4.9 Hz, 3H), 1.41 (s, 18H), 1.22 (t, J=7.2 Hz, 3H).

Elemental analysis for $C_{30}H_{40}N_2O_4 \cdot 0.7H_2O$ Calculated: C, 68.28; H, 8.48; N, 5.31. Found: C, 68.20; H, 8.41; N, 5.35.

EXAMPLE 15

2-(3,5-di-t-butyl-4-hydroxyphenyl)-4-(2-(4-N-ethyl-N-methylaminobutyl)phenoxyethyl)oxazole hydrochloride A. Preparation of 4-(4-hydroxyphenyl)butyl bromide A solution of triphenylphosphine (144.1 mmole, 37.80 g) in methylene chloride (556 ml) was treated with bromine (144.1 mmole, 23.03 g) until a pale yellow color persisted. After stirring approximately 15 minutes, a solution of 4-(4-hydroxyphenyl)butanol (96.1 mmole, 15.97 g) and imidazole (192.2 mmole, 13.08 g) in methylene chloride (355 ml) was added over a 15 minute period. Approximately 4 hours later, the reaction suspension was filtered and the filtrate was reduced in volume. To the reduced filtrate was added silica gel and the suspension was reduced to dryness. This material was filtered and the first six fractions were eluted with 10% ethyl acetate:hexane. Fractions 7 through 12 were eluted with 20% ethyl acetate:hexane. Fractions 7 through 10 were combined, reduced in volume, dried over sodium sulfate, filtered and concentrated in vacuo to afford 19.32 g (88%) of the title compound as an oil.

Mass Spectrum (FDMS): m/z 230. (M+1).

1H NMR (CDCl3): $\delta$ 7.03 (d, J=8.4 Hz, 2H), 6.75 (d, J=8.4 Hz, 2H), 4.59 (s, 1H), 3.40 (t, J=6.7 Hz, 2H), 2.56 (m, 2H), 1.83–1.90 (m, 2H), 1.70–1.77 (m, 2H).

Elemental analysis for C10H13BrO: Calculated: C,52.42; H, 5.72. Found: C, 52.24; H, 5.61.

B. Preparation of 2-(3,5-di-t-butyl-4-hydroxyphenyl)-4-(2-(4-(4-bromobutyl)phenoxyethyl)oxazole The title compound was prepared substantially as described in Example 4 except using the compound of Step A. The reaction was concentrated in vacuo to an oil. The oil was treated with chloroform (25 ml), triturated, then treated with diatomaceous earth and filtered through a pad of diatomaceous earth. The filtrate was reduced in volume then subjected to preparatory chromatography. The material was eluted with a gradient of 20 to 35% diethyl ether:hexane over a 30 minute period. Fractions 4–15 were combined, concentrated in vacuo then rechromatographed eluting with a gradient of 20 to 35% diethyl ether:hexane over a 30 minute period. Fractions 8–16 were combined, concentrated in vacuo then rechromatographed eluting with a gradient of 5 to 20% ethyl acetate:(33% chloroform:67% hexane) over a 30 minute period. Fractions 7–9 were combined, dried over sodium sulfate, filtered and concentrated in vacuo to afford 10.51 g (49%) of the title compound.

Mass Spectrum (FDMS): m/z 529. (M+1).

1H NMR (CDCl3): $\delta$ 7.83 (s, 2H), 7.50 (s, 1H), 7.08 (d, J=8.5 Hz, 2H), 6.85 (d,J=8.5 Hz, 2H), 5.49 (s, 1H), 4.25 (t, J=6.6 Hz, 2H), 3.41 (t, J=6.6 Hz, 2H), 3.06(t, J=6.6 Hz, 2H), 2.58 (t, J=7.4 Hz, 2H), 1.88 (m, 2H), 1.72 (m, 2H), 1.49 (s,18H).

Elemental analysis for C29H38BrNO3: Calculated: C,65.90; H, 7.25; N, 2.65. Found: C,66.14; H, 7.26; N, 2.36.

C. Preparation of 2-(3,5-di-t-butyl-4-hydroxyphenyl)-4-(2-(4-N-ethyl-N-methylaminobutyl)phenoxyethyl)oxazole hydrochloride A solution of N-methylethyl amine (7.8 mmole, 0.46 g) in dimethylformamide (21 ml) was treated with sodium hydride (7.8 mmole, 0.68 g). The suspension was heated at 35° C. for 15 minutes. Next, the suspension was treated with a solution of a compound of Step B (8.5 mmole, 4.51 g) in dimethylformamide (21 ml). The suspension was then heated at 70° C. for approximately 4.5 hours before additional N-methylethyl amine (15.6 mmole, 0.92 g) was added. Forty five minutes later the reaction was cooled to 22° C., treated with ethyl acetate (50 ml), hexane (25 ml) and 10% aqueous sodium sulfate 950 ml). The phases were separated and the aqueous phase was extracted with 2:1 ethyl acetate:hexane (3×75 ml). Combined organics were washed with brine (2×100 ml), dried over sodium sulfate, filtered and concentrated in vacuo to afford 4.16 g of an oil. The oil was treated with chloroform, filtered through a pad of diatomaceous silica and washed with chloroform. The filtrate was subjected to preparatory silica gel chromatography. The material was eluted with a gradient of 0 to 10% (1% ammonium hydroxide:methanol):chloroform over a thirty minute period. Fractions containing the desired product were combined, concentrated in vacuo, taken up into chloroform (100 ml), washed with 1:1 saturated aqueous sodium bicarbonate water (50 ml) then brine (50 ml). The organics were dried over sodium sulfate, filtered and concentrated in vacuo to afford 1.6 g of an oil. The oil was treated with chloroform (50 ml) then saturated with hydrogen chloride gas. This solution was concentrated in vacuo to a foam. The foam was treated with tetrahydrofuran (THF) and boiled on a steam bath while slowly adding diiusopropyl ether. The tetrahydrofuran was boiled off, resulting in the product oiling out. The remaining solvent was decanted off and isopropyl ether (10 ml) was added. The biphasic solution was boiled on steam bath, solvent was decanted and the remaining material was pulled on house vacuum overnight to afford 1.38 g of the title compound as a foam.

Mass Spectrum (FDMS): m/z 506. (M).

1H NMR (CDCl3): $\delta$ 7.86 (s, 2H), 7.52 (s, 1H), 7.06 (d, J=8.5 Hz, 2H), 6.85 (d,J=8.5 Hz, 2H), 5.54 (s, 1H), 4.26 (t, J=6.5 Hz, 2H), 3.08 (t, J=6.5 Hz, 2H), 2.88(m, 3H), 2.67 (d, J=4.9 Hz, 3H), 2.60 (t, J=7.3 Hz, 2H), 1.66–1.85 (m, 3H),1.38–1.48 (m, 24H).

Elemental analysis for C32H47ClN2O3: Calculated: C, 70.76; H, 8.72; N, 5.16. Found: C,70.52; H, 8.56; N, 5.41.

EXAMPLE 16

2-(3,5-di-t-butyl-4-hydroxyphenyl)-4-(2-(3-N-ethyl-N-methylaminopropyl)phenoxy)ethyl)oxazole hydrochloride A. Preparation of 2-(3,5-di-t-butyl-4-hydroxyphenyl)-4-(2-(4-(2-cyanoethyl)phenoxyethyl)oxazole The title compound was prepared substantially as described in Example 4 except using 3-(4-hydroxyphenyl)propionitrile. The reaction was concentrated in vacuo to an oil. The oil was treated with chloroform (75 ml), triturated, and filtered. The filtrate was washed with saturated aqueous sodium bicarbonate (2×250 ml) and 10% sodium bisulfate (1×250 ml). The organic layer was dried over sodium sulfate, filtered and concentrated in vacuo to afford a dark oil. The oil was treated with methylene chloride and subjected to preparatory silica gel chromatography. Material was eluted with a gradient of 10 to 25% ethyl acetate:hexane over a thirty minute period. Fractions containing the title compound were combined and concentrated in vacuo to afford 29.57 g of an oil. This material was resubjected to preparatory silica gel chromatography eluting with a gradient of 15 to 35% diethyl ether:hexane over a thirty minute period. Fractions containing the title compound were combined and concentrated in vacuo to afford 20.57 g of foam. This material was resubjected to preparatory silica gel chromatography eluting with a gradient of 10 to 30% acetone:hexane over a thirty minute period. Fractions containing the title compound were combined and concentrated in vacuo to afford 14.71 g of foam. This material contained trace impurities and was taken on to the next step without further purification.

Mass Spectrum (FDMS): m/z 446. (M).

1H NMR (DMSOd6): δ 7.92 (s, 1H), 7.73 (s, 2H), 7.52 (s, 1H), 7.19 (d, J=8.6 Hz,2H), 6.91 (d, J=8.6 Hz, 2H), 4.23 (t, 2H), 2.96 (t, 2H), 2.78 (m, 4H), 1.42 (s,18H).

B. Preparation of 2-(3,5-di-t-butyl-4-hydroxyphenyl)-4-(2-(4-(2-formylethyl)phenoxyethyl)oxazole To a cooled solution of the compound of Step A (32.9 mmole, 14.68 g) in toluene (105 ml) at −78° C., was added a 1.0 molar solution of diisobutylaluminum hydride (42.7 mmole, 42.7 ml) over a seventeen minute period. The reaction was then stirred at 22° C. for 1 hour and quenched with methanol (4.7 ml). The suspension was cooled to 0° C. and treated with a saturated solution of ammonium hydroxide (300 ml). After stirring for 1.5 hours, the reaction was treated with 50% sulfuric acid until a biphasic solution resulted. The mixture was then treated with ethyl acetate (250 ml) and the phases were separated. The aqueous phase was extracted with ethyl acetate (3×100 ml). The combined organic phases were washed with brine (2×200 ml), dried over sodium sulfate, filtered and concentrated in vacuo to an oil. The oil was subjected to preparatory silica gel chromatography. Material was eluted with a gradient of 0 to 10% methanol:toluene over a thirty minute period. Fractions containing subtitled compound were combined, concentrated in vacuo to afford 11.76 g of an oil. This material was taken on to the next step without further purification.

Mass Spectrum (FDMS): m/z 449. (M).

1H NMR (DMSOd6): δ 9.70 (S, 1H), 7.91 (s, 1H), 7.73 (s, 2H), 7.53 (s, 1H), 7.12(d, J=8.6 Hz, 2H), 6.87 (d, J=8.6 Hz, 2H), 4.20 (t, J=6.5 Hz, 2H), 2.96 (t,J=6.5 Hz, 2H), 2.75 (m, 4H), 1.42 (s, 18H).

C. Preparation of 2-(3,5-di-t-butyl-4-hydroxyphenyl)-4-(2-(3-N-ethyl-N-methylaminopropyl)phenoxy)ethyl)oxazole hydrochloride (366241)

The title compound was prepared substantially as described in Example 11 except using the compound of step B and N-methylethylamine. The material was subjected to preparatory chromatography eluting with a gradient of 0 to 5% (1% ammonium hydroxide:methanol):chloroform over a thirty minute period. Remaining fractions eluted with 5% (1% ammonium hydroxide:methanol):chloroform. Fractions containing desired product were combined, concentrated in vacuo, taken up into chloroform (100 ml) and washed with saturated sodium bicarbonate (10 ml) and water (15 ml) followed by water (25 ml). The organic layer was dried over sodium sulfate and filtered. The filtrate was saturated with hydrogen chloride gas and concentrated in vacuo to afford 1.61 g of the title compound as a foam.

Mass Spectrum (FDMS): m/z 492. (M-HC$_1$).

1H NMR (CDCl3): δ 7.84 (s, 2H), 7.51 (s, 1H), 7.07 (d, J=8.6 Hz, 2H), 6.86 (d,J=8.6 Hz, 2H), 5.51 (s, 1H), 4.25 (t, J=6.6 Hz, 2H), 2.84–3.09 (m, 6H), 2.67 (m,5H), 2.13–2.21 (m, 2H), 1.48 (s, 18H), 1.39 (t, J=7.3 Hz, 3H).

Elemental analysis for C31H45ClN2O3+0.2 mole H2O: Calculated: C, 69.89; H, 8.58; N,5.26. Found: C, 69.88; H, 8.73; N, 5.32.

EXAMPLE 17

2-(3,5-di-t-butyl-4-methoxyphenyl)-4-(2-(4-N-ethyl-N-methylaminomethylphenoxy)ethyl)oxazole hydrochloride A. Preparation of 2-(3,5-di-t-butyl-4-methoxyphenyl)-4-(2-(4-formylphenoxy)ethyl)oxazole A solution of the compound of Example 1D (8.4 mmole, 3.54 g) and methyl iodide (67.3 mmole, 9.54 g) in tetrahydrofuran (40 ml) and dimethylformamide (4 ml) was treated with sodium hydride (60% wt/wt, 16.8 mmole, 0.67 g). After stirring 31 hours at 22° C., the reaction was treated with water (10 ml) and the pH was adjusted from 12.6 to 5.4 with 1N hydrochloric acid. The biphasic solution was reduced in volume to remove tetrahydrofuran then ethyl acetate was added (100 ml) followed by 10% aqueous sodium bisulfate (50 ml). The phases were separated and the organic phase was dried over sodium sulfate and filtered. The filtrate was subjected to preparatory silica gel chromatography, eluting with a gradient of 20 to 45% ethyl acetate:hexane over a thirty minute period. Fractions containing subtitled compound were combined and concentrated in vacuo to afford 3.57 g of an oil. Material was taken on to next step without further purification.

Mass Spectrum (FDMS): m/z 435. (M).

1H NMR (CDCl3): δ 9.88 (s, 1H), 7.90 (s, 2H), 7.82 (d, J=8.8 Hz, 2H), 7.53 (s,1H), 7.02 (d, J=8.8 Hz, 2H), 4.36 (t, J=6.5 Hz, 2H), 3.70 (s, 3H), 3.11 (t,J=6.5 Hz, 2H), 1.46 (s, 18H).

B. Preparation of 2-(3,5-di-t-butyl-4-methoxyphenyl)-4-(2-(4-N-ethyl-N-methylaminomethylphenoxy)ethyl)oxazole hydrochloride The title compound was prepared substantially as described in Example 11 except using the compound of Step A. The material was subjected to preparatory chromatography eluting with a gradient of 0 to 10% (1% ammonium hydroxide:methanol):chloroform over a thirty minute period. Fractions containing title compound were combined and concentrated in vacuo to a foam. The foam was treated with chloroform then saturated with hydrogen chloride gas. This solution was concentrated in vacuo to afford 2.2 g of the title compound as a foam.

Mass Spectrum (FDMS): m/z 478. (M-HCl).

1H NMR (DMSOD6): δ 10.46 (s, 1H), 8.00 (s, 1H), 7.83 (s, 2H), 7.51 (d, J=8.6 Hz,2H), 7.04 (dd, J=8.6, 2H), 4.09–4.31 (m, 4H), 3.68 (s, 3H), 2.92–3.11 (m, 4H),2.57 (d, J=4.8 Hz, 3H), 1.42 (s, 18H), 1.25 (t, J=7.2 Hz, 3H).

Elemental analysis for C30H43ClN2O3+0.2 mole H2O: Calculated: C, 69.46; H, 8.43; N,5.40. Found: C, 69.23; H, 8.47; N, 5.53.

EXAMPLE 18

2-(3,5-di-t-butyl-4-hydroxyphenyl)-4-(2-(4-(4-dimethylaminobutyryl)phenyloxy)ethyl)oxazole hydrochloride A. Preparation of 2-(3,5-di-t-butyl-4-hydroxyphenyl)-4-(2-(4-(4-chlorobutyryl)phenyloxy)ethyl)oxazole To a stirred solution of the compound of Example 1C (5.68 g, 17.92 mmole) in tetrahydrofuran (54 ml) was added 4-chloro-4'-hydroxybutyrophenone (3.56 g, 17.92 mmole) and triphenylphosphine (5.16 g, 19.71 mmole). After cooling to −20° C., a solution of diethylazodicarboxylate (3.1 ml, 19.71 mmole) in tetrahydrofuran (18 ml) was added dropwise over 15 min. The reaction was allowed to warm to room temperature and stir for 5 hours, at which time it was diluted with diethyl ether and extracted with water and brine. The organic layer was dried over sodium sulfate, evaporated to dryness, and chromatographed on silica gel using a hexane-acetone gradient to give the intermediate chloroketone (4.77 g, 53%):

$^1$H NMR (CDCl$_3$) δ 7.95 (d, J=9 Hz, 2H), 7.85 (s, 2H), 7.5 (s, 1H), 6.95 (d, J=9 Hz, 2H), 5.5 (s, 1H), 4.35 (t, J=7 Hz, 2H), 3.7 (t, J=6 Hz, 2H), 3.1 (m, 4H), 2.2 (m, 2H), 1.5 (s, 18H); FD MS 497 (M$^+$).

B. Preparation of 2-(3,5-di-t-butyl-4-hydroxyphenyl)-4-(2-(4-(4-dimethylaminobutyryl)phenyloxy)ethyl)oxazole hydrochloride To a stirred solution of the chloroketone (5.09 g, 10.2 mmole) in acetone (51 ml) was added sodium iodide (7.66 g, 51 mmole). The reaction was heated at 50° C. for 28 hours, evaporated to dryness, and redissolved in methylene chloride and water. The organic layer was extracted with brine, dried over sodium sulfate, and evaporated to dryness to give the intermediate iodoketone, which was used without further purification. The iodoketone was dissolved in toluene (30 ml), cooled to 0° C. and treated with anhydrous dimethylamine (0.79 ml, 12 mmole). The reaction was heated to 80° C. for 3 hours, then allowed to cool to room temperature. A white precipitate was filtered, and the filtrate was diluted with ethyl acetate and saturated sodium bicarbonate. The organic layer was extracted with 0.1N sodium thiosulfate and brine, dried over sodium sulfate, evaporated to dryness, and chromatographed on silica gel using a methylene chloride/methanol gradient to give the free base (1.82 g, 35%). The free base was dissolved in methylene chloride (50 ml), treated with hydrogen chloride gas, and evaporated to give desired product (1.87 g, 96%):

$^1$H NMR (CDCl$_3$) δ 8.0 (s, 2H), 7.95 (d, J=9 Hz, 2H), 7.6 (s, 1H), 6.95 (d, J=9 Hz, 2H), 5.8 (s, 1H), 4.4 (t, J=7 Hz, 2H), 3.3–3.1 (m, 6H), 2.8 (d, J=4 Hz, 6H), 2.25 (m, 2H), 1.5 (s, 18H);

FDMS 506 (M$^+$-HCl);

Elemental analysis for C$_{31}$H$_{43}$ClN$_2$O4: Calculated: C, 68.55; H, 7.98; N, 5.16. Found: C, 68.36; H, 7.90; N, 5.34.

EXAMPLE 19

2-(3,5-di-t-butyl-4-hydroxyphenyl)-4-(2-(4-(1-dimethylaminoethyl)phenyloxy)ethyl)oxazole hydrochloride monohydrate A. Preparation of 2-(3,5-di-t-butyl-4-hydroxyphenyl)-4-(2-(4-acetylphenyloxy)ethyl)oxazole To a stirred solution of 10 g (31.5 mmole) of the compound of Example 1C above, in tetrahydrofuran (95 ml) was added 4-hydroxyacetophenone (4.29 g, 31.5 mmole) and triphenylphosphine (9.09 g, 34.7 mmole). After cooling to −20° C., a solution of diethylazodicarboxylate (5.5 ml, 34.7 mmole) in tetrahydrofuran (31 ml) was added dropwise over 15 min. The reaction was allowed to warm to room temperature and stir for 2.5 hours, at which time it was diluted with diethyl ether and extracted with water and brine. The organic layer was dried over sodium sulfate, evaporated to dryness, and chromatographed on silica gel using a toluene-ethyl acetate gradient to give the subtitled compound (8.5 g, 62%):

$^1$H NMR (CDCl$_3$) δ 7.95 (d, J=9 Hz, 2H), 7.85 (s, 2H), 7.5 (s, 1H), 6.95 (d, J=9 Hz, 2H), 5.5 (s, 1H), 4.35 (t, J=7 Hz, 2H), 3.1 (t, J=7 Hz, 2H), 2.55 (s, 3H), 1.5 (s, 18H);

FDMS 435 (M$^+$).

B. Preparation of 2-(3,5-di-t-butyl-4-hydroxyphenyl)-4-(2-(4-(1-dimethylaminoethyl)phenyloxy)ethyl)oxazole hydrochloride Title compound was prepared substantially in accordance with the procedure in Example 1E above using the compound of Step A, 1.23 g (19.5 mmole) of sodium cyanoborohydride and dimethylamine (19.4 ml, 293 mmole), heating to 60° C. for 24 hours. The organic layer was chromatographed on silica gel using a methylene chloride/methanol gradient to give the free base which was dissolved in methylene chloride, treated with hydrogen chloride gas, and evaporated to give 8.31 g (80%) of the title product.

$^1$H NMR (CDCl$_3$) δ 11.6 (bs, 1H), 8.05 (s, 2H), 7.6 (s, 1H), 7.45 (d, J=9 Hz, 2H), 6.95 (d, J=9 Hz, 2H), 5.8 (s, 1H), 4.4 (t, J=7 Hz, 2H), 4.15 (m, 1H), 3.25 (t, J=7 Hz, 2H), 2.7 (d, J=4 Hz, 3H), 2.55 (d, J=4 Hz, 3H), 1.85 (d, J=7 Hz, 3H), 1.5 (s, 18H);

FDMS 464 (M$^+$-HCl);

Elemental analysis for C$_{29}$H$_{41}$ClN$_2$O$_3$.H$_2$O: Calculated: C, 67.10; H, 8.35; N, 5.40. Found: C, 67.00; H, 8.04; N, 5.24.

EXAMPLE 20

2-(3,5-di-t-butyl-4-hydroxyphenyl)-4-(2-(4-N-methyl-N-ethylaminomethyl-3-methylphenoxy)ethyl)oxazole hydrochloride hydrate A. Preparation of 3-methyl-allyloxybenzene m-Cresol 10.4 ml (100 mmole), 10.8 ml (125 mmole) allyl bromide, and 16.56 g (120 mmole) of potassium carbonate were stirred in 50 ml of acetone and refluxed, with stirring, under nitrogen, for 18 hours. The reaction was cooled, the insoluble inorganics were filtered off and the filtrate was stripped to give 14.0 g (95%) of subtitled product, which was used without further purification.

NMR (CDCl$_3$), δ 2.33 (s, 3H), 4.51–4.54 (m, 2H), 5.26–5.45 (m, 2H), 6.00–6.13 (m, 1H), 6.72–6.78 (m, 2H), 7.17 (t, 1H, J=9 Hz)

B. Preparation of 4-allyloxy-2-methylbenzaldehyde

N-methyl formanilide 19.4 ml (158 mmole), was chilled to 13° C., where it began to solidify. Phosphorus oxychloride, 13.7 ml (147 mmole), was added with stirring, under nitrogen. After 25 minutes, the temperature was 45° C. and the reaction had again begun to solidify. The compound of Step A, 14 g (95 mmole), was added and the mixture was stirred and heated in a 70° C. oil bath. The reaction exothermed to 95° C. Stirring was continued under nitrogen for 30 minutes. The bath was removed and when the temperature reached 35° C., the mixture was dissolved in chloroform. Ice was added and the layers were separated and washed once with water, twice with saturated sodium bicarbonate, once again with water and once with brine. The organic layer was chromatographed on 450 ml silica, eluting with chloroform to give 13.54 g (81%) of subtitled product which was used without further purification.

NMR (CDCl$_3$), δ 2.64 (s, 3H), 4.61 (m, 2H), 5.30–5.49 (m, 2H), 6.00–6.12 (m, 1H), 6.74–6.87 (m, 2H), 7.73 (m, 1H), 10.11 (s, 1H)

C. Preparation of 2-methyl-4-hydroxybenzaldehyde

The compound of Step B, 13.54 g (76.9 mmole), 1.72 g (7.69 mmole) palladium acetate, and 12.09 g (46.2 mmole) triphenylphosphine were mixed in a 250 ml flask. Formic acid, 3.2 ml (84.6 mmole), was added and the reaction was swirled. Within 15 seconds, the reaction foamed, exothermed and formed a gum which was dissolved in ethyl acetate, washed once with sodium bicarbonate and once with brine. The organic layer was chromatographed on 350 ml silica, eluting with 20%, then 40% ethyl acetate/hexane. The fractions were combined and the product crystallized from methylene chloride/hexane to give 3.61 g (35%) of product which was used without further purification.

NMR (CDCl$_3$), δ 2.50 (s, 3H), 6.70 (d, 1H, J=2 Hz), 6.78 (dd, 1H, J=2 Hz,9 Hz), 7.75 (d, 1H, J=9 Hz), 10.36 (s, 1H)

D. Preparation of 2-(3,5-di-t-butyl-4-hydroxyphenyl)-4-(2-(4-formyl-3-methylphenyloxy)ethyl)oxazole Subtitled compound was prepared from 8.0 g (25.2 mmole) of the compound of Example 1C substantially in accordance with the procedure in Example 4A using 3.61 g (26.5 mmole) of the compound of Step C, 6.62 g (25.2 mmole) triphenylphosphine and 3.97 ml (25.2 mmol) diethylazodicarboxylate. The crude product was chromatographed on silica eluting with methylene chloride. The appropriate fractions were bulked and stripped to give 5.05 g (46%) of subtitled product which was used without further purification.

NMR (CDCl$_3$), δ 1.48 (s, 18H), 2.64 (s, 3H, J=5 Hz), 3.11 (t, 2H, J=5 Hz), 4.35 (t, 2H, J=5 Hz), 5.54 (s, 1H), 6.77 (d,

1H, J=2 Hz), 6.86 (dd, 1H, J=2 Hz,9 Hz), 7.51 (s, 1H), 7.74 (d, 1H, J=9 Hz), 7.86 (s, 1H), 10.11 (s, 1H)

E. Preparation of 2-(3,5-di-t-butyl-4-hydroxyphenyl)-4-(2-(4-N-methyl-N-ethylaminomethyl-3-methylphenoxy)ethyl) oxazole hydrochloride hydrate Title compound was prepared from 4.54 g (10.4 mmole) of the compound of Step D substantially in accordance with the procedure of Example 1E above using 8.9 ml (104 mmole) of methylethylamine, 5.59 ml (104 mmole) of acetic acid and 693 mg (11 mmole) of sodium cyanoborohydride. Such reaction provided 1.89 g. (35%) of title product as a white foam.

FDMS-M$^+$ 478;

Elemental analysis for ($C_{30}H_{42}N_2O_3$·HCl·0.75 $H_2O$): Calculated: C, 68.02; H, 8.48; N, 5.35 Found: C, 68.16; H, 8.48; N, 5.30

NMR ($CDCl_3$), δ 1.41 (t, 3H, J=7 Hz), 1.48 (s, 18H), 2.41 (s, 3H), 2.65 (d, 2H, J=5 Hz), 2.96 (m, 1H), 3.24 (m, 2H), 4.07–4.27 (m, 3H), 5.84 (s, 1H), 6.80 (m, 2H), 7.63 (m, 2H), 8.07 (s, 2H)

EXAMPLE 21

2-(3,5-di-t-butyl-4-hydroxyphenyl)-4-(2-(3-chloro-4-N-methyl-N-ethylaminomethylphenoxy)ethyl) oxazole hydrochloride hemihydrate A. Preparation of 2-(3,5-di-t-butyl-4-hydroxyphenyl)-4-(2-(3-chloro-4-formylphenoxy)ethyl)oxazole Subtitled compound was prepared from 6.34 g (20 mmole) of the compound of Example 1C substantially in accordance with the procedure in Example 4A using 3.60 g (23 mmole) of 2-chloro-4-hydroxybenzaldehyde, 6.03 g (23 mmole) of triphenylphosphine and 3.62 ml (23 mmole) diethylazodicarboxylate. The crude product was chromatographed, eluting with methylene chloride. The appropriate fractions were bulked and stripped to give 5.64 g (62%) of subtitled product which was used without further purification.

NMR ($CDCl_3$), δ 1.48 (s, 18H), 3.09 (t, 2H, J=7 Hz), 4.35 (t, 2H, J=7 Hz), 5.52 (s, 1H), 6.90, (dd, 1H, J=2 Hz, 9 Hz), 6.97 (d, 1H, J=2 Hz), 7.49 (s, 1H), 7.84 (s, 2H), 7.87 (d, 1H, J=9 Hz), 10.32 (s, 1H)

B. Preparation of 2-(3,5-di-t-butyl-4-hydroxyphenyl)-4-(2-(3-chloro-4-N-methyl-N-ethylaminomethylphenoxy) ethyl) oxazole hydrochloride hemihydrate Title compound was prepared from 4.58 g (10 mmole) of the compound of Step A substantially in accordance with the procedure in Example 1E above using 6.54 ml (100 mmole) of methylethylamine, 5.75 ml (100 mmole) acetic acid and 661 mg (10.5 mmole) of sodium cyanoborohydride. Such reaction provided 1.24 g. (23%) of title product as a white foam.

FDMS-M$^+$ 498;

Elemental analysis for ($C_{29}H_{39}N_2O_3$Cl·HCl·0.5 $H_2O$): Calculated: C, 63.96; H, 7.59; N, 5.14 Found: C, 63.83; H, 7.83; N, 5.10

NMR ($CDCl_3$), δ 1.47 (s, 21H), 2.65 (d, 3H, J=5 Hz), 2.99 (m, 1H), 3.13 (t, 2H, J=7 Hz), 3.23 (m, 1H), 4.20–4.40 (m, 4H), 5.62 (s, 1H), 6.94 (d, 1H, J=9 Hz), 6.98 (s, 1H), 7.53 (s, 1H), 7.91 (s, 2H), 8.05 (d, 1H, J=9 Hz)

EXAMPLE 22

2-(3,5-di-t-butyl-4-hydroxyphenyl)-4-(2-(3-hydroxy-4-N-methyl-N-ethylaminomethylphenoxy)ethyl) oxazole hydrochloride hemihydrate A. Preparation of 2-(3,5-di-t-butyl-4-hydroxyphenyl)-4-(2-(3-hydroxy-4-formylphenoxy)ethyl)oxazole Subtitled compound was prepared from 12.68 g (40 mmole) of the compound of Example 1C substantially in accordance with the procedure in Example 4A above using 6.35 g (46 mmole) of 2,4-dihydroxybenzaldehyde, 12.05 g (46 mmole) of triphenylphosphine and 7.24 ml (46 mmole) diethylazodicarboxylate. The crude product was chromatographed on silica, eluting with methylene chloride. The appropriate fractions were combined and stripped of solvent to give 9.2 g (53%) of subtitled product which was used without further purification.

NMR ($CDCl_3$), δ 1.49 (s, 18H), 3.09 (t, 2H, J=5 Hz), 4.33 (t, 2H, J=5 Hz), 5.51 (s, 1H), 6.47 (d, 1H, J=2 Hz), 6.55 (dd, 1H, J=2 Hz, 9 Hz), 7.42 (d, 1H, J=9 Hz), 7.50 (s, 1H), 7.84 (s, 2H), 9.71 (s, 1H), 11.47 (s, 1H)

B. Preparation of 2-(3,5-di-t-butyl-4-hydroxyphenyl)-4-(2-(3-hydroxy-4-N-methyl-N-ethylaminomethylphenoxy) ethyl)oxazole hydrochloride hemihydrate Title compound was prepared from 3.18 g (7.28 mmole) of the compound of Step A substantially in accordance with the procedure in Example 1E above using 4.76 ml (72.8 mmole) methylethylamine, 4.16 ml (72.8 mmole) acetic acid and 481 mg (7.64 mmole) of sodium cyanoborohydride and the reaction was allowed to proceed for 2 days. Such reaction provided 1.23 g. (33%) of the title product as a white foam.

FDMS-M+ 480;

Elemental analysis for ($C_{29}H_{40}N_2O_4$·HCl·0.5 $H_2O$) Calculated: C, 66.21; H, 8.05; N, 5.32 Found: C, 66.01; H, 8.49; N, 5.09

NMR ($CDCl_3$), δ 1.41 (t, 3H, J=7 Hz), 1.48 (s, 18H), 2.65 (d, 2H, J=5 Hz), 2.96 (m, 1H), 3.24 (m, 2H), 4.07–4.27 (m, 3H), 6.01 (s, 1H), 6.36 (d, 1H, J=9 Hz), 6.94 (d, 1H, J=2H), 7.26 (m, 1H), 7.84 (s, 1H), 8.13 (s, 2H), 10.75 (bs, 1H)

EXAMPLE 23

2-(3,5-di-t-butyl-4-hydroxyphenyl)-4-(2-(4-N-methyl-N-ethylaminomethyl-3,5-dimethylphenyloxy)ethyloxazole hydrochloride hydrate A. Preparation of 3,5-dimethyl-allyloxy benzene 3,5-Dimethylphenol, 12.2 g (100 mmole), 10.8 ml (125 mmole) of allyl bromide, and 16.56 g (120 mmole) of potassium carbonate was dissolved and then refluxed in 50 ml acetone, with stirring, under nitrogen for 18 hours. The reaction was cooled, the insoluble inorganics were filtered off and stripped to give 16.2 g (100%) of subtitled product, which was used without further purification.

NMR ($CDCl_3$), δ 2.29 (s, 6H), 4.50 (m, 2H), 5.25–5.44 (M, 2H), 5.99–6.12 (m, 1H), 6.56 (s, 2H), 6.60 (s, 1H)

B. Preparation of 4-allyloxy-2,6-dimethyl-benzaldehyde

N-methyl formanilide, 20.5 ml (166 mmole), was chilled to 13°, where it began to solidify. Phosphorus oxychloride, 14.4 ml (155 mmole), was added with stirring, under nitrogen. After 25 minutes, the temperature was 45°. 3,5-Dimethyl-allyloxy benzene, 16.2 g (100 mmole), prepared as described above, was added with stirring and heated in a 70° C. oil bath. The reaction exothermed to 93° C. and was stirred under nitrogen for 30 minutes. The bath was removed and when the temperature reached 35°, the product was dissolved in chloroform. Ice was added, the layers were separated and washed once with water, twice with sodium bicarbonate, once with water and once with brine. The product was chromatographed down 500 ml of silica, eluting with chloroform to give 9.67 g (51%) of subtitled product which was used without further purification.

NMR ($CDCl_3$), δ 2.60 (s, 6H), 4.59 (m, 2H), 5.29–5.45 (m, 2H), 6.01–6.11 (m, 1H), 6.60 (s, 2H), 10.47 (s, 1H)

C. Preparation of 2,6-dimethyl-4-hydroxy-benzaldehyde

4-Allyloxy-2,6-dimethyl-benzaldehyde, 9.67 g (50.9 mmole), 1.14 g (5.09 mmole) of palladium II acetate, and 8.00 g (30.5 mmole) of triphenylphosphine was mixed in a flask. Formic acid, 2.11 ml (56 mmole), was added and the mixture was swirled in a 80° oil bath. Within 15 seconds the reaction exothermed and turned very dark. The gum was dissolved in ethyl acetate, washed once in sodium bicarbonate, once in water, and once in brine then chromatographed on 350 ml silica, using 20%, then 40% ethyl acetate/hexane. Fractions were bulked and crystallize from methylene chloride/hexane to give 3.90 g (51%) of subtitled product which was used without further purification.

NMR (CDCl$_3$), δ 2.64 (s, 6H), 6.74 (s, 2H), 7.26 (bs, 1H), 10.09 (s, 1H)

D. Preparation of 2-(3,5-di-t-butyl-4-hydroxyphenyl)-4-(2-(4-formyl-3,5-dimethylphenyloxy)ethyl)oxazole Title compound was prepared from 7.85 g (24.8 mmole) of the compound of Example 1C substantially in accordance with the procedure in Example 4A above using 3.9 g (26 mmole) 2,6-dimethyl-4-hydroxybenzaldehyde, 6.49 g (24.8 mmole) triphenylphosphine and 3.90 ml (24.8 mmole) diethylazodicarboxylate. The reaction was stirred under nitrogen for 18 hours. Hydrogen peroxide, 1.38 ml 30%, was added and the reaction was stirred for an additional 30 minutes, stripped, dissolved in 40 ml methylene chloride and placed in the freezer. The diethoxycarbonylhydrazine was then filtered off and the filtrate was chromatographed, eluting with methylene chloride. The appropriate fractions were bulked and stripped to give 6.73 g (60%) of subtitled product which was used without further purification.

NMR (CDCl3), δ 1.48(s, 18H), 2.59 (s, 6H), 3.12 (t, 2H, J=9 Hz), 4.34 (t, 2H, J=9 Hz), 5.58 (s, 1H),6.61 (s, 2H), 7.52 (s, 1H), 7.89 (s, 2H), 10.47 (s, 1H)

E. Preparation of 2-(3,5-di-t-butyl-4-hydroxyphenyl)-4-(2-(4-N-methyl-N-methylaminomethyl-3,5-dimethylphenyloxy)ethyl)oxazole hydrochloride monohydrate Title compound was prepared substantially in accordance with the procedure in Example 1E above using 5.02 g (11.2 mmole) of 2-(3,5-di-t-butyl-4-hydroxyphenyl)-4-(2-(4-formyl-3,5-dimethylphenyloxy)ethyl)oxazole, 9.59 ml (112 mmole) methylethyl amine, 6.40 ml (112 mmole) acetic acid, and 741 mg (11.76 mmole) sodium cyanoborohydride. Ethyl acetate was added and the mixture was washed once with water, once with saturated sodium bicarbonate, twice with water and once with brine. The mixture was dried, stripped of organics and chromatographed, eluting with methylene chloride/methanol 92:8. Fractions were bulked, stripped of organics and dissolved in methylene chloride/isopropyl ether. Hydrogen chloride gas was bubbled through the solution and the mixture was concentrated and triturated with isopropyl ether to give 4.47 g (69%) white foam.

FDMS-M+ 492;

Elemental Analysis for C31H44N2O3.HCl.H2O Calculated: C, 68.05; H, 8.66; N; 5.12 Found: C, 68.06; H, 8.84; N, 4.77

NMR (CDCl3), δ 1.49 (s, 18H), 1.55 (t, 3H, 5 Hz),2.48 (s, 6H), 3.23 (m, 2H), 3.36 (m,t, 2H, J=5 Hz), 3.98 (m, 1H), 4.30–4.40 (m,3H), 6.05 (s, 1H), 6.66 (s, 2H), 7.73 (s, 1H), 8.22 (s, 2H), 11.20 (bs, 1H)

EXAMPLE 24

2-(3,5-di-t-butyl-4-hydroxyphenyl)-4-(2-(4-N-methyl-N-ethylaminomethyl-2-chlorophenyloxy)ethyl)oxazole hydrochloride A. Preparation of 2-(3,5-di-t-butyl-4-hydroxyphenyl)-4-(2-(4-formyl-2-chlorophenyloxy)ethyl)oxazole Subtitled compound was prepared from 3.17 g (10 mmole) of compound of Example 1C, 1.72 g (11 mmole) 3-chloro-4-hydroxy-benzaldehyde, 2.62 g (10 mmole) triphenylphosphine and 1.57 ml (10 mmole) diethylazodicarboxylate substantially in accordance with the procedure in Example 4A above. The reaction was chromatographed, eluting with 4% methanol/methylene chloride. The appropriate fractions were bulked and stripped to give 3.51 g (77%) product which was used without further purification.

NMR (CDCl$_3$), δ 1.48 (s, 18H), 3.17 (t, 2H, J=7 Hz), 4.42 (t, 2H, J=7 Hz), 5.51 (s, 1H), 7.08 (d, 1H, J=9 Hz), 7.61 (s, 1H), 7.75 (dd, 1H, J=2 Hz,9 Hz), 7.84 (s, 2H), 7.90 (d, 1H, J=2 Hz), 9.84 (s, 1H)

B. Preparation of 2-(3,5-di-t-butyl-4-hydroxyphenyl)-4-(2-(4-N-methyl-N-ethylaminomethyl-2-chlorophenyloxy)ethyl)oxazole hydrochloride Title compound was prepared from 1.75 g of the compound of Step A substantially in accordance with the procedure in Example 9, using 0.66 ml (7.7 mmole) methylethylamine, 2.28 ml (7.7 mmole) titanium IV isopropoxide and 220 mg (5.74 mmole) sodium borohydride except that the reduction was stirred for 18 hours. Ammonia (6.3 ml, 2N) was added to give a thick suspension. Methylene chloride and diatomaceous earth were added and the suspension was filtered through diatomaceous earth. The filtrate was washed once with brine, dried and the organics stripped and chromatographed, eluting with methylene chloride/methanol/concentrated ammonia 90:5:0.5. The fractions were bulked, stripped of solvent and dissolved in methylene chloride/isopropyl ether. Hydrogen chloride gas was bubbled in and the material was concentrated and triturated with isopropyl ether to give 1.21 g (59%) white foam.

FDMS-M$^+$ 498;

Elemental analysis for C$_{29}$H$_{39}$N$_2$O$_3$Cl.HCl Calculated: C, 65.04; H, 7.53; N, 5.23 Found: C, 65.30; H, 7.72; N, 5.22

NMR (CDCl$_3$), δ 1.48 (m, 21H), 2.63 (d, 3H, J=5 Hz), 2.88–2.92 (m, 1H), 3.15 (m, 3H, J=5 Hz), 3.97–4.16 (m, 2H), 4.34 (t, 2H, J=5 Hz), 5.53 (s, 1H), 7.03 (d, 1H, J=9 Hz), 7.48 (d, 1H, J=2 Hz), 7.60 (s, 1H), 7.65 (dd, 1H, J=2 Hz,9 Hz), 7.85 (s, 1H)

EXAMPLE 25

2-(3,5-di-t-butyl-4-hydroxyphenyl)-4-(2-(4-N-methyl-N-ethylaminomethyl-1-napthyloxy)ethyl) oxazole hydrochloride hemihydrate A. Preparation of 2-(3,5-di-t-butyl-4-hydroxyphenyl)-4-(2-(4-formyl-1-napthyloxy)ethyl)oxazole Subtitled compound was prepared from 7.925 g (25 mmole) of the compound of Example 1C substantially in accordance with the procedure in Example 4A using 4.95 g (28.75 mmole) of 4-hydroxy-1-napthaldehyde, 7.53 g (28.75 mmole) of triphenylphosphine and 4.52 ml (28.75 mmole) diethylazodicarboxylate. The crude product was chromatographed with methylene chloride. The appropriate fractions were bulked and stripped to give 4.08 g (35%) product which was used without further purification.

NMR (CDCl$_3$), δ 1.48 (s, 18H), 3.26 (t, 2H, J=6 Hz), 4.57 (t, 2H, J=6 Hz), 5.51 (s, 1H), 6.97 (d, 1H, J=9 Hz), 7.56 (m, 2H), 7.69 (t, 1H, J=9 Hz), 7.85 (s, 1H), 7.91 (d, 1H, J=9 Hz), 8.33 (d, 1H, J=9 Hz), 9.30 (d, 1H, J=9 Hz), 10.20 (s, 1H)

B. Preparation of 2-(3,5-di-t-butyl-4-hydroxyphenyl)-4-(2-(4-N-methyl-N-ethylaminomethyl-1-napthyloxy)ethyl) oxazole hydrochloride hemihydrate Title compound was prepared from 3.41 g (7.24 mmole) of the compound of Step A substantially in accordance with the procedure in Example 1E above using 4.74 ml (72.4 mmole) of methylethylamine, 4.14 ml (12.4 mmol) acetic acid and 480 mg (7.6 mmole) of sodium cyanoborohydride. The crude product was chromatographed eluting with a gradient of methylene chloride/methanol/1% concentrated ammonia 100:0:00 to 90:10:1 over 10 minutes. Crude product was dissolved in methylene chloride/isopropyl ether, treated with hydrogen chloride gas and the resulting oil triturated with isopropyl ether to give 1.84 g (46%) white foam.

FDMS-M$^+$ 514;

Elemental analysis for $C_{33}H_{42}N_2O_3 \cdot HCl \cdot 0.5\ H_2O$ Calculated: C, 70.76; H, 7.92; N, 5.00 Found: C, 70.52; H, 8.22; N, 4.72

NMR (CDCl$_3$), δ 1.13 (t, 3H, J=6 Hz), 1.49 (s, 18H), 2.65 (d, 2H, J=5 Hz), 2.96 (m, 1H), 3.24 (m, 1H), 3.58 (m, 2H), 4.07–4.27 (m, 3H), 6.01 (s, 1H), 6.97 (d, 1H, J=9 Hz), 7.56 (t, 1H, J=9H), 7.69 (t, 1H, J=9 Hz), 7.82 (m, 2H), 8.14 (d, 1H, J=9 Hz), 8.24 (m, 3H)

EXAMPLE 26

2-(3,5-di-t-butyl-4-hydroxyphenyl)-4-(2-(4-(morpholin-4-yl-methyl)phenyloxy)ethyl)oxazole hydrochloride Title compound was prepared from the compound of Example 1D (4.21 g, 10 mmole) substantially in accordance with the procedure in Example 1E using morpholine (8.72 ml, 10 mmole) and sodium cyanoborohydride (0.63 g, 10 mmole). The methanol was evaporated and the residue was dissolved in ethyl acetate and saturated sodium bicarbonate. The organic layer was extracted with brine, dried with sodium sulfate, evaporated to dryness, and chromatographed on silica gel using a hexane-isopropanol gradient to give the free base (3.68 g, 75%). The free base was dissolved in methylene chloride, treated with hydrogen chloride gas, and evaporated to give desired product (3.68 g, 93%).

$^1$H NMR (CDCl$_3$) δ 10.95 (bs, 1H), 7.9 (s, 2H), 7.6 (s, 1H), 7.5 (d, J=9 Hz, 2H), 6.95 (d, J=9 Hz, 2H), 5.5 (s, 1H), 4.25 (m, 4H), 4.1 (d, J=5 Hz, 2H), 3.9 (dd, J=10, 3 Hz, 2H), 3.25 (d, J=10 Hz, 2H), 3.05 (t, J=7 Hz, 2H), 2.9 (m, 2H), 1.5 (s, 18H);

FDMS 492 (M$^+$-HCl);

Elemental analysis for $C_{30}H_{41}ClN_2O_4$: Calculated: C, 68.10; H, 7.81; N, 5.29. Found: C, 67.93; H, 7.73; N, 5.17.

EXAMPLE 27

2-(3,5-di-t-butyl-4-hydroxyphenyl)-4-(2-(4-(4-methylpiperazin-1-yl-methyl)phenyloxy)ethyl)oxazole dihydrochloride Title compound was prepared from 5.05 g (12 mmole) of the compound of Example 1D substantially in accordance with the procedure in Example 1E above using N-methylpiperazine (13.3 ml, 120 mmole) and sodium cyanoborohydride (0.75 g, 12 mmole). The methanol was evaporated and the residue was dissolved in ethyl acetate and saturated sodium bicarbonate. The organic layer was extracted with brine, dried with sodium sulfate, evaporated to dryness, and chromatographed on silica gel using a methylene chloride/methanol gradient to give the free base (4.53 g, 75%). The free base was dissolved in methylene chloride, treated with hydrogen chloride gas, and evaporated to give desired product (4.53 g, 87%).

$^1$H NMR (CDCl$_3$) δ 7.95 (s, 2H), 7.55 (d, J=9 Hz, 2H), 7.5 (s, 1H), 6.95 (d, J=9 Hz, 2H), 5.5 (s, 1H), 4.3 (t, J=7 Hz, 2H), 4.15 (s, 2H), 3.9 (m, 2H), 3.75 (m, 2H), 3.45 (m, 4H), 3.05 (t, J=7 Hz, 2H), 2.9 (s, 3H), 1.5 (s, 18H);

FDMS 505 (M$^+$-HCl);

Elemental analysis for $C_{31}H_{45}Cl_2N_3O_3$: Calculated: C, 64.35; H, 7.84; N, 7.26. Found: C, 64.07; H, 7.67; N, 7.32.

EXAMPLE 28

2-(3,5-di-t-butyl-4-hydroxyphenyl)-4-(2-(4-(4-acetylpiperazin-1-yl-methyl)phenyloxy)ethyl)oxazole hydrochloride Title compound was prepared from the compound of Example 1D (4.21 g, 10 mmole) substantially in accordance with the procedure in Example 1E using N-acetylpiperazine (12.82 g, 100 mmole) and sodium cyanoborohydride (0.63 g, 10 mmole). The methanol was evaporated and the residue was dissolved in ethyl acetate and saturated sodium bicarbonate. The organic layer was extracted with brine, dried with sodium sulfate, evaporated to dryness, and chromatographed on silica gel using a methylene chloride/methanol gradient to give the free base (3.96 g, 74%). The free base was dissolved in methylene chloride, treated with hydrogen chloride gas, and evaporated to give desired product (3.94 g, 93%).

$^1$H NMR (CDCl$_3$) δ 10.8 (bs, 1H), 7.95 (s, 2H), 7.55 (d, J=9 Hz, 2H), 7.5 (s, 1H), 6.95 (d, J=9 Hz, 2H), 5.6 (s, 1H), 4.7 (d, J=13 Hz, 1H), 4.35 (t, J=7 Hz, 2H), 4.15 (m, 2H), 3.85 (d, J=13 Hz, 1H), 3.45 (m, 4H), 3.15 (t, J=7 Hz, 2H), 2.65 (m, 2H), 2.1 (s, 3H), 1.5 (s, 18H);

FDMS 533 (M$^+$-HCl);

Elemental analysis for $C_{32}H_{44}ClN_3O_4 \cdot 1.2\ H_2O$: Calculated: C, 64.95; H, 7.90; N, 7.10. Found: C, 64.67; H, 7.51; N, 6.97.

EXAMPLE 29

2-(3,5-di-t-butyl-4-hydroxyphenyl)-4-(2-(4-thiomorpholinylmethylphenoxy)ethyl)oxazole Title product was prepared from the compound of example 1D substantially in accordance with the procedure in Example 11, except using thiomorpholine, and conducting the reaction at room temperature. The material was eluted with 0 to 3% (1% ammonium hydroxide:methanol) :chloroform gradient over a thirty minute period. Fractions containing desired product were concentrated in vacuo to an oil. The oil was treated with chloroform and saturated with hydrogen chloride gas. This solution was concentrated in vacuo to afford 3.64 g of the title compound. 1.50 g of this material was taken up into solution with tetrahydrofuran (20 ml), the solution was boiled down to approximately 10 ml, additional tetrahydrofuran (20 ml) was added and the crystals were collected by filtration. Crystals were dried in a vacuum oven overnight at 60° C. to afford 1.27 g of the title compound.

Mass Spectrum(FDMS): m/z 508 (M-HCl).

$^1$H NMR (CDCl$_3$): δ 8.24 (s, 2H), 7.71 (s, 1H), 7.53 (d, J=8.6 Hz, 2H), 6.96 (d, J=8.6 Hz, 2H), 6.07 (s, 1H), 4.46 (t J=5.7 Hz, 2H), 4.08 (t, J=5.7 Hz, 2H), 3.66 (m, 4H), 3.39 (t, J=5.7 Hz, 2H), 2.87 (m, 2H), 2.58 (m, 2H), 1.50 (s, 18H).

Elemental analysis for $C_{30}H_{41}ClN_2O_3S$: Calculated: C, 66.09; H, 7.58; N, 5.14. Found: C, 66.36; H, 7.82; N, 4.85.

EXAMPLE 30

2-(3,5-di-t-butyl-4-hydroxyphenyl)-4-(2-(4-(piperazin-1-yl-methyl)phenoxy)ethyl)oxazole dihydrochloride hydrate 2-(3,5-di-t-butyl-4-hydroxyphenyl)-4-(2-(4-(4-acetylpiperazin-1-yl-methyl)phenoxy)ethyl)oxazole hydrochloride prepared as described in Example 28 above (0.97 g, 1.82 mmole) was dissolved in 4N hydrochloric acid and stirred for 1.5 hours at 80° C. The reaction was then diluted with ethyl acetate and neutralized with saturated sodium bicarbonate. The organic layer was extracted with brine, dried over sodium sulfate, evaporated to dryness, and chromatographed on silica gel using a methylene chloride/methanol/ammonium hydroxide gradient to give the free base (0.67 g, 75%). The free base (1.29 g, 2.62 mmol) was dissolved in methylene chloride, treated with hydrogen chloride gas, and evaporated to give desired product (1.35 g, 91%).

$^1$H NMR (CDCl$_3$) δ 10.15 (bs, 1H), 9.95 (bs, 1H), 7.95 (s, 2H), 7.55 (m, 3H), 6.95 (m, 2H), 5.7 (s, 1H), 4.4 (bs, 2H), 4.25 (bs, 2H), 4.0–3.8 (m, 8H), 3.1 (bs, 2H), 1.5 (s, 18H);

FD MS 491 (M$^+$-HCl);

Elemental analysis for C$_{30}$H$_{43}$Cl$_2$N$_3$O$_3$1.4 H$_2$O: Calculated: C, 61.09; H, 7.83; N, 7.12. Found: C, 60.71; H, 7.43; N, 7.02.

EXAMPLE 31

2-(3,5-di-t-butyl-4-hydroxyphenyl)-4-(2-(4-(imidazol-1-yl-methyl)phenoxy)ethyl)oxazole hydrochloride monohydrate A. Preparation of N-p-methoxybenzylimidazole To a stirred solution of imidazole (25.53 g, 375 mmole) in acetonitrile (625 ml) was added p-methoxybenzyl chloride (16.95 ml, 125 mmole). The reaction was refluxed for 16 hours, evaporated to dryness, and redissolved in methylene chloride and saturated sodium bicarbonate. The organic layer was extracted with water twice. Standard acid/base workup gave N-p-methoxybenzylimidazole (16.3 g, 69%) which was used without further purification:

$^1$H NMR (CDCl$_3$) δ 7.5 (bs, 1H), 7.1 (m, 3H), 6.9 (m, 3H), 5.0 (s, 2H), 3.8 (s, 3H).

B. Preparation of N-p-hydroxybenzylimidazole

To a stirred solution of the compound of Step A (16.3 g, 86.1 mmole) in methylene chloride (860 ml) cooled to 5° C., was added boron tribromide (32.6 ml, 344.4 mmole) dropwise over 15 minutes. After 2 hours at 5° C., the reaction was quenched with methanol dropwise, evaporated to dryness, and redissolved in methanol, water, and methylene chloride The pH was adjusted to 8.4 with sodium hydroxide. The organic layer was dried over sodium sulfate and evaporated to dryness to give N-p-hydroxybenzylimidazole (13.6 g, 91%) which was used without further purification:

$^1$H NMR (DMSO-d$_6$) δ 9.5 (bs, 1H), 7.7 (bs, 1H), 7.1 (m, 3H), 6.9 (bs, 1H), 6.75 (d, J=9 Hz, 2H), 5.05 (s, 2H);

FD MS 174 (M$^+$).

C. Preparation of 2-(3,5-di-t-butyl-4-hydroxyphenyl)-4-(2-(4-(imidazol-1-ylmethyl)phenoxy)ethyl)oxazole hydrochloride monohydrate Title compound was prepared from the compound of Example 1C (24.75 g, 78.1 mmole) substantially in accordance with the procedure in Example 4A using the compound of Step B, (13.6 g, 78.1 mmole), and triphenylphosphine (22.5 g, 85.9 mmole). The filtrate was extracted with water and brine and the organic layer was dried over sodium sulfate, evaporated to dryness, chromatographed on silica gel using a methylene chloride-isopropanol gradient, and triturated with hot diethyl ether to give the free base (2.51 g, 7%). The free base was dissolved in methylene chloride (65 ml), treated with hydrogen chloride gas, and evaporated to give desired product (2.63 g, 97%):

$^1$H NMR (CDCl$_3$) δ 9.5 (s, 1H), 8.0 (s, 2H), 7.6 (s, 1H), 7.3 (m, 3H), 7.1 (s, 1H), 6.95 (d, J=9 Hz, 2H), 5.8 (s, 1H), 5.4 (s, 2H), 4.35 (t, J=7 Hz, 2H), 3.2 (d, J=7 Hz, 2H), 1.5 (s, 18H);

FDMS 473 (M$^+$-HCl);

Elemental analysis for C$_{29}$H$_{36}$ClN$_3$O$_3$.H$_2$O: Calculated: C, 65.96; H, 7.25; N, 7.96. Found: C, 65.75; H, 7.07; N, 8.09.

EXAMPLE 32

2-(3,5-di-t-butyl-4-hydroxyphenyl)-4-(2-(4,5-dihydro-1H-imidazol-2-ylmethyl)phenoxy) ethyloxazole hydrochloride A. Preparation of 2-(3,5-di-t-butyl-4-hydroxyphenyl)-4-(2-(4-cyanomethylphenoxy)ethyl)oxazole To a suspension of the compound of Example 1C, 4-hydroxybenzyl cyanide, triphenylphosphine and 0.7M (mmole alcohol/ml tetrahydrofuran) reaction solution was added diethylazodicarboxylate. After stirring at 24° C. for approximately 24 hours, the reaction was concentrated in vacuo to a brown oil. Material was treated with chloroform (30 ml), triturated and the insolubles were filtered and washed with chloroform (20 ml). The filtrate was concentrated in vacuo to an oil, treated with toluene and subjected to preparatory chromatography. The material was eluted with 0 to 10% methanol/toluene gradient over a thirty minute period. Fractions containing the desired product were concentrated in vacuo to afford 12.18 g (88%) of the subtitled compound.

Mass Spectrum(FDMS): m/z 432 (M).

$^1$H NMR (DMSOd$_6$): δ 7.91 (s, 1H), 7.72 (s, 2H), 7.52 (bs, 1H), 7.25 (d, J=8.6 Hz, 2H), 6.98 (d, J=8.6 Hz, 2H), 4.24 (t, J=6.5 Hz, 2H), 3.93 (s, 2H), 2.97 (t, J=6.5 Hz, 2H), 1.41 (s, 18H).

Elemental analysis for C$_{27}$H$_{32}$N$_2$O$_3$: Calculated: C, 74.97; H, 7.46; N, 6.48. Found: C, 75.17; H, 7.41; N, 6.21.

B. Preparation of 2-(3,5-di-t-butyl-4-hydroxyphenyl)-4-(2-(4,5-dihydro-1H-imidazol-2-ylmethyl)phenoxy) ethyloxazole hydrochloride To a solution of Step A (24 mmole, 10.39 g) in ethanol (2 ml) and diethyl ether (50 ml) at −10° C. hydrogen chloride gas was bubbled through over a thirty minute period. Reaction was maintained at 0° C. After four days, the supernatant was decanted off then absolute ethanol (50 ml) and diethyl ether (50 ml) were added. The reaction was cooled to 0° C. then hydrogen chloride gas was passed through the solution for approximately four hours. After stirring at 0° C. for four hours, the reaction was concentrated in vacuo to a foam. Next, the foam was taken up into absolute ethanol (50 ml) then treated with ethylene diamine (48 mmole, 2.88 g). The resulting suspension was refluxed for approximately 32 hours, filtered hot and the insolubles washed with ethanol (20 ml). The filtrate was concentrated in vacuo to an oil. The oil was treated with chloroform (100 ml) and washed with saturated sodium bicarbonate (2×50 ml) and brine (1×50 ml). Organics were dried over sodium sulfate, filtered and concentrated in vacuo, to afford 8.38 g of a foam. Material was taken up into chloroform and chromatographed. The material was eluted with 10% (1% ammonium hydroxide/methanol):chloroform gradient over a thirty minute period. Remainder of the material was eluted with 10% (1% ammonium hydroxide/methanol) :chloroform. Fractions containing the desired product were concentrated in vacuo to a foam. Material was taken up into methylene chloride (100 ml) and washed with saturated sodium bicarbonate (2×50 ml) and (1×50 ml). Organics were dried over sodium sulfate, filtered, then hydrogen chloride gas was passed through the solution. This solution was concentrated in vacuo to afford a foam. A portion of the foam (1.26 g) was treated with methylene chloride (20 ml) and isopropyl ether (10 ml) then boiled down to approximately 20 ml total volume. The turbid solution was cooled at −10° C. for approximately one hour then decanted. The remaining oil was concentrated in vacuo to afford 1.08 g of a foam.

Mass Spectrum(FDMS): m/z 476 (M+1).

$^1$H NMR (CdCl$_3$): δ 7.85 (s, 2H), 7.55 (s, 1H), 7.47 (d, J=8.5 Hz, 2H), 6.78 (d, J=8.5 Hz, 2H), 5.59 (s, 1H), 4.19 (t, J=6.4 Hz, 2H), 3.96 (s, 2H), 3.80 (s, 4H), 3.04 (t, J=6.4 Hz, 2H), 1.46 (s, 18H).

Elemental analysis for C$_{29}$H$_{38}$ClN$_3$O$_3$OC$_6$H$_{14}$0: Calculated: C, 74.97; H, 7.46; N, 6.48. Found: C, 75.17; H, 7.41; N, 6.21.

EXAMPLE 33

6-[2-[(3,5-di-tert-butyl-4-hydroxyphenyl)-4-oxazolyl]ethoxy]-1,2,3,4-tetrahydroisoquinoline hydrochloride A. Preparation of N-tert-butoxycarbonyl-6-hydroxy-1,2,3,4-tetrahydroisoquinoline A suspension of 6-hydroxy-1,2,3,4-tetrahydroisoquinoline oxalate (0.17 mole, 40.04 g) in methanol (150 ml) and tetrahydrofuran (420 ml) was treated with diisopropylethylamine (0.38 mole, 48.50 g) then with a solution of di-tert-butyl dicarbonate (0.13 mole, 27.30 g) in tetrahydrofuran (10 ml). After stirring at room temperature for approximately 4 hours, the material was treated with methylene chloride (500 ml), brine (250 ml) and 10% aqueous sodium sulfate (250 ml). Phases were separated, the organic phase was washed with 10% aqueous sodium sulfate (3×250 ml), brine (1×250 ml) then dried over sodium sulfate, filtered and concentrated in vacuo to a solid. The material was treated with methylene chloride and chromatographed, eluting with 0 to 35% (ethyl acetate/hexane) gradient over a thirty minute period. Fractions containing the desired product were concentrated in vacuo to afford 27.63 g (66%) of the subtitled compound.

Mass Spectrum(FDMS): m/z 249 (M), 148 (M-101).

$^1$H NMR (DMSOd$_6$): δ 9.21 (s, 1H), 6.93 (d, 1H), 6.58 (dd, J=2.4, 8.1 Hz, 1H), 6.53 (d, J=2.4 Hz, 1H), 4.36 (s, 2H), 3.48 (t, J=5.9 Hz, 2H), 2.66 (t, J=5.9 Hz, 2H), 1.41 (s, 9H).

Elemental analysis for C$_{14}$H$_{19}$NO$_3$: Calculated: C, 67.45; H, 7.68; N, 5.62. Found: C, 67.74; H, 7.53; N, 5.59.

B. Preparation of 6-[2-[(3,5-di-tert-butyl-4-hydroxyphenyl)-4-oxazoylyl]ethoxy]-2-tert-butoxycarbonyl-1,2,3,4-tetrahydroisoquinoline The title compound was prepared substantially as described in Example 4A except using the compound of Step A and 0.7M reaction solution. At approximately 3.8 hours, the reaction was concentrated in vacuo to an oil. The oil was treated with methylene chloride (10 ml) and the insolubles were collected by filtration and washed with methylene chloride (10 ml). The filtrate was then treated with methylene chloride (25 ml), washed with 0.1N sodium hydroxide (3×50 ml) and 10% aqueous sodium sulfate (2×50 ml). organics were concentrated in vacuo to a foam, treated with ethyl acetate and subjected to preparatory chromatography. The material was eluted with 10 to 40% (ethyl acetate/hexane) gradient over a thirty minute period. Fractions containing title compound were combined, concentrated in vacuo, and chromatographed. Material was eluted with 10 to 25% acetone:hexane gradient over a thirty minute period. Fractions containing desired product were concentrated in vacuo to afford 5.60 g (56%) of the subtitled compound as a foam.

Mass Spectrum(FDMS): m/z 548 (M).

$^1$H NMR (DMSOd$_6$): δ 7.89 (s, 1H), 7.70 (s, 2H), 7.50 (s, 1H), 7.04 (d, 2H), 6.77 (m, 3H), 4.39 (s, 2H), 4.21(t, 2H), 3.48 (m, 2H), 2.93 (t, 2H), 2.70 (t, 2H), 1.39 (s, 27H).

C. Preparation of 6-[2-[(3,5-di-tert-butyl-4-hydroxyphenyl)-4-oxazolyl]ethoxy]-1,2,3,4-tetrahydroisoquinoline hydrochloride A solution of the compound of Step B (9.8 mmole, 5.60 g) in methylene chloride (33 ml) was treated with thiophenol (98.1 mmole, 10.81 g). The reaction was cooled to −10° C. then treated with trifluoroacetic acid (98.1 mmole, 8.26 g). After approximately 1.5 hours, the reaction was warmed to 24° C. After stirring 5.5 hours at 24° C., the reaction was concentrated in vacuo, treated with chloroform and chromatographed. Material was eluted with 0 to 10% (1% ammonium hydroxide/methanol):chloroform gradient over a fifteen minute period. Fractions containing desired product were reduced in volume, washed with water (50 ml), dried over sodium sulfate, filtered and concentrated in vacuo to afford an oil. Material was taken up into chloroform, then saturated with hydrogen chloride gas. This solution was concentrated in vacuo to afford 2.40 g of the title compound. This material was recystallized from 3:1 diisopropyl ether methylene chloride to afford 760 mg of the title compound.

Mass Spectrum(ion spray MS): m/z 449 (M+1).

$^1$H NMR (DMSOd$_6$): δ 7.91 (s, 1H), 7.72 (s, 2H), 7.55 (s, 1H), 7.12 (d, J=8.6 Hz, 2H), 6.85 (m, 3H), 4.23 (t, J=6.5 Hz, 2H), 4.15 (m, 2H), 3.32 (m, 2H), 2.96 (m, 4H), 1.41 (s, 18H).

EXAMPLE 34

6-[2-[(3,5-di-tert-butyl-4-hydroxyphenyl)-4-oxazoylyl]ethoxy]isoquinoline hydrochloride monohydrate Title compound was prepared from compound of Example 1C (19.1 mmole, 6.07 g), triphenylphosphine (21.1 mmole, 5.52 g) and 6-hydroxyisoquinoline (21.1 mmole, 3.07 g) in tetrahydrofuran (43 ml) at −10° C. (ice/acetone bath) was added diethylazodicarboxylate (21.1 mmole, 3.67 g) over an eleven minute period. After the addition was complete, the reaction was stirred at room temperature. At approximately 3.8 hours the reaction was concentrated in vacuo to an oil. The oil was taken up into chloroform then chromatographed. Material was eluted with 70–85% ethyl acetate/hexane gradient over a thirty minute period. Fractions containing desired product were combined, reduced in volume and chromatographed. Material was eluted with 0–15% methanol/toluene gradient over a thirty minute period. Fractions containing desired product were combined and concentrated in vacuo to a solid. The solid was treated with chloroform (100 ml), hydrogen chloride gas was passed through the solution which was then concentrated in vacuo to a yellow foam. The foam was triturated in diisopropyl ether (100 ml) then filtered. Insolubles were treated with toluene (100 ml), heated until boiling, filtered hot, and washed with toluene (50 ml).

These insolubles were crystallized from methylene chloride. Crystals were treated with chloroform (60 ml), and then with hydrogen chloride gas and concentrated in vacuo to a foam. Material was triturated in toluene (100 ml) and filtered and the insolubles were collected by filtration to afford 1.38 g of product.

Mass Spectrum (ion spray): m/z 444 (M-HCl).

$^1$H NMR (DMSOd$_6$): δ 9.71 (s, 1H), 8.56 (d, 1H), 8.44 (d, 1H), 8.28 (d, 1H), 7.99 (s, 1H), 7.84 (d, 1H), 7.73 (s, 2H), 7.64 (dd, 1H), 7.56 (bs, 1H), 4.56 (t, 2H), 3.13 (t, 2H), 1.41 (s, 18H).

Elemental analysis for C$_{28}$H$_{33}$ClN$_2$O$_3$0$\cdot$1.0 H$_2$O: Calculated: C, 67.38; H, 7.07; N, 5.61. Found: C, 67.60; H, 6.87; N, 5.35.

EXAMPLE 35

2-(3,5-di-t-butyl-4-hydroxyphenyl)-4-(2-(5-N-ethyl-N-methylaminomethylpyrid-2-yl-oxy)ethyl)oxazole dihydrochloride A. Preparation of 2-(3,5-di-t-butyl-4-hydroxyphenyl)-4-(2-(5-formylpyrid-2-yl-oxy)ethyl)oxazole The title compound was prepared substantially as described in Example 4 except using 2-pyridone-5-carboxaldehyde. After stirring at 22° C. for approximately 15.5 hours, the reaction was treated with water (2.1 eq., 870 51), stirred 10 minutes then concentrated in vacuo to afford a foam. The foam chromatographed, eluting with a gradient of 50 to 65% ethyl acetate:hexane over a thirty minute period. Fractions containing title compound were combined and concentrated in vacuo to afford a purple solid. The solid was treated with diethyl ether, triturated, stirred approximately 4 hours then filtered. The filtrate was concentrated in vacuo to afford a purple foam. The foam was chromatographed, eluting with a gradient of 20 to 35% acetone:hexane over a thirty minute period. Fractions containing the title compound were combined and concentrated in vacuo to afford 2.28 g of the subtitled compound as a foam. This material was taken on to the next step without further purification.

Mass Spectrum (FDMS): m/z 422. (M).

1H NMR (CDCl3): δ 9.43 (s, 1H), 7.82 (s, 2H), 7.78 (m, 2H), 7.34 (s, 1H), 6.59(d, J=10.3 Hz, 1H), 5.54 (s, 1H), 4.39 (t, J=6.4 Hz, 2H), 3.07 (t, J=6.4 Hz, 2H),1.49 (s, 18H).

B. Preparation of 2-(3,5-di-t-butyl-4-hydroxyphenyl)-4-(2-(5-N-ethyl-N-methylaminomethyl-pyrid-2-yl-oxy)ethyl) oxazole dihydrochloride Title compound was prepared from the compound of Step A substantially in accordance with the procedure in Example 11. The material was chromatographed, eluting with a gradient of 0 to 5% (1% ammonium hydroxide:methanol):chloroform over a thirty minute period. Remaining fractions were eluted with 5% (1% ammonium hydroxide:methanol):chloroform. Fractions containing the title compound were combined and concentrated in vacuo to afford an oil. The oil was treated with chloroform then hydrogen chloride gas resulting in crystalline formation. Crystals were collected by filtration and washed with chloroform affording 1.44 g. Material was recrystallized from methanol:tetrahydrofuran to afford 1.25 g of the title compound.

mp (c): 237–239

Mass Spectrum (FDMS): m/z 465. (M-2HCl).

1H NMR (DMSOd6): δ 10.73 (bs, 1H), 7.88 (s, 1H), 7.78 (d, J=2.3 Hz, 1H), 7.64(dd, J=2.3, 9.4 Hz, 1H), 6.45 (d, J=9.4 Hz, 1H), 4.12 (t, J=6.9 Hz, 2H), 3.97 (m,4H), 2.76–3.02 (m, 4H), 2.50 (s, 3H), 1.41 (s, 18H), 1.16 (t, J=7.2 Hz, 3H).

Elemental analysis for C28H41Cl2N3O3: Calculated: C, 62.45; H, 7.67; N, 7.80. Found: C,62.46; H, 7.71; N, 7.79.

EXAMPLE 36

2-(3,5-di-t-butyl-4-hydroxyphenyl)-4-(2-(4-N-methyl-N-ethylaminomethylphenylthio)ethyl) oxazole hydrochloride monohydrate A. Preparation of 2-(3,5-di-t-butyl-4-hydroxyphenyl)-4-(2-(4-formylphenylthio)ethyl)oxazole Subtitled compound was prepared by dissolving 3.84 g (14.6 mmole) triphenylphosphine, in 45 ml of tetrahydrofuran, chilling to −9° C. then adding under nitrogen, 2.3 ml (14.6 mmole) diethylazodicarboxylate. The reaction exothermed to −1° C. and was chilled again to −6° C. 4.64 g (14.6 mmole) of the compound of Example 1C was added. The deep red solution was stirred 15 minutes when 2.22 g (16.1 mmole) 4-mercaptobenzaldehyde (Tet.Lett.25, (17), 1753–1756, 1984) was added and the reaction was allowed to stir for 18 hours. The reaction was stripped and chromatographed eluting with 10% to 50% ethyl acetate/hexane gradient over 30 minutes. The appropriate fractions were bulked and stripped to give 3.48 g (54%) product which was used without further purification.

NMR (CDCl$_3$), δ 1.46 (t, 3H, J=9 Hz), 1.50 (s, 18H), 2.64 (d, 2H, J=5 Hz), 2.88–2.97 (m, 1H), 3.17 (t, 2H, J=9 Hz), 3.51 (t, 2H, J=9 Hz), 3.97–32 (m, 2H), 6.05 (s, 1H), 7.46 (d, 2H, J=9 Hz), 7.56 (d, 2H, J=9 Hz), 7.65 (s, 1H), 8.21 (s, 2H)

B. Preparation of 2-(3,5-di-t-butyl-4-hydroxyphenyl)-4-(2-(4-N-methyl-N-ethylaminomethylphenylthio)ethyl)oxazole hydrochloride monohydrate Methylethylamine 1.72 ml (20 mmole) and 5.92 ml (20 mmole) of titanium tetraisopropoxide were dissolved in 45 ml of punctilious ethanol, with stirring, under nitrogen and stirred 1 hour. Compound of Step A (4.38 g, 10 mmole), was added and the reaction was stirred for 3.5 hours. Sodium borohydride (570 mg, 15 mmole) was added and the reaction was stirred an additional 18 hours. Ammonia (16.3 ml, 2N) was added to give a thick suspension followed by 104 ml of methylene chloride. Diatomaceous earth (13 g) was added and the mixture was stirred and filtered through diatomaceous earth. The filtrate was washed one time with brine and dried, stripped and chromatographed, eluting with methylene chloride/methanol/concentrated ammonia 90:5:0.5. The tractions were combined, stripped of solvent, and dissolved in methylene chloride/isopropyl ether. Hydrogen chloride gas was bubbled in and the solution was concentrated and triturated with isopropyl ether to give 2.86 g (55%) of title product as a white foam.

FDMS-M$^+$ 480;

Elemental analysis for $C_{29}H_{40}N_2O_2S.HCl.H_2O$ Calculated: C, 64.86; H, 8.11; N, 5.21 Found: C, 64.56; H, 8.37; N, 4.93

NMR (CDCl$_3$), δ 1.46 (t, 3H, J=9 Hz), 1.50 (S, 18H), 2.64 (d, 2H, J=5 Hz), 2.88–2.97 (m, 1H), 3.17 (t, 2H, J=9 Hz), 3.51 (t, 2H, J=9 Hz), 3.97–32 (m, 2H), 6.05 (s, 1H), 7.46 (d, 2H, J=9 Hz), 7.56 (d, 2H, J=9 Hz), 7.65 (s, 1H), 8.21 (s, 2H)

EXAMPLE 37

2-(3,5-di-t-butyl-4-hydroxyphenyl)-4-(2-(4-N-methyl-N-ethylaminomethylphenoxy)ethyl)-5-methyloxazole hydrochloride monohydrate A. Preparation of ethyl 4-chloro-3-oxopentanoate Potassium ethyl malonate, 34 g (200 mmole) (Organic Synthesis Coll. Vol. IV, p. 417), 23.75 g (250 mmole) magnesium chloride, and 44.5 ml (320 mmole) triethylamine were suspended in 1.0 L acetonitrile, with stirring, under nitrogen. 2-Chloro-propionyl chloride, 9.7 ml (100 mmole), was added and the mixture was stirred under nitrogen for 18 hours. 100 ml of 5N hydrochloric acid, was added and the reaction was stirred for 2 hours. Layers were separated and organics stripped to give 21.09 g of crude product which was filtered through 300 ml silica, eluting with 20% ethyl acetate/hexane to give 10.37 g (58%) product.

NMR (CDCl3), δ 1.27 (t, 3H, J=4 Hz), 1.62 (d, 3H, J=4 Hz), 3.72 (dd, 2H, J=42 Hz), 4.52 (q, 2H, J=4 Hz)

B. Preparation of 2-(3,5-di-t-butyl-4-hydroxyphenyl)-4-carbethoxymethyl-5-methyloxazole Compound of example 1A, 6.6 g (26.5 mmole) and 10.3 g (57.7 mmole) of the compound of Step A were stirred together neat, at 140° C., under nitrogen, for a total of 6.5 hours. The reaction was cooled and chromatographed on 300 ml silica, eluting with 20%, then 50% ethyl acetate/hexane to give 4.48 g (45%) product.

FDMS-M+=373

NMR (CDCl3), δ 1.27 (t, 3H, J=4 Hz), 1.47 (s, 18H), 2.34 (s, 3H), 3.54 (s, 2H), 4.18 (q, 2H, J=4 Hz), 5.46 (s, 1H), 7.78 (s, 2H)

C. Preparation of 2-(3,5-di-t-butyl-4-hydroxyphenyl)-4-(2-hydroxyethyl)-5-methyloxazole Starting ester, the compound of Step B 4.43 g (11.88 mmole), was dissolved in 83 ml tetrahydrofuran with stirring, under nitrogen. Solid lithium aluminum hydride (LAH), 450 mg (11.88 mmole), was cautiously added. There was much bubbling. The mixture was stirred 30 minutes and another 225 mg (5.94 mmole) lithium aluminum hydride was added and the reaction stirred under nitrogen overnight. Water (0.675 ml) was cautiously added followed by 0.675 ml 15% sodium hydroxide, followed by 2.0 ml water. The inorganics were filtered off and the filtrate was stripped, dissolved in ethyl acetate, washed once with 1 N hydrochloric acid, twice with brine, and stripped to give 3.61 g (92%) of product which was used without further purification.

FDMS-M+=331

NMR (CDCl3), δ 1.48 (s, 18H), 2.32 (s, 3H), 2.73 (t, 2H, J=4 Hz), 3.91 (t, 2H, J=4 Hz), 5.51 (s, 1H), 7.81 (s, 2H)

D. Preparation of 2-(3,5-di-t-butyl-4-hydroxyphenyl)-4-(2-(4-formylphenoxy)ethyl)-5-methyloxazole The compound of Step C 3.61 g (10.9 mmole), 1.53 g (12.5 mmole) 4-hydroxybenzaldehyde, and 3.29 g (12.5 mmole) triphenylphosphine were dissolved in 30 ml tetrahydrofuran with stirring, under nitrogen. The solution was chilled to −5° C. and a solution of 1.97 ml (12.5 mmole) diethyldiazodicarboxylate in 10 ml. tetrahydrofuran was added over 10 minutes, with stirring. The reaction exothermed to +3° C. The bath was removed and the reaction stirred under nitrogen for 3 days. The reaction was stripped, dissolved in methylene chloride and placed in the freezer. The diethoxycarbonylhydrazine was then filtered off and the filtrate was chromatographed on 400 ml silica, eluting with a 5% isopropyl alcohol/hexane. The appropriate fractions were bulked and stripped to give 3.52 g (74%) product which was used without further purification.

FDMS-M+=435.

NMR (CDCl3), δ 1.48 (s, 18H), 2.37 (s, 3H), 3.01 (t, 2H, J=4 Hz), 4.34 (t, 2H, J=4 Hz), 5.48(s, 1H), 7.00 (d, 2H, J=7 Hz), 7.80 (s, 2H), 7.82 (d, 2H, J=7 Hz), 9.87 (s, 1H)

E. Preparation of 2-(3,5-di-t-butyl-4-hydroxyphenyl)-4-(2-(4-methylethylaminomethylphenoxy)ethyl)-5-methyloxazole hydrochloride hydrate Methylethylamine, 0.71 ml (8.32 mmole) and 2.46 ml (8.32 mmole) Ti(OPr)4 were dissolved in 17 ml of ethanol and stirred for 10 minutes under nitrogen. Compound of step D, 1.75 g (4.16 mmole), was added and the mixture was stirred for 4 hours. Sodium borohydride, 240 mg (6.23 mmole) was added and the reaction was stirred for 3 days. Ammonia, 5.8 ml 2N, was added to give a thick suspension. Methylene chloride (40 ml) was added then 5.3 g diatomaceous earth and the mixture was stirred, and filtered through diatomaceous earth. The filtrate was washed 2 times with brine then dried. The organics were stripped and chromatographed, eluting with methylene chloride/methanol/concentrated ammonia 90:10:1. Fractions were bulked, stripped, dissolved in methylene chloride/isopropyl ether. Hydrogen chloride gas was bubbled in. Product was evaporate to dryness to give 1.36 g (63%) of a white foam.

FDMS-M+ 478;

Elemental Analysis for $C_3OH_{42}N_2O_3 \cdot HCl \cdot H_2O$ Calculated: C, 67.58; H, 8.51; N, 5.25 Found: C, 67.21; H, 8.61; N, 5.06

NMR (CDCl3), δ 1.44 (t, 3H, J=4 Hz), 1.49 (m, 18H), 2.51 (s, 3H), 2.60 (d, 2H, J=4 Hz), 2.88–3.23 (m, 4H), 3.99–4.14 (m, 2H), 4.43 (t, 2H, J=6 Hz), 5.99 (s, 1H), 6.92 (d, 2H, J=7 Hz), 7.49 (d, 2H, J=7 Hz), 8.16 (s, 2H)

EXAMPLE 38

2-(3,5-di-t-butyl-4-hydroxyphenyl)-4-(2-(4-N-methyl-N-ethylaminomethylphenoxy)ethyl)thiazole hydrochloride hydrate A. Preparation of N-methyl-(3,5-di-t-butyl-4-hydroxy)benzamide (3,5-di-t-butyl-4-hydroxy)benzoic acid, 75 g (300 mmole) and 53.46 g (330 mmole) carbonyldiimidazole were refluxed in 900 ml tetrahydrofuran, with stirring, under nitrogen, for 2 hours. The reaction was cooled and 300 ml 40% aqueous methylamine was added and stirred under nitrogen at room temperature for 18 hours. The mixture was stripped to a wet solid and 500 ml of water was added. The mixture was stirred, and filtered to give 88.5 g (100%) product, which contained approximately 30 mole % imidazole. The product was used without further purification.

NMR (CDCl3), δ 1.44 (s, 18H), 2.98 (d, 3H, J=4 Hz), 6.2 (bs, 1H), 7.58 (s, 2H)

B. Preparation of N-methyl-(3,5-di-t-butyl-4-hydroxy)thiobenzamide

The compound of Step A 88.5 g (ca. 300 mmole), and 60.6 g (150 mmole) Lawesson's reagent was dissolved in 300 g hexamethylphosporamide at 100° C. and stirred under nitrogen at 100° C. for 1 hour. The mixture was cooled, water was added, and the mixture was extracted twice with diethyl ether. The combined organic layers were washed three times with water, and the organic layer was stripped to give 91.3 g of crude product which was triturated with 250 ml methylene chloride to give 43.7 g product. Hexane, 350 ml, was added to the filtrate with stirring to give a second crop of 26.7 g product. The filtrate was boiled down to 400 ml to give a third crop of 7.2 g product. The total yield was 77.6 g (93%)

NMR (CDCl3), δ 1.44 (s, 18H), 3.33 (d, 3H, J=4 Hz), 5.52 (bs, 1H), 7.60 (s, 2H)

C. Preparation of 3,5-di-t-butyl-4-hydroxythiobenzoic acid, (3-ethoxycarbonyl-2-oxo-1-propionyl)ester The compound of Step B 42.0 g (150 mmole), 27 ml (200 mmole) ethyl 3-chloroacetoacetate and 24.9 g (150 mmole) potassium iodide was stirred in 1.0 l tetrahydrofuran, under nitrogen, and refluxed for 4.5 hours. The reaction was cooled and 75 ml water was added and the mixture stirred for 18 hours. The organics were stripped, and the crude product was dissolved in chloroform, washed once with water, and once with brine, then chromatographed, eluting with a gradient of methylene chloride to methylene chloride/methanol/concentrated ammonia, 90:10:1 over 10 minutes. The partially purified product was then chromatographed on 600 ml silica, eluting with 10% ethyl acetate/hexane to give 28 g (44%) product.

FDMS-M+=394

NMR (CDCl3), δ 1.25 (t, 3H, J=4 Hz), 1.45 (s, 18H), 3.66 (s, 2H), 3.98 (s, 2H), 4.18 (q, 2H, J=4 Hz), 5.80 (s, 1H), 7.83 (s, 2H)

D. Preparation of 2-(3,5-di-t-butyl-4-hydroxyphenyl)-4-carbethoxymethylthiazole

The compound of Step C 25.1 g (63.7 mmole), and 19.6 g (255 mmole)of ammonium acetate was refluxed in 320 ml glacial acetic acid, with stirring, under nitrogen, for 3.25 hours. The reaction was cooled and ethyl acetate and water were added. Layers were separated and the aqueous layer was washed once with ethyl acetate. The combined organic layers were washed once with water and 8 times with saturated sodium bicarbonate solution to achieve a final wash of pH 9. The organic layer was stripped and the crude product chromatographed on 600 ml silica, eluting with 10% ethyl acetate/hexane to give 14.96 g (57%) product.

FDMS-M+=375.

NMR (CDCl3), δ 1.29 (t, 3H, J=4 Hz), 1.48 (s, 18H), 3.87 (s, 2H), 4.21 (q, 2H, J=4 Hz), 5.45 (s, 1H), 7.09 (s, 1H), 7.72 (s, 2H)

E. Preparation of 2-(3,5-di-t-butyl-4-hydroxyphenyl)-4-(2-hydroxyethyl)thiazole

The compound of Step D 5.0 g (13.33 mmole), was dissolved in 95 ml tetrahydrofuran with stirring, under nitrogen. Solid lithium aluminum hydride, 760 mg (20 mmole), was cautiously added. There was much bubbling. The mixture was stirred under nitrogen for 1 hour. Water, 0.76 ml H$_2$O, was cautiously added followed by 0.76 ml 15% sodium hydroxide, followed by 2.3 ml water. The inorganics were filtered off and the filtrate was stripped, dissolved in ethyl acetate, washed once with 1 N hydrochloric acid, twice with brine, and stripped to give 4.42 g (99%) product which was used without further purification.

FDMS-M+=333

NMR (CDCl$_3$), δ 1.48 (s, 18H), 3.02 (t, 2H, J=4 Hz), 3.98 (t, 2H, J=4 Hz), 5.50 (s, 1H), 6.87 (s, 1H), 7.73 (s, 2H)

F. Preparation of 2-(3,5-di-t-butyl-4-hydroxyphenyl)-4-(2-(4-formylphenoxy)ethyl)thiazole The compound of Step E 4.20 g (12.6 mmole), 1.76 g (14.44 mmole) 4-hydroxybenzaldehyde, and 3.79 g (14.44 mmole) triphenyl phosphine were dissolved in 37 ml tetrahydrofuran with stirring, under nitrogen. The solution was chilled to −10° C. and a solution of 2.27 ml (14.44 mmole) diethylazodicarboxylate in 12.5 ml. tetrahydrofuran was added over 10 minutes, with stirring. The reaction exothermed to −1° C. The bath was removed and the reaction stirred under nitrogen overnight. The reaction was stripped, dissolved in methylene chloride and placed in the freezer. The diethoxycarbonylhydrazine was then filtered off and the filtrate was chromatographed on 400 ml silica, eluting with a 15 then 20% ethyl acetate/hexane. The appropriate fractions were bulked and stripped to give 3.98 g (72%) product which was used without further purification.

NMR (CDCl3), δ 1.48 (s, 18H), 3.31 (t, 2H, J=4 Hz), 4.45 (t, 2H, J=4 Hz), 5.47 (s, 1H), 6.96 (s, 1H), 7.03 (d, 2H, J=7 Hz), 7.73 (s, 2H), 7.83 (d, 2H, J=7 Hz), 9.88 (s, 1H)

G. Preparation of 2-(3,5-di-t-butyl-4-hydroxyphenyl)-4-(2-(4-N-methyl-N-ethylaminomethylphenoxy)ethyl)thiazole hydrochloride hydrate N-methyl-N-ethylamine, 0.96 ml (11.26 mmole), and 3.33 ml (11.26 mmole) Ti(OPr)4 was dissolved in 20 ml of ethanol with stirring under nitrogen. The mixture was stirred for 10 minutes. The compound of Step F, 2.46 g (5.63 mmole) was added and the mixture was stirred for 2.5 hours. Sodium borohydride, 320 mg (8.44 mmole), was added and the reaction was stirred for 3.5 days. Ammonia, 7.85 ml 2N, was added to give a thick suspension then 55 ml of methylene chloride was added. Diatomaceous earth, 7.2 g, was added and the mixture was stirred and filtered through diatomaceous earth. The filtrate was washed twice with brine then dried and the organics were stripped and chromatographed, eluting with methylene chloride/methanol/concentrated ammonia 90:10:1. Fractions were combined, stripped and dissolved in methylene chloride/isopropyl ether. Hydrogen chloride gas was bubbled in and the product was concentrated and triturated with isopropyl ether to give 1.54 g (54%) white foam.

FDMS-M+ 480;

Elemental Analysis for C29H40N2O2S.HCl.1.75 H2O Calculated: C, 63.48; H, 8.17; N, 5.11; Found: C, 63.55; H, 7.89; N, 4.86

NMR (CDCl3), δ 1.46 (t, 3H, J=4 Hz), 1.49 (m, 18H), 2.62 (d, 2H, J=4 Hz), 2.89 (m, 1H, J=4 Hz), 3.15 (m, 1H), 3.50 (bs, 2H), 4.10 (m, 2H), 4.41 (t, 2H, J=4 Hz), 5.75 (s, 1H), 6.96 (d, 2H, J=7 Hz), 7.12 (s, 1H), 7.50 (d, 2H, J=7 Hz), 7.90 (s, 2H)

EXAMPLE 39

E-2-(3,5-di-t-butyl-4-hydroxyphenyl)-4-(3-(4-N-methyl-N-ethylaminomethylphenyl)-2-propenyl) oxazole hydrochloride hydrate A. Preparation of 4-(2-bromoethyl)-2-(3,5-di-t-butyl-4-hydroxyphenyl)oxazole To a stirred solution of triphenylphosphine (31.0 g, 118 mmole) in methylene chloride (394 ml) was added bromine (6.09 ml, 118 mmole). A small amount of additional triphenylphosphine was added to clear the solution. To this was added a mixture of the compound of Example 1C (25.0 g, 78.9 mmole) and imidazole (10.7 g, 158 mmole) dissolved in methylene chloride (315 ml) over 15 minutes. The reaction was allowed to stir at room temperature for 1 hour and was filtered. The filtrate was evaporated to dryness, triturated with methylene chloride/toluene, and filtered. This filtrate was chromatographed on silica gel using a hexane-ethyl acetate gradient to give the subtitled product (25.4 g, 85%):

1H NMR (CDCl3) δ 7.85 (s, 2H), 7.5 (s, 1H), 5.5 (s, 1H), 3.65 (t, J=6 Hz, 2H), 3.15 (t, J=6 Hz, 2H), 1.5 (s, 18H);

FDMS 381 (M+).

B. Preparation of 2-(3,5-di-t-butyl-4-hydroxyphenyl)-4-(2-triphenylphosphonium ethyl)oxazole bromide To a stirred solution of 4-(2-bromoethyl)-2-(3,5-di-t-butyl-4-hydroxyphenyl)oxazole (25.4 g, 66.8 mmole) in xylenes (135 ml) was added triphenylphosphine (17.5 g, 66.8 mmole). The reaction was heated to reflux for 22 hours, and the xylene decanted from the precipitated product. The product was triturated in diethyl ether, filtered, and then triturated with ethyl acetate and filtered to give the intermediate phosphonium salt 2-(3,5-di-t-butyl-4-hydroxyphenyl)-4-(2-triphenylphosphonium ethyl)oxazole bromide (30.7 g, 72%):

1H NMR (CDCl3) δ 8.2 (bs, 1H), 7.8 (m, 17H), 5.5 (bs, 1H), 4.2 (bs, 2H), 3.1 (bs, 2H), 1.5 (s, 18H); FDMS 562 (M-Br+).

C. Preparation of E-2-(3,5-di-t-butyl-4-hydroxyphenyl)-4-(3-(4-formylphenyl)-2-propenyl)oxazole diethyl acetal To a stirred solution of 2-(3,5-di-t-butyl-4-hydroxyphenyl)-4-(2-triphenylphosphonium ethyl)oxazole bromide (28.1 g, 43.8 mmole) in tetrahydrofuran (220 ml) was added terepthaldehyde mono-diethylacetal (8.68 ml, 43.8 mmole). This mixture was cooled to −10° C. and a 1M solution of sodium hexamethyldisilazane in tetrahydrofuran (87.5 ml, 87.5 mmole) was added dropwise over 8 minutes maintaining a temperature of less than 4° C. The reaction was stirred at 0° C. for 3 hours, quenched with water, and diluted with ethyl acetate and water. The pH was adjusted to 8.5 with 1N hydrochloric acid. The organic layer was extracted with brine, dried over sodium sulfate, evaporated to dryness, and chromatographed on silica gel using a hexane/acetone gradient to give the trans isomer of the olefin intermediate E-2-(3,5-di-t-butyl-4-hydroxyphenyl)-4-(3-(4-formylphenyl)-2-propenyl)oxazole diethyl acetal (2.6 g, 12%):

1H NMR (CDCl3) 7.85 (s, 2H), 7.4 (m, 5H), 6.55 (d, J=16 Hz, 1H), 6.4 (dt, J=16 Hz, 7 Hz, 1H), 5.5 (s, 1H), 5.45 (s, 1H), 3.5–3.6 (m, 6H), 1.5 (s, 18H), 1.25 (t, J=6 Hz, 6H);

FDMS 491 (M+).

D. Preparation of Z-2-(3,5-di-t-butyl-4-hydroxyphenyl)-4-(3-(4-formylphenyl)-2-propenyl)oxazole diethyl acetal Impure fractions from the above chromatography were rechromatographed on silica gel using a hexane-diethylether gradient to give the subtitled product (1.6 g, 7%):

1H NMR (CDCl$_3$) 7.85 (s, 2H), 7.45 (d, J=8 Hz, 2H), 7.4 (s, 1H), 7.3 (d, J=8 Hz, 2H), 6.35 (d, J=11 Hz, 1H), 5.95 (dt, J=11 Hz, 7 Hz, 1H), 5.5 (s, 2H), 3.5–3.7 (m, 6H), 1.5 (s, 18H), 1.25 (t, J=6 Hz, 6H).

E. Preparation of E-2-(3,5-di-t-butyl-4-hydroxyphenyl)-4-(3-(4-formylphenyl)-2-propenyl)oxazole To a stirred solution of the E-2-(3,5-di-t-butyl-4-hydroxyphenyl)-4-(3-(4-formylphenyl)-2-propenyl)oxazole diethyl acetal (2.53 g, 5.14 mmole) in diethyl ether (51 ml) was added 1N hydrochloric acid (51 ml), then concentrated hydrochloric acid (5.1 ml). The reaction was allowed to stir 18 hours, then basidified with saturated sodium bicarbonate. The organic layer was extracted with brine, dried over sodium sulfate, evaporated to dryness, and chromatographed on silica gel using a hexane-ethyl acetate gradient to give the desired product (1.19 g, 55%):

1H NMR (CDCl3) 9.95 (s, 1H), 7.9 (s, 2H), 7.85 (d, J=8 Hz, 2H), 7.5 (d, J=8 Hz, 2H), 7.45 (s, 1H), 6.6 (m, 2H), 5.5 (s, 1H), 3.6 (d, J=5 Hz, 2H), 1.5 (s, 18H);

FDMS 417 (M+).

F. Preparation of E-2-(3,5-di-t-butyl-4-hydroxyphenyl)-4-(3-(4-N-methyl-N-ethylaminomethyl-phenyl)-2-propenyl)oxazole hydrochloride To a stirred solution of ethylmethylamine hydrochloride (0.54 g, 5.7 mmole) in ethanol (5.8 ml) was added triethylamine (0.79 ml, 5.7 mmole), titanium tetraisopropoxide (1.68 ml, 5.7 mmole), and finally the E-2-(3,5-di-t-butyl-4-hydroxyphenyl)-4-(3-(4-formylphenyl)-2-propenyl)oxazole (1.19 g, 2.85 mmole) in ethanol (7.1 ml). The reaction was stirred for 4.5 hours, then sodium borohydride (0.16 g, 4.28 mmole) was added. After 20 hours at room temperature, the reaction was poured into 20 ml 2N ammonium hydroxide and diluted with methylene chloride. The mixture was filtered though diatomaceous earth and the filtrate was extracted with brine. The organic layer was dried over sodium sulfate, evaporated to dryness, and chromatographed on silica gel using a methylene chloride-methanol gradient to give the free base (0.79 g, 60%). The free base (0.79 g, 1.71 mmole) was dissolved in methylene chloride (17 ml), treated with hydrogen chloride gas, and evaporated to give desired product (0.83 g, 98%):

1H NMR (CDCl3) δ 7.9 (s, 2H), 7.55 (d, J=9 Hz, 2H), 7.5 (d, J=9 Hz, 2H), 7.45 (s, 1H), 6.6 (d, J=16 Hz, 1H), 6.45 (dt, J=16 Hz, 7 Hz, 1H), 5.6 (s, 1H), 4.15 (m, 2H), 3.6 (d, J=7 Hz, 2H), 3.2 (m, 1H), 2.9 (m, 1H), 2.65 (d, J=5 Hz, 3H), 1.5 (m, 21H);

FDMS 460 (M+-HCl);

Elemental Analysis for C30H41ClN2O2.1.5H2O: Calculated: 68.75; H, 8.46; N, 5.34. Found: C, 69.06; H, 8.30; N, 5.49.

EXAMPLE 40

Z-2-(3,5-di-t-butyl-4-hydroxyphenyl)-4-(3-(4-N-methyl-N-ethylaminomethylphenyl)-2-propenyl) oxazole hydrochloride monohydrate A. Preparation of Z-2-(3,5-di-t-butyl-4-hydroxyphenyl)-4-(3-(4-formylphenyl)-2-propenyl) oxazole To a stirred solution of the compound of Example 39D (1.59 g, 3.23 mmole) in diethyl ether (32ml) was added 1N hydrochloric acid (32ml), then concentrated hydrochloric acid (3.2 ml). The reaction was allowed to stir 30 minutes, then basidified with saturated sodium bicarbonate. The organic layer was extracted with brine, dried over sodium sulfate, evaporated to dryness, and chromatographed on silica gel using a hexane-ethyl acetate gradient to give the desired subtitled product (1.15 g, 85%)

1H NMR (CDCl3) 10.0 (s, 1H), 7.9 (d, J=8 Hz, 2H), 7.85 (s, 2H), 7.5 (d, J=8 Hz, 2H), 7.45 (s, 1H), 6.65 (d, J=11 Hz, 1H), 6.1 (dt, J=11 Hz, 7 Hz, 1H), 5.5 (s, 1H), 3.65 (d, J=7 Hz, 2H), 1.5 (s, 18H);

FDMS 417 (M+).

B. Preparation of Z-2-(3,5-di-t-butyl-4-hydroxyphenyl)-4-(3-(4-N-methyl-N-ethylaminomethyl-phenyl)-2-propenyl)oxazole hydrochloride To a stirred solution of ethylmethylamine hydrochloride (0.78 g, 8.18 mmole) in ethanol (4.1 ml) was added triethylamine (1.14 ml, 8.18 mmole), titanium tetraisopropoxide (2.42 ml, 8.18 mmole), and finally the Z-2-(3,5-di-t-butyl-4-hydroxyphenyl)-4(3-(4-formylphenyl)-2-propenyl)oxazole (1.71 g, 4.09 mmole) in ethanol (10 ml). The reaction was stirred for 3.5 hours, then sodium borohydride (0.23 g, 6.14 mmole) was added. After 18 hours at room temperature, the reaction was poured into 30 ml 2N ammonium hydroxide and diluted with methylene chloride. The mixture was filtered though diatomaceous earth and the filtrate was extracted with brine. The organic layer was dried over sodium sulfate, evaporated to dryness, and chromatographed on silica gel using a methylene chloride-methanol gradient to give the free base (1.63 g, 86%). The free base (1.3 g, 2.82 mmole) was dissolved in methylene chloride (28 ml), treated with hydrogen chloride gas, and evaporated to give desired product (1.40 g, 100%):

1H NMR (CDCl3) δ 8.05 (s, 2H), 7.6 (d, J=9 Hz, 2H), 7.5 (s, 1H), 7.35 (d, J=9 Hz, 2H), 6.65 (d, J=11 Hz, 1H), 6.05 (dt, J=11 Hz, 7 Hz, 1H), 5.8 (s, 1H), 4.15 (m, 2H), 3.75 (d, J=7 Hz, 2H), 3.2 (m, 1H), 2.95 (m, 1H), 2.7 (d, J=5 Hz, 3H), 1.5 (m, 21H);

FDMS 460 (M+-HCl);

Elemental Analysis for C30H41ClN2O2.H$_2$O: Calculated: 69.95; H, 8.41; N, 5.44. Found: C, 70.08; H, 8.10; N, 5.61.

EXAMPLE 41

2-(3,5-di-t-butyl-4-hydroxyphenyl)-4-(3-(4-N-methyl-N-ethylaminomethylphenyl)propyl)oxazole hydrochloride hydrate To a stirred solution of Z-2-(3,5-di-t-butyl-4-hydroxyphenyl)-4-(3-(4-N-methyl-N-ethylaminomethylphenyl)-2-propenyl)oxazole (1.2 g, 2.6 mmole) in toluene (26 ml) was added 5% palladium on carbon (0.12 g). The suspension was subjected to 1 atmosphere hydrogen for 5 hours and filtered. The filtrate was evaporated to dryness and chromatographed on silica gel using a methylene chloride-methanol gradient to give the saturated free base (0.99 g, 82%). The free base (1.05 g, 2.27 mmole) was dissolved in methylene chloride (23 ml), treated with hydrogen chloride gas, evaporated, and triturated with diisopropyl ether to give desired product (1.00 g, 88%):

1H NMR (CDCl$_3$) δ 7.9 (s, 2H), 7.5 (d, J=9 Hz, 2H), 7.4 (s, 1H), 7.3 (d, J=9 Hz, 2H), 6.65 (d, J=11 Hz, 1H), 5.6 (s, 1H), 4.1 (m, 2H), 3.1 (m, 1H), 2.9 (m, 1H), 2.7 (t, J=7 Hz, 2H), 2.65 (m, 5H), 2.05 (m, 2H), 1.5 (m, 21H);

FDMS 462 (M+-HCl);

Elemental Analysis for C30H43ClN2O2.1.5H2O: Calculated: 68.48; H, 8.81; N, 5.32. Found: C, 68.40; H, 8.63; N, 5.22.

EXAMPLE 42

2-(3,5-di-tert-butyl-4-hydroxyphenyl))-4-((4-N-methylethylamino methyl)phenoxymethyl)oxazole hydrochloride A. N-carbo(3,5-di-t-butyl-4-hydroxy)phenyl-DL-serine methyl ester To a suspension of benzoic acid in tetrahydrofuran (165 ml) was added in portions over a 20 minute period, 1,1'-carbonyldiimidazole. The resulting gold solution was stirred at 22° C. for twenty minutes then added dropwise to the solution described below.

To a suspension of DL-serine methyl ester in tetrahydrofuran (115 ml) was added diisopropyl ethyl amine followed by dimethyl formamide (70 ml). The resulting colorless solution was stirred at 22° C. for one hour then the activated benzoic acid derivative (described above) was added. The reaction was stirred at 22° C. for 5 days then concentrated in vacuo to an oil. The oil was treated with ethyl acetate (250 ml) and washed with three times with 1:1 brine:0.1N hydrochloric acid, and one time with brine. The organics were dried over sodium chloride, warmed on a steam bath, filtered hot, and the filtrate was concentrated in vacuo to an oil. The oil was then treated with 1:1 hexane:ethyl acetate, reduced in volume on a steam bath to approximately 250 ml then sonicated. The mixture was cooled to −20° C. for approximately 2 hours resulting in crystal formation. Crystals were collected by filtration, washed with 70% hexane:ethyl acetate to afford 49.13 g of the title compound. The filtrate was concentrated in vacuo to an oil. The oil was treated with 1:1 hexane:ethyl acetate then subjected to prepatory chromatography eluting with 50 to 70% hexane:ethyl acetate over a thirty-minute period. Desired fractions containing title compound were combined and concentrated in vacuo to an oil. The title compound was recrystallized from diethyl ether:hexane to afford 11.32 g of the title compound. A total of 60.45 g (56%) of the title compound was isolated.

mp (°C.): 108–109

Mass Spectrum (FDMS): m/z 351 (M).

1H NMR (CdCL3): δ 7.65 (s, 2H), 6.99 (d, J=6.2 Hz, 1H), 5.60 (s, 1H), 4.85 (dt, J=3.6 Hz, 1H), 4.06 (bs, 2H), 3.83 (s, 3H), 1.45 (s, 18H).

Elemental Analysis for C19H29NO5: Calculated: C, 64.94; H, 8.32; N, 3.99. Found: C, 65.20; H, 8.42; N, 4.22.

B. 4-((RS)carbomethoxy)-2-(3,5-di-tert-butyl-4-hydroxyphenyl))-2-oxazoline

To a suspension of N-carbo(3,5-di-t-butyl-4-hydroxy) phenyl-DL-serine methyl ester (0.17 mole, 58.81 g) and imidazole (0.18 mole, 12.53 g) in acetonitrite (890 ml) at 22° C. was added triphenylphosphine (0.18 mole, 48.28 g) followed by carbon tetrabromide (0.18 mole, 61.05 g). After stirring 2.5 hours, the reaction was concentrated in vacuo to a foam that contains crystalline material. The mixture was treated with ethyl acetate:hexane (100 ml), then cooled to −20° C. The insolubles were collected by filtration and discarded. The filtrate was subjected to preparatory chromatography, eluting with a gradient of 25 to 40% ethyl acetate:hexane over a 30-minute period. Fractions containing the title compound plus a coeluting impurity were resubjected to prepatory chromatography, eluting with 15 to 35% ethyl acetate:hexane over 30 minutes. Fractions containing the title compound were combined, concentrated in vacua to afford 55.75 g (99%) of an oil that slowly crystallizes.

mp (°C.): 102–104

Mas Spectrum (FDMS): m/z 333 (M)

$^1$H NMR (CDCl$_3$): δ 7.80 (S, 2H), 5.59 (S, 1H), 4.91 (dd, J=7.6, 10.4 Hz, 1H), 4.73 (dd, J=7.6, 8.6 Hz, 1H), 4.53 (dd, J=8.6, 10.4 Hz, 1H), 3.80 (s, 3H), 1.45 (s, 18H)

Elemental analysis for C$_{19}$H$_{27}$NO$_4$: Calculated: C, 68.44; H, 8.16; N, 4.20 Found: C, 68.33; H, 8.10; N, 4.34

C. 4-(carbomethoxy)-2-(3,5-di-tert-butyl-4-hydroxyphenyl) oxazole

A solution of ((RS)-4-carbomethyox)-2-(3,5-di-tert-butyl-4-hydroxypenyl))-2-oxazoline (0.66 mole, 220.15 g) in acetone (1.6 L) was treated with activated manganese oxide (6.60 mole, 574.0 g). The suspension was stirred at 22° C. for 17.5 hours then heated at 45° C. for one hour. Diatomaceous earth (250 ml) was added to the reaction, then the suspension was filtered through a pad of silica (2.5 cm×14.5 cm) and diatomaceous earth (250 g). The insolubles were rinsed with acetone until no product was observed in the filtrate by thin layer chromatography. The filtrate was concentrated in vacuo to afford 303.5 g of a black solid. The material was treated with diethyl ether (500 ml), and placed on a steam bath until the solid dissolved, then hexane was added (250 ml). The solution was boiled down until crystals formed. The mixture was cooled to 220° C., crystals were collected by filtration and washed with 2:1 hexane:diethyl ether to afford 98.1 g of the title compound that contains an impurity. This material was subjected to multi-recrystallizations as described above to afford 92.46 g of the title compound. Additional title compound was isolated by multiple recrystallizations of the filtrates to afford 36.94 g.

The filtrate from the crystallization was concentrated in vacuo to a solid then recrystallized as described above to afford 43.46 g of the title compound. The filtrate was concentrated in vacuo to a solid. The solid was treated with methylene chloride then divided into two lots. Each lot was subjected to preparatory chromatography eluting with 5 to 25% ethyl acetate:hexane over a 30-minute period. Fractions containing the title compound plus a coeluting impurity were combined and concentrated in vacuo to afford a black solid. This solid was recrystallized as described above to afford 20.74 g of a yellow/green solid. The solid was then triterated in boiling 1:4 ethyl acetate:hexane (200 ml), filtered hot and washed with 1:4 ethyl acetate:hexane to afford 17.99 g of the title compound. Additional title compound was recrystallized from the filtrate to afford 0.65 g. A total of 148.04 g (68%) of the title compound was isolated.

mp (°C.): 163

Mass Spectrum (FDMS): m/z 331 (M).

$^1$H NMR (CDCl$_3$): δ 8.23 (s, 1H), 7.91 (s, 2H), 5.59 (s, 1H), 3.94 (s, 3H), 1.48 (s, 18H).

Elemental Analysis for C$_{19}$H$_{25}$NO$_4$: Calculated: C, 68.86; H, 7.60; N, 4.23. Found: C, 69.11; H, 7.72; N, 4.21.

D. (4-(hydroxymethyl)-2-(3,5-di-tert-butyl-4-hydroxyphenyl))-2-oxazole

A dark blue solution of 4-(carbomethoxy)-2-(3,5-di-tert-butyl-4-hydroxyphenyl))-2-oxazole (0.39 mole, 127.71 g) in tetrahydrofuran (2.6 L) and a 3 neck 12 L flask was treated with methanol (0.58 mole, 23.4 ml). Next, lithium borohydride (0.58 mole, 12.59 g) was added carefully over a 60 minute period. During this addition, the reaction was cooled with an ice bath to maintain temperature between 19 and 24° C. Once the borohydride addition was complete, the orange colored reaction was slowly bought to reflux (ca. 50 minutes). After refluxing for 4.5 hours, the bright yellow colored reaction was cooled to 22° C. The reaction was then carefully treated with 5N hydrochloric acid (620 ml) over a thirty-minute period. vigorous gas evolution was observed during the addition of the first 40 ml of hydrochloric acid. Ethyl acetate (1 L) was added and the reaction was divided into two lots. Each lot was treated with water (500 ml) and the phases were separated. The aqueous phases were combined and extracted twice with ethyl acetate. The organic phases were combined and concentrated in vacuo to an oil. Diethyl ether (500 ml) was added to the oil, reduced in volume on a steam bath to approx. 500 ml, then cooled to −78° C. (using dry ice/acetone) for one hour. After warming to 22° C. the resulting crystals were collected by filtration and washed with diethyl ether to afford 56.55 g of the title compound. Subsequent recrystallizations of the filtrate afforded an additional 52.76 g. A total of 109.31 g (94%) of the title compound was isolated.

mp (°C.): 150

Mass Spectrum (FDMS): m/z 303 (M).

1H NMR (CdCL3): δ 8.33 (s, 2H), 7.68 (s, 1H), 6.12 (s, 1H), 4.80 (s, 2H), 1.51 (s, 18H).

Elemental Analysis for $C_{18}H_{25}NO_3$: Calculated: C, 71.26; H, 8.31; N, 4.62. Found: C, 71.52; H, 8.26; N, 4.79.

E. 4-(bromomethyl)-2-(3,5-di-tert-butyl-4-hydroxyphenyl) oxazole

A suspension of 4-(hydroxymethyl)-2-(3,5-di-tert-butyl-4-hydroxyphenyl) oxazole (44.2 mmole, 13.41 g) in acetonitrile (230 ml) was treated with triphenylphosphine (53.0 mmole, 13.91 g) followed by carbon tetrabromide (53.0 mmole, 17.59 g). The resulting solution was stirred at approximately 22° C. for 3 hours. Next, additional carbon tetrabromide (22.0 mmole, 13.13 g) and triphenylphosphine 22.0 mmole, 5.79 g) was added to the reaction. After stirring for an additional 40 minutes, the reaction was quenched with water (5 mL), stirred 10 minutes and concentrated in vacuo and stored at 5° C. for approximately 16 hours. The material was then taken up into chloroform and subjected to prepatory chromatography eluting with 35 to 50% chloroform-:hexane over a thirty-minute period. Fractions containing title compound were combined, dried over sodium sulfate, filtered, concentrated in vacuo to afford 9.7 g of the title compound that crystallized out upon standing at 22° C.

mp (°C.):

Mass Spectrum (FDMS): m/z 367 (M+1).

1H NMR (CdCL3): δ 7.84 (s, 2H), 7.65 (s, 1H), 5.53 (s, 1H), 4.44 (s, 2H), 1.48 (s, 18H).

Elemental Analysis for: C18H24BrNO2 Calculated: C, 59.02; H, 6.60; N, 3.82. Found: C, 58.83; H, 6.53; N, 3.85.

F. 4-(4-(2-formyl)phenoxy methyl)-2-(3,5-di-tert-butyl-4-hydroxyphenyl))oxazole

A suspension of 4-(bromomethyl)-2-(3,5-di-tert-butyl-4-hydroxyphenyl) oxazole (26.5 mmole, 9.70 g), 4-hydroxybenzaldehyde (29.1 mmole, 3.56 g), potassium carbonate (79.4 mmole, 10.97 g) and potassium iodide (26.5 mmole, 4.39 g) in methyl ethyl ketone (275 ml) was refluxed for 2 hours. The reaction was then cooled to approximately 22° C., filtered, concentrated in vacuo to an oil. The oil was treated with ethyl acetate (250 ml) then washed twice with saturated aqueous sodium bicarbonate, once with aqueous sodiumbisulfate and once with brine. The organic layer was dried over sodium sulfate, filtered, and concentrated in vacuo to an oil. The material was taken up into ethyl acetate, then subjected to prepatory chromatography eluting with 30 to 50 ethyl acetate:hexane over a thirty-minute period. Fractions containing title compound plus impurities were resubjected to prepatory chromatography eluting with 25 to 35% acetone:hexane over a thirty-minute period. Fractions containing title compound were combined and concentrated in vacuo to afford 8.9 g (82%).

mp 160(°C.):

Mass Spectrum (FDMS): m/z

1H NMR (CdCL3): δ 9.90 (s, 1H),7.85 (d, 4H), 7.69 (s,1H), 7.12 (d, 2H), 5.54 (s, 1H), 5.14 (s, 2H), 1.49 (s, 18H).

Elemental Analysis for: $C_{25}H_{29}NO_4$ Calculated: C, 73.69; H, 7.17; N, 3.44. Found: C, 73.72; H, 7.16; N, 3.45.

G. 2-(3,5-di-tert-butyl-4-hydroxyphenyl))-4-((4-N-methylethylamino methyl)phenoxymethyl)oxazole hydrochloride The title compound was prepared substantially as described in Example 11, except using 4-(4-(2-formyl) phenoxy methyl)-2-(3,5-di-tert-butyl-4-hydroxyphenyl)) and N-methyl-n-ethylamine. The crude material was subjected to prepatory chromatography eluting with 0 to 10% (methanol:ammonium hydroxide):chloroform over a 30-minute period. Fractions containing title compound were combined and concentrated in vacuo to afford 6.0 g. The material was dissolved in diethyl ether (100 ml) then saturated with hydrochloric gas. The resulting precipatae was collected by filtration and washed with diethyl ether. This material was dissolved in methylene chloride (50 ml) and washed with 0.1N ammoniumhydroxide (50 ml). The organic layer was dried over sodium sulfate then filtered. The filtrate was subjected to prepatory chromatography eluting with 0 to 10% (methanol:ammonium hydroxide) :chloroform. Fractions containing title compound combined, concentrated in vacuo to a foam. The foam was treated with diethyl ether (100 ml) and saturated aqueous sodium bicarbonate (100 ml). The phases were separated, aqueous phase extracted with diethyl ether (1×50 ml). The organic phases were combined, dried over sodium sulfate, filtered, then slowly added to a saturated solution of hydrogen chloride diethyl ether. The resulting suspension was concentrated in vacuo to afford 4.74 g of the title compound as a foam.

Mass Spectrum (FDMS): m/z 450 (M-HCl)

$^1$H NMR (CDCl$_3$): δ 7.86 (s, 2H), 7.68 (s, 1H), 7.52 (d, J=8.6 Hz, 2H) 7.06 (d, J=8.6 Hz, 2H), 5.54 (s, 1H), 5.07 (s, 2H), 4.10 (M, 2H), 3.17 (m, 1H), 2.91 (m, 1H), 2.64 (d, J=5.0Hz, 3H), 1.48 (m, 21H)

Elemental Analysis for: $C_{28}H_{39}ClN_2O_3$ Calculated: C, 69.05; H, 8.07; N, 5.75 Found: C, 68.95; H, 7.98; N, 5.76

Pharmaceutical Composition

In the composition of this invention a compound of formula I or a pharmaceutically acceptable salt thereof and one or more Drug Useful in the Treatment of Pain are combined in a weight ratio of a compound of formula I to Drug Useful in the Treatment of Pain of from about one (1) to from about one (1) to about one thousand (1000) parts Drug Useful in the Treatment of Pain.

A preferred composition is a weight ratio of a compound of formula I to Drug Useful in the Treatment of Pain of from about one (1) part of a compound of formula I to from about one (1) to about one hundred (100) parts Drug Useful in the Treatment of Pain. An especially preferred ratio is from about one part of a compound of formula I to from about one (1) to about thirty (30) parts Drug Useful in the Treatment of Pain. A further preferred ratio may be from about one part of a compound of formula I to from about one (1) to about ten (10) parts Drug Useful in the Treatment of Pain. A final preferred ratio may be from about one (1) part of a compound of formula I to from about one (1) to about three (3) parts Drug Useful in the Treatment of Pain.

The compounds of formula I are effective over a wide dosage range; however, it is desirable to administer a dosage that is as low as possible. The amount of Drug Useful in the Treatment of Pain present in the composition is adjusted as described above in ratio to the compound of formula I dosage. For example, dosages per day of the compound of formula I will normally fall within the range of about 0.1 mg to about 30 mg per day and the Drug Useful in the Treatment of Pain in the composition would be from about 3 to about 1000 times this amount. Usually, the daily dosage can be such that the active ingredient is administered at a daily dosage of from about 0.2 mg to about 30 mg of a compound of formula I and from about 0.6 to about 200 mg/kg of Drug Useful in the Treatment of Pain.

However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. The dosage administered will, of course, also vary depending on known factors such as the pharmacodynamic characteristics of the particular agent, and its mode and route of administration; kind of concurrent treatment, frequency of treatment, and the effect desired.

While the present compounds are preferably administered orally to humans susceptible to or suffering from pain, the compounds may also be administered by a variety of other routes such as the transdermal, parenteral, subcutaneous, intranasal, intramuscular and intravenous routes. Such formulations may be designed to provide delayed or controlled release using formulation techniques which are known in the art.

Compositions suitable for internal administration contain from about one half (0.5) milligrams to about 600 milligrams of active ingredient per unit. In these pharmaceutical compositions, the active ingredient will ordinarily be present in an amount of from about 0.5% to about 95% by weight based on the total weight of the composition.

Typical compositions include a compound of formula I or a pharmaceutically acceptable acid addition salt thereof and one or more Drug Useful in the Treatment of Pain, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredients after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the composition is dispensed in unit form comprising from about 1 mg to about 30 mg in a pharmaceutically acceptable carrier per unit dosage.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The compositions of this invention may be suitable for administration to an animal. Such animals include both domestic animals, for example livestock, laboratory animals, and household pets, and non-domestic animals such as wildlife. More preferably, the animal is a vertebrate. Most preferably, a composition of this invention shall be administered to a mammal. It is especially preferred that the animal is a domestic mammal or a human. For domestic mammals, a composition of this invention may be administered as a feed additive. The most preferred mammal is a human.

Assays

Utility Test Methods

The unexpectedly enhanced analgesic activity of the composition of the invention is evidenced by tests initially conducted on mice. Mice weighing from about 18–25 grams at the time of testing are used for the following studies. All mice are dosed by the oral route with a compound of formula I and/or Drug Useful in the Treatment of Pain.

Mouse Writhing Test

An accepted standard for detecting and comparing the analgesic activity of the combination of different classes of analgesic compounds for which there is a good correlation with human analgesic activity is the prevention of acetic acid induced writhing in mice [R. Koster et al. Acetic acid for analgesic screening. Fed. Proc. 18:412, 1959].

Adult, male CD-1 [Crl:CDR-1(ICR)] mice (approximately 4–5 weeks of age), were obtained from Charles Rier Laboratories, Portage, Mich., and acclimated at least 3 days before testing. The photo period was 12 hours of light and 12 hours of dark, with dark onset at approximately 1800 hours.

Throughout the study, suspensions were prepared at target concentrations of 0, 0.3, 0.1, 0.3, and 1 mg/ml of a compound of formula I by the addition of 10% acacia in purified water. The vehicle control consisted of 10% acacia in purified water.

Analgesic activity following administration of a compound of formula I in combination with another analgesic drug was evaluated using acetic acid-induced writhing. An intraperitoneal injection of acetic acid in mice causes them to exhibit contractions of the abdominal muscles, or writhe (Siegmund et al., 1957). Administration of either opioid or nonopioid analgesics reduces the amount of writhing (Collier, 1964). Writhing has been used to define the pharmacology of analgesics such as aspirin and morphine. Approximately 30 minutes following oral administration of a compound of formula I (0, 0.3, 1, 3, or 10 or 30 mg/kg), each mouse received 0.5% acetic acid (0.01 ml/g, intraperitoneal). Mice were placed in individual clear observation chambers and the total number of writhes made by each mouse was counted between 5 and 10 minutes following administration of acetic acid. See, Haubrich, D. R., Ward, S. J., Baizman, E., Bell, M. R., Bradford, J., Ferrari, R., Miller, M., Perrone, M., Pierson, A. K., Saelens, J. K. and Luttinger, D.: "Pharmacology of pravadoline: a new analgesic agent", *The Journal of Pharmacology and Experimental Therapeutics* 255 (1990) 511–522.

The interaction of a compound of formula I and Drug Useful in the Treatment of Pain on analgesia in mice is demonstrated by Loewe isobologram analysis. (S. Loewe, Pharm. Rev. 9:237–242, 1957). In the isobolographic analysis, the analgesic effects of a compound of formula I are presented on the X-axis and of the other compound used in the treatment of pain on the Y-axis. The line connecting the $ED_{50}$ dosages of a compound of formula I alone and Drug Useful in the Treatment of Pain alone represents the "ED50 addition line" which indicates the expected location of the $ED_{50}$ values for a compound of formula I and Drug Useful in the Treatment of Pain combinations if simple additivity were to describe their combined effects. According to Loewe's isobolographic theory, if the analgesic effects of a compound of formula I and an Drug Useful in the Treatment of Pain were simply additive to one another, the expected location of the $ED_{50}$ values of the compound of formula I and Drug Useful in the Treatment of Pain components of each fixed dosage ratio would lie on the addition line. Combination ED50 values located significantly below the $ED_{50}$ addition line would represent unexpectedly enhanced analgesic activity and combination $ED_{50}$ values located above the line would represent unexpected diminished analgesic effect.

One method to establish the significance of such unexpected enhanced or diminished activity is to calculate the SEM values for each $ED_{50}$. If the SEM values do not overlap the line of addition, then the ED50 values are significantly different from the line of addition.

Clinical Observations

A double-blind multicenter clinical trial is designed to assess the safety and efficacy of a compound of formula I. Patients are randomized to a compound of formula I, composition of this invention, Drug Useful in the Treatment of Pain alone, or placebo. Patients are monitored for perception of pain using standard methods.

We claim:

1. A composition for treating pain comprising a compound of formula I;

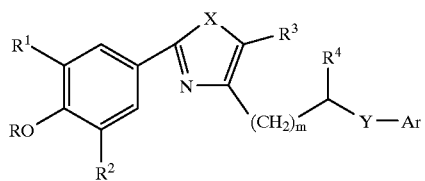

wherein

Ar is phenyl or pyridyl substituted with zero to two substituents selected from the group consisting of $C_1$–$C_6$ alkyl, hydroxy and halo; and substituted with either:

(i) one or two substituents selected from the group consisting of

and ($C_1$–$C_6$ alkyl)$R^6$; or (ii) two substituents which when taken together with the carbon atoms to which they are attached form a pyridyl or tetrahydropyridyl ring;

provided that when substituent pattern (i) is present, the phenyl or pyridyl group of Ar may additionally be substituted with two substituents which when taken together with the carbon atoms to which they are attached form a phenyl ring;

where $R^6$ is $NR^7R^8$, morpholin-1-yl, imidazol-1-yl, 4,5-dihydro-1H-imidazol-2-yl, thiomorpholin-1-yl, piperazin-1-yl or piperazin-1-yl substituted with $C_1$–$C_4$ alkyl or

and $R^7$ and $R^8$ are each individually hydrogen, $C_1$–$C_6$ alkyl, $(CH_2)_pOH$ or $(CH_2)_p$-piperidyl;

X is O or S;

Y is $CHR^5$, O or S;

R is H or $C_1$–$C_6$ alkyl;

$R^1$ and $R^2$ are each individually $C_1$–$C_6$ alkyl;

$R^3$ is H or $C_1$–$C_6$ alkyl;

$R^4$ is hydrogen, or when Y is $CHR^5$, $R^4$ and $R^5$ are each individually H or when taken together form a bond;

m is 0 or 1;

n is an integer from 0 to 4 both inclusive; and p is an integer from 1 to 6 both inclusive;

or a pharmaceutically acceptable salt, hydrate or optical isomer thereof; and one or more Drug Useful in the Treatment of Pain in a weight ratio of from about one part of a compound of formula I to from about one (1) part to about one thousand (1000) parts Drug Useful in the Treatment of Pain.

2. The composition of claim 1 wherein Ar of the compound of formula I is phenyl substituted with one or two substituents selected from —$(CH_2)_nR^6$,

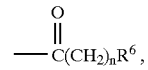

—($C_1$–$C_6$ alkyl)$R^6$ where $R^6$ is $NR^7R^8$ and $R^7$ and $R^8$ are H or $C_1$–$C_6$ alkyl;

and one or two substituents selected from hydrogen, $C_1$–$C_6$-alkyl, hydroxy; or two substituents which when taken together form a phenyl group;

$R^1$ and $R^2$ are $C_1$–$C_6$ alkyl;

R, $R^3$, $R^4$ and R are H;

X is O

Y is O or S.

3. The composition of claim 2 wherein $R^1$ and $R^2$ of the compound of formula I are 1,1-dimethylethyl.

4. The composition of claim 3 wherein Ar of the compound of formula I is phenyl substituted with one or two substituents selected from $(CH_2)_nR^6$ or ($C_1$–$C_6$ alkyl)$R^6$ and one or two substituents selected from hydrogen or $C_1$–$C_6$ alkyl.

5. The composition of claim 4 wherein Ar of the compound of formula I is phenyl substituted with $(CH_2)_nR^6$.

6. The composition of claim 5 wherein the compound of formula I is 2-(3,5-di-t-butyl-4-hydroxyphenyl)-4-(2-(4-methylethylaminomethyl-phenyloxy)ethyl)oxazole.

7. The composition of claim 1 wherein the Drug Useful in the Treatment of Pain is an NSAID.

8. The composition of claim 7 wherein the NSAID is selected from the group consisting of aspirin, indomethacin, ibuprofen, naproxen, fenoprofen, tolmetin, sulindac, meclofenamate, ketoprofen, piroxicam, flurbiprofen, and diclofenac or a pharmaceutically acceptable salt thereof.

9. The composition of claim 8 wherein the Drug Useful in the Treatment of Pain is selected from the group consisting of aspirin, ibuprofen, and naproxen.

10. The composition of claim 1 wherein the weight ratio of a compound of formula I to Drug Useful in the Treatment of Pain is from about one part of a compound of formula I to from about one (1) to about one hundred (100) parts Drug Useful in the Treatment of Pain.

11. The composition of claim 10 wherein the weight ratio is from about one part of a compound of formula I to from about one (1) to about thirty (30) parts Drug Useful in the Treatment of Pain.

12. The composition of claim 11 wherein the weight ratio is from about one part of a compound of formula I to from about one (1) to about ten (10) parts Drug Useful in the Treatment of Pain.

13. The composition of claim 1 wherein the Drug Useful in the Treatment of Pain is selected from the group consisting of morphine, acetaminophen, ibuprofen, and diclofenac.

14. The composition of claim 1 wherein the Drug Useful in the Treatment of Pain is an opioid compound.

15. The composition of claim 14 wherein the opioid compound is selected from the group consisting of morphine, codeine, meperidine, methadone, propoxyphene, levorphanol, hydromorphone, oxymorphone, oxycodone, brompton's cocktail, pentazocine, butorphanol, nalbuphine, and buprenorphine.

16. The composition of claim 15 wherein the opioid compound is selected from the group consisting of morphine, oxymorphine, oxycodone, hydromorphine, codeine, and methadone.

17. The composition of claim 1 wherein the Drug Useful in the Treatment of Pain is selected from the group consisting of Tylenol #3, tricyclic antidepressants, anticonvulsants, serotonin reuptake inhibitors, mixed serotonin-norepinephrine reuptake inhibitors, serotonin receptor agonists and antagonists, cholinergic analgesics, and neurokinin antagonists.

18. The composition of claim 17 wherein the Drug Useful in the Treatment of Pain is selected from the group consisting of Tylenol #3, tricyclic antidepressants, anticonvulsants, serotonin reuptake inhibitors, mixed serotonin-norepinephrine reuptake inhibitors analgesics, and neurokinin antagonists.

19. The composition of claim 18 wherein the Drug Useful in the Treatment of Pain is a tricyclic antidepressant.

20. The composition of claim 1 wherein the Drug Useful in the Treatment of Pain is an alpha adrenergic compound.

21. The composition of claim 20 wherein the alpha adrenergic compound is Clonidine or a pharmaceutically acceptable salt thereof.

22. A method for treating pain in a mammal in need thereof comprising administering to said mammal an analgesic dose of a composition comprising a compound of formula I;

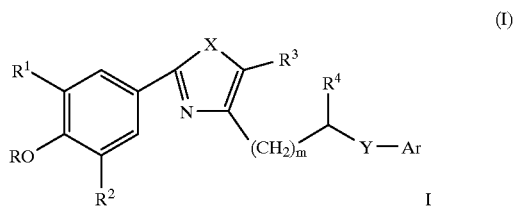

wherein

Ar is phenyl or pyridyl substituted with zero to two substituents selected from the group consisting of $C_1$–$C_6$ alkyl, hydroxy and halo; and substituted with either:

(i) one or two substituents selected from the group consisting of

and $(C_1$–$C_6$ alkyl$)R^6$; or (ii) two substituents which when taken together with the carbon atoms to which they are attached form a pyridyl or tetrahydropyridyl ring;

provided that when substituent pattern (i) is present, the phenyl or pyridyl group of Ar may additionally be substituted with two substituents which when taken together with the carbon atoms to which they are attached form a phenyl ring;

where $R^6$ is $NR^7R^8$, morpholin-1-yl, imidazol-1-yl, 4,5-dihydro-1H-imidazol-2-yl, thiomorpholin-1-yl, piperazin-1-yl or piperazin-1-yl substituted with $C_1$–$C_4$ alkyl or

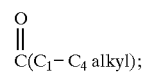

and $R^7$ and $R^8$ are each individually hydrogen, $C_1$–$C_6$ alkyl, $(CH_2)_pOH$ or $(CH_2)_p$-piperidyl;

X is O or S;

Y is $CHR^5$, O or S;

R is H or $C_1$–$C_6$ alkyl;

$R^1$ and $R^2$ are each individually $C_1$–$C_6$ alkyl;

$R^3$ is H or $C_1$–$C_6$ alkyl;

$R^4$ is hydrogen, or when Y is $CHR^5$, $R^4$ and $R^5$ are each individually H or when taken together form a bond;

m is 0 or 1;

n is an integer from 0 to 4 both inclusive; and p is an integer from 1 to 6 both inclusive;

or a pharmaceutically acceptable salt, hydrate or optical isomer thereof; and one or more Drug Useful in the Treatment of Pain in a weight ratio of a compound of formula I to Drug Useful in the Treatment of Pain of from about one part of a compound of formula I to from about one (1) to about one thousand (1000) parts Drug Useful in the Treatment of Pain.

23. The method of claim 22 where:

Ar is phenyl substituted with one or two substituents selected from —$(CH_2)_nR^6$,

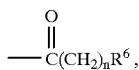

—($C_1$–$C_6$ alkyl)$R^6$ where $R^6$ is $NR^7R^8$ and $R^7$ and $R^8$ are H or $C_1$–$C_6$ alkyl;

and one or two substituents selected from hydrogen, $C_1$–$C_6$-alkyl, hydroxy; or two substituents which when taken together form a phenyl group;

$R^1$ and $R^2$ are $C_1$–$C_6$ alkyl;

R, $R^3$, $R^4$ and R are H;

X is O

Y is O or S.

24. The method of claim 23 where $R^1$ and $R^2$ are 1,1-dimethylethyl.

25. The method of claim 24 where Ar is phenyl substituted with one or two substituents selected from $(CH_2)_nR^6$ or ($C_1$–$C_6$ alkyl)$R^6$ and one or two substituents selected from hydrogen or $C_1$–$C_6$ alkyl.

26. The method of claim 25 where Ar is phenyl substituted with $(CH_2)_nR^6$.

27. The method of claim 26 wherein the compound of formula I is 2-(3,5-di-t-butyl-4-hydroxyphenyl)-4-(2-(4-methylethylaminomethyl-phenyloxy)ethyl)oxazole.

28. The method of claim 22 wherein the Drug Useful in the Treatment of Pain is an NSAID.

29. The method of claim 22 wherein the weight ratio of a compound of formula I to Drug Useful in the Treatment of Pain is from about one (1) part of a compound of formula I to from about one (1) to about one hundred (100) parts Drug Useful in the Treatment of Pain.

30. The method of claim 22 wherein the weight ratio of a compound of formula I to Drug Useful in the Treatment of Pain is from about one (1) part of a compound of formula I to from about one (1) to about thirty (30) parts Drug Useful in the Treatment of Pain.

31. The method of claim 22 wherein the Drug Useful in the Treatment of Pain is selected from the group consisting of alpha adrenergic compounds and opioid compounds.

32. The method of claim 22 wherein the Drug Useful in the Treatment of Pain is selected from the group consisting of Tylenol #3, tricyclic antidepressants, anticonvulsants, serotonin reuptake inhibitors, mixed serotonin-norepinephrine reuptake inhibitors analgesics, and neurokinin antagonists.

33. The method of claim 22 wherein pain is neuropathic pain.

34. The method of claim 33 wherein the neuropathic pain is selected from the group consisting of lower back pain, pain associated with arthritis, cancer-associated pain, herpes neuralgia, phantom limb pain, central pain, opiod resistant neuropathic pain, bone injury pain, and pain during labor and delivery.

35. The method of claim 22 wherein pain is nociceptive pain.

36. The method of claim 35 wherein the nociceptive pain is selected from the group consisting of post-operative pain, cluster headaches, dental pain, surgical pain, pain resulting from severe burns, pain from third degree burns, post partum pain, angina pain, genitourinary tract related pain, and pain from cystitis.

37. The method of claim 22 wherein the pain is acute pain.

38. The method of claim 37 wherein the acute pain is selected from the group consisting of headache, arthritis, simple muscle strain, and dysmenorrhea.

\* \* \* \* \*